(12) United States Patent
Ohashi et al.

(10) Patent No.: US 8,609,889 B2
(45) Date of Patent: Dec. 17, 2013

(54) PHOTOACID GENERATOR, RESIST COMPOSITION, AND PATTERNING PROCESS

(75) Inventors: Masaki Ohashi, Joetsu (JP); Youichi Ohsawa, Joetsu (JP); Takeshi Kinsho, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 288 days.

(21) Appl. No.: 12/828,557

(22) Filed: Jul. 1, 2010

(65) Prior Publication Data
US 2011/0003247 A1 Jan. 6, 2011

(30) Foreign Application Priority Data

Jul. 2, 2009 (JP) ................................ 2009-157856

(51) Int. Cl.
G03F 7/028 (2006.01)
G03F 7/26 (2006.01)
C07C 309/06 (2006.01)
C07C 309/07 (2006.01)

(52) U.S. Cl.
USPC .......... 562/30; 430/270.1; 430/326; 430/921; 430/923; 430/925

(58) Field of Classification Search
USPC ...................... 430/270.1, 326, 921, 923, 925; 552/112; 554/96; 562/30; 568/24, 27, 568/28
See application file for complete search history.

(56) References Cited

U.S. PATENT DOCUMENTS

| | | | |
|---|---|---|---|
| 5,635,332 A | 6/1997 | Nakano et al. | |
| 5,650,483 A | 7/1997 | Malik et al. | |
| 5,705,702 A | 1/1998 | Osawa et al. | |
| 6,048,672 A | 4/2000 | Cameron et al. | |
| 6,306,555 B1 | 10/2001 | Schulz et al. | |
| 6,312,867 B1 | 11/2001 | Kinsho et al. | |
| 6,440,634 B1 | 8/2002 | Ohsawa et al. | |
| 6,723,483 B1 | 4/2004 | Oono et al. | |
| 6,830,866 B2 | 12/2004 | Kobayashi et al. | |
| 6,849,374 B2 | 2/2005 | Cameron et al. | |
| 7,288,359 B2 | 10/2007 | Iwasawa et al. | |
| 7,527,912 B2 | 5/2009 | Ohsawa et al. | |
| 7,537,880 B2 | 5/2009 | Harada et al. | |
| 7,556,909 B2 | 7/2009 | Kobayashi et al. | |
| 7,569,326 B2 | 8/2009 | Ohsawa et al. | |
| 7,612,217 B2 | 11/2009 | Sakamoto et al. | |
| 7,670,751 B2 | 3/2010 | Ohashi et al. | |
| 7,704,668 B1 | 4/2010 | Cameron et al. | |
| 2002/0197558 A1 | 12/2002 | Ferreira et al. | |
| 2003/0113659 A1 | 6/2003 | Hatakeyama et al. | |
| 2004/0260031 A1 | 12/2004 | Takeda et al. | |
| 2005/0202340 A1* | 9/2005 | Houlihan et al. | 430/270.1 |
| 2006/0040203 A1 | 2/2006 | Kodama et al. | |
| 2007/0003871 A1 | 1/2007 | Kodama et al. | |
| 2007/0122750 A1 | 5/2007 | Yamaguchi et al. | |
| 2007/0231738 A1 | 10/2007 | Kaneko et al. | |
| 2008/0026331 A1 | 1/2008 | Hasegawa et al. | |
| 2008/0085469 A1* | 4/2008 | Ohsawa et al. | 430/286.1 |
| 2008/0318160 A1 | 12/2008 | Ohsawa et al. | |
| 2009/0061358 A1* | 3/2009 | Ohashi et al. | 430/286.1 |
| 2009/0202943 A1* | 8/2009 | Ohsawa et al. | 430/285.1 |
| 2009/0246694 A1* | 10/2009 | Ohsawa et al. | 430/285.1 |
| 2010/0055608 A1* | 3/2010 | Ohashi et al. | 430/270.1 |
| 2010/0113818 A1* | 5/2010 | Oh et al. | 560/17 |
| 2010/0316952 A1* | 12/2010 | Ichikawa et al. | 430/270.1 |

FOREIGN PATENT DOCUMENTS

| | | |
|---|---|---|
| EP | 0 473 547 A1 | 3/1992 |
| JP | 4-230645 A | 8/1992 |
| JP | 7-25846 A | 1/1995 |
| JP | 8-311018 A | 11/1996 |
| JP | 9-15848 A | 1/1997 |
| JP | 11-282168 A | 10/1999 |
| JP | 2000-122296 A | 4/2000 |
| JP | 2000-336121 A | 12/2000 |
| JP | 2001-122850 A | 5/2001 |
| JP | 2001-181221 A | 7/2001 |
| JP | 2002-193887 A | 7/2002 |
| JP | 2002-193925 A | 7/2002 |
| JP | 2002-214774 A | 7/2002 |
| JP | 2003-66612 A | 3/2003 |
| JP | 2003-140332 A | 5/2003 |
| JP | 2004-2252 A | 1/2004 |
| JP | 2004-115630 A | 4/2004 |
| JP | 2004-531749 A | 10/2004 |
| JP | 2005-8766 A | 1/2005 |
| JP | 2005-84365 A | 3/2005 |

(Continued)

OTHER PUBLICATIONS

Arimitsu et al., "Effect of Phenolic Hydroxyl Residues on the Improvement of Acid-Proliferation -Type Photoimaging Materials", Journal of Photopolymer Science and Technology, vol. 9, No. 1, 1996, pp. 29-30.

Arimitsu et al., "Sensitivity Enhancement of Chemical-Amplification-Type Photoimaging Materials by Acetoacetic Acid Derivatives", Journal of Photopolymer Science and Technology, vol. 8, No. 1, 1995, pp. 43-44.

Dammel et al., "193 nm Immersion Lithography—Taking the Plunge", Journal of Photopolymer Science and Technology, vol. 17, No. 4, 2002, pp. 587-601.

Devoe et al., "Photochemistry and Photophysics of 'Onium Salts*'", Advances in Photochemistry, John-Wiley & Sons, 1992, vol. 17.

(Continued)

Primary Examiner — Anca Eoff
(74) Attorney, Agent, or Firm — Birch, Stewart, Kolasch & Birch, LLP

(57) ABSTRACT

The photoacid generator produces a sulfonic acid which has a bulky cyclic structure in the sulfonate moiety and a straight-chain hydrocarbon group and thus shows a controlled acid diffusion behavior and an adequate mobility. The PAG is fully compatible with a resin to form a resist composition which performs well during the device fabrication process and solves the problems of resolution, LWR, and exposure latitude.

15 Claims, 11 Drawing Sheets

(56) References Cited

FOREIGN PATENT DOCUMENTS

| | | |
|---|---|---|
| JP | 2005-266766 A | 9/2005 |
| JP | 2007-145797 A | 6/2007 |
| JP | 2007-145804 A | 6/2007 |
| JP | 2007-161707 A | 6/2007 |
| JP | 2007-297590 A | 11/2007 |
| JP | 2008-31298 A | 2/2008 |
| JP | 2008-69146 A | 3/2008 |
| JP | 2008-106045 A | 5/2008 |
| JP | 2008-111103 A | 5/2008 |
| JP | 2008-133448 A | 6/2008 |
| JP | 2009-80474 A | 4/2009 |

OTHER PUBLICATIONS

Houlihan et al., " Effect of Amine Additives on LWR and LER as Studied by Extraction Parameters", Journal of Photopolymer Science and Technology, vol. 19, No. 3, 2006, pp. 327-334.

Kudo et al., "Enhancement of the Senesitivity of Chemical-Amplification-Type Photoimaging Materials by β-Tosyloxyketone Acetals.", Journal of Photopolymer Science and Technology, vol. 8, No. 1, 1995, pp. 45-46.

Lowe, "Synthesis of sulphonium salts", The Chemistry of the Sulphonium Group Part 1, John-Wiley & Sons, 1981, pp. 268-312.

Miller et al., "Deoxygenation of Sulfoxides Promoted by Electrophilic Silicon Reagents: Preparation of Aryl-Substituted Sulfonium Salts", J. Org. Chem., 1988, 53, pp. 5571-5573.

\* cited by examiner

PHOTOACID GENERATOR, RESIST COMPOSITION, AND PATTERNING PROCESS

CROSS-REFERENCE TO RELATED APPLICATION

This non-provisional application claims priority under 35 U.S.C. §119(a) on Patent Application No. 2009-157856 filed in Japan on Jul. 2, 2009, the entire contents of which are hereby incorporated by reference.

TECHNICAL FIELD

This invention relates to novel photoacid generators, resist compositions comprising the same, and a patterning process using the same.

BACKGROUND ART

While a number of recent efforts are being made to achieve a finer pattern rule in the drive for higher integration and operating speeds in LSI devices, deep-UV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using F$_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004).

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkane- or arene-sulfonic acid are used. However, the use of these photoacid generators in chemically amplified resist compositions for ArF lithography results in an insufficient acid strength to scissor acid labile groups on the resin, a failure of resolution or a low sensitivity. Thus these photoacid generators are not suited for the fabrication of microelectronic devices.

For the above reason, photoacid generators capable of generating perfluoroalkanesulfonic acid having a high acid strength are generally used in ArF chemically amplified resist compositions. These photoacid generators capable of generating perfluoroalkanesulfonic acid have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application Publication 2003-0113659 A1 (JP-A 2003-140332), and US Patent Application Publication 2002-0197558 A1 describe novel photoacid generators capable of generating perfluoroalkyl ether sulfonic acids.

On the other hand, perfluorooctanesulfonic acid and homologues thereof (collectively referred to as PFOS) are considered problematic with respect to their stability (or non-degradability) due to C—F bonds, and biological concentration and accumulation due to hydrophobic and lipophilic natures. The US EPA adopted Significant New Use Rule, listing 13 PFOS-related chemical substances and further listing 75 chemical substances although their use in the photoresist field is excluded. It has already been proposed to apply the Rule to perfluoroalkanesulfonic acids and derivatives thereof, summing to 183 chemical substances.

Facing the PFOS-related problems, manufacturers made efforts to develop partially fluorinated alkane sulfonic acids having a reduced degree of fluorine substitution. For instance, JP-A 2004-531749 describes the development of α,α-difluoroalkanesulfonic acid salts from α,α-difluoroalkene and a sulfur compound and discloses a resist composition comprising a photoacid generator which generates such sulfonic acid upon irradiation, specifically di(4-tert-butylphenyl)-Iodonium 1,1-difluoro-2-(1-naphthyl)ethanesulfonate. JP-A 2004-002252 describes the development of α,α,β,β-tetrafluoro-alkanesulfonic acid salts from α,α,β,β-tetrafluoro-α-iodoalkane and sulfur compound and discloses a photoacid generator capable of generating such a sulfonic acid and a resist composition comprising the same. JP-A 2002-214774 discloses such photoacid generators having difluorosulfoacetic acid alkyl esters (e.g., 1-(alkoxycarbonyl)-1,1-difluoromethanesulfonate) and difluorosulfoacetic acid amides (e.g., 1-carbamoyl-1,1-difluoromethanesulfonate) although their synthesis method is lacking. Furthermore, JP-A 2005-266766 discloses a photosensitive composition comprising a compound capable of generating a partially fluorinated alkane sulfonic acid having a sulfonylamide structure derived from perfluoroalkylene disulfonyl difluoride.

The substances disclosed in these patent documents have a reduced degree of fluorine substitution, but suffer from several problems. They are less degradable because they are based on substantially undegradable hydrocarbon skeletons and they do not possess readily degradable substituent groups such as ester groups. A certain limit is imposed on the molecular design for changing the size of alkanesulfonic acid. The starting materials containing fluorine are expensive.

Aside from the degradation and acid strength of photoacid generators, there are many problems to be solved. For instance, as the pattern layout becomes finer, the fluctuation of pattern line width, known as "line width roughness" (LWR), becomes significant. In the processing of gate electrode zones in the LSI circuit manufacturing process, for example, poor LWR can give rise to such problems as current leakage, resulting in a transistor with degraded electrical properties. It is believed that the LWR is affected by various factors. The main factor is the poor affinity of a base resin to a developer, that is, low solubility of a base resin in a developer. Since carboxylic acid protective groups commonly used in the art are bulky tertiary alkyl groups and thus highly hydrophobic, most of them are less soluble. Where a high resolution is required as in the formation of microscopic channels, a noticeable LWR can lead to an uneven size. One of known approaches for reducing LWR is by increasing the amount of photoacid generator added, as described in Journal of Photopolymer Science and Technology, Vol. 19, No. 3, 327-334 (2006). This approach, however, exerts a less than satisfactory effect, sometimes at the substantial sacrifice of exposure dose dependency, mask fidelity and/or pattern rectangularity. Aside from merely increasing the amount, uniform distribution of the photoacid generator is also important for improving LWR.

Furthermore, as the circuit line width is reduced, the detrimental influence of acid diffusion on contrast becomes more serious for resist materials. This is because the pattern size is approaching the diffusion length of acid. The acid diffusion may also lead to a lowering of mask fidelity and a degradation of pattern rectangularity. Therefore, in order to take full advantage of the reduced wavelength of a light source and the increased NA, it is necessary to increase the dissolution contrast over prior art materials or to restrain the acid diffusion.

JP-A 2007-145797 discloses $C_1$-$C_{20}$ alkanecarbonyloxy or arenecarbonyloxy-1,1,3,3,3-pentafluoropropanesulfonates, typically triphenylsulfonium 2-(adamantane-1-carbonyloxy)-1,1,3,3,3-pentafluoropropanesulfonate. They are still insufficient in diffusion control and LWR reduction.

JP-A 2007-161707 and JP-A 2008-069146 disclose photoacid generators capable of generating partially fluorinated alkanesulfonic acids having a polycyclic hydrocarbon group. These compositions still fail to exert satisfactory resist performance. Since these photoacid generators are unstable esters of difluoroacetic acid, shelf stability is a matter of concern about the resist compositions comprising the same.

In the actual device fabrication process, the exposure dose can vary in a certain range. The resist is required to have an exposure latitude sufficient to maintain a pattern profile substantially the same even when a certain variation of exposure dose occurs. Under the current demand for a further miniaturization of the pattern rule, the resist is required to perform well with respect to sensitivity, substrate adhesion, and etch resistance, and additionally, to achieve an LWR improvement and exposure latitude without the concomitant degradation of resolution.

With respect to the immersion lithography, there remain some problems. Minute water droplets are left on the resist and wafer after the immersion exposure, which can often cause damages and defects to the resist pattern profile. The resist pattern after development can collapse or deform into a T-top profile. In the immersion lithography, there exists a need for a patterning process which can form a satisfactory resist pattern after development.

CITATION LIST

Patent Document 1: JP-A 2000-122296
Patent Document 2: JP-A H11-282168
Patent Document 3: JP-A 2002-214774
Patent Document 4: US 20030113659 A1 (JP-A 2003-140332)
Patent Document 5: US 20020197558 A1
Patent Document 6: JP-A 2004-531749
Patent Document 7: JP-A 2004-002252
Patent Document 8: JP-A 2005-266766
Patent Document 9: JP-A 2007-145797
Patent Document 10: JP-A 2007-161707
Patent Document 11: JP-A 2008-069146
Non-Patent Document 1: Journal of Photopolymer Science and Technology, Vol. 17, No. 4, p 587 (2004)
Non-Patent Document 2: Journal of Photopolymer Science and Technology, Vol. 19, No. 3, p 327-334 (2006)

SUMMARY OF INVENTION

The photoacid generator (PAG) produces an acid which must satisfy many requirements including a sufficient acid strength to cleave acid labile groups in a resist material, stability in the resist material during shelf storage, an adequate diffusion in the resist material, low volatility, minimal leach-out in water, little foreign matter left after development and resist removal, and good degradability in that it is decomposed away after the expiration of its role in lithography without imposing a load to the environment. No acids produced by prior art PAGs satisfy these requirements. Moreover, resist compositions using prior art PAGs fail to solve the problems of LWR and exposure latitude without sacrifice of resolution.

An object of the invention is to solve the problems of prior art photoacid generators, and to provide novel photoacid generators suited for use in resist materials which generators are effective in the ArF immersion lithography due to minimized leach-out in water and controlled formation of foreign matter inherent to the immersion lithography, and overcome the problems of LWR and exposure latitude. Another object is to provide a resist composition using the photoacid generator, and a patterning process.

The inventors have found that compounds having the specific structure shown below are effective photoacid generators in chemically amplified resist compositions. The present invention provides a novel photoacid generator, a resist composition, and a patterning process, as defined below.

A first embodiment of the invention is a chemically amplified resist composition comprising a photoacid generator which generates a sulfonic acid having the general formula (1) in response to high-energy radiation or heat.

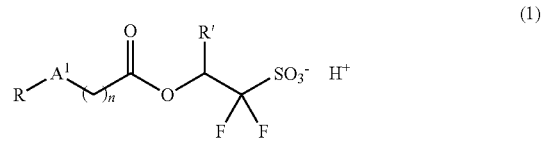

(1)

Herein R is a substituted or unsubstituted, monovalent hydrocarbon group having an aromatic ring or alicyclic hydrocarbon structure of at least 5 carbon atoms, R' is hydrogen or trifluoromethyl, $A^1$ is an ester, ether, thioether, amide or carbonate bond, and n is an integer of 1 to 3.

A second embodiment is a sulfonium salt having the general formula (2).

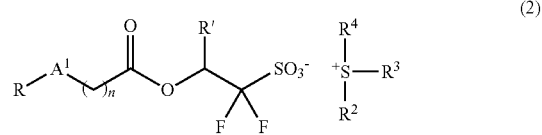

(2)

Herein R, R', $A^1$ and n are as defined above, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom.

A third embodiment is a sulfonium salt having the general formula (3).

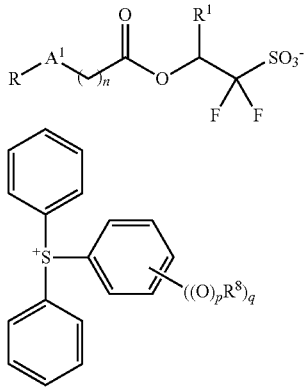
(3)

Herein R, R', $A^1$ and n are as defined above, $R^8$ is a substituted or unsubstituted, straight, branched or cyclic $C_1$-$C_2$ alkyl or alkenyl group or a substituted or unsubstituted $C_6$-$C_{14}$ aryl group, p is 0 or 1, and q is an integer of 1 to 5.

A fourth embodiment is a iodonium salt having the general formula (4).

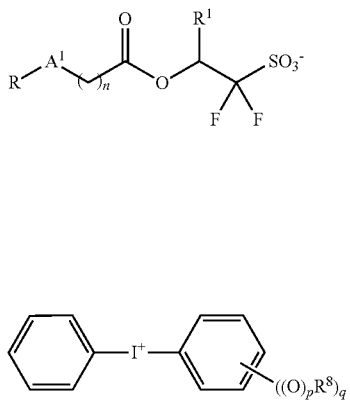
(4)

Herein R, R', $A^1$, n, $R^8$, p, and q are as defined above.

A fifth embodiment is a resist composition comprising a base resin, an acid generator, a quencher, and an organic solvent, said acid generator comprising a photoacid generator which generates a sulfonic acid having formula (1) as set forth above.

A sixth embodiment is a chemically amplified positive resist composition comprising a base resin which is insoluble or substantially insoluble in a developer, but turns soluble in the developer under the action of acid, a photoacid generator which generates a sulfonic acid having formula (1) as set forth above, a quencher, and an organic solvent.

Preferably the base resin comprises recurring units of at least one type selected from the general formulae (11) to (15).

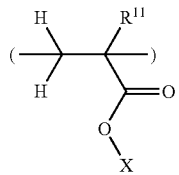
(11)

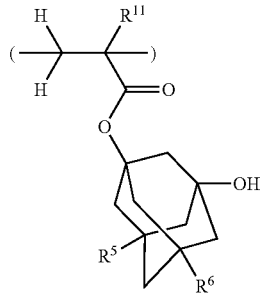
(12)

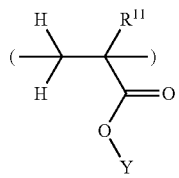
(13)

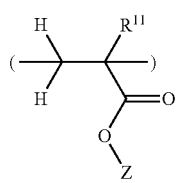
(14)

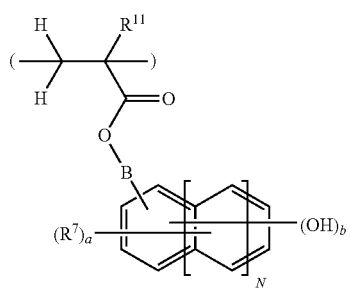
(15)

Herein $R^{11}$ is hydrogen, fluorine, methyl or trifluoromethyl, $R^5$ and $R^6$ are each independently hydrogen or hydroxyl, X is an acid labile group, Y is a substituent group of lactone structure, Z is hydrogen, $C_1$-$C_{15}$ fluoroalkyl or $C_1$-$C_{15}$ fluoroalcohol-containing substituent group, N is an integer of 0 to 2, $R^7$ is hydrogen or $C_1$-$C_{10}$ alkyl group, B is a single bond or a divalent $C_1$-$C_{10}$ organic group which may be substituted with oxygen, a is an integer of 0 to 3, and b is an integer of 1 to 3.

In another aspect, the invention provides a process for forming a pattern comprising the steps of applying the resist composition defined above onto a substrate to form a coating, heat treating the coating and exposing it to high-energy radiation or electron beam through a photomask, and heat treating and developing the exposed coating with a developer.

In one preferred embodiment, the exposing step relies on immersion lithography comprising directing radiation through a projection lens, with a high refractive index liquid having a refractive index of at least 1.0 intervening between the resist coating and the projection lens. In another preferred embodiment, a protective film is coated on the resist coating, and the exposing step relies on immersion lithography comprising directing radiation through a projection lens, with a high refractive index liquid having a refractive index of at least 1.0 intervening between the protective film and the projection lens.

ADVANTAGEOUS EFFECTS OF INVENTION

The PAGs of the invention produce acids which show an adequate acid diffusion behavior since acid diffusion is controlled by a bulky cyclic structure in the sulfonate moiety and an adequate mobility is given due to the presence of a straight-chain hydrocarbon group. The PAGs are fully compatible with resins and other components in resist compositions. The PAGs that generate sulfonic acids perform well without raising problems during the device fabrication process including coating, pre-baking, exposure, post-exposure baking, and developing steps. They solve the problems of resolution, LWR, and exposure latitude. The leach-out of sulfonic acids in water during the ArF immersion lithography is minimized. The influence of water left on the wafer is minimized, restraining defect formation. In the disposal of resist-containing waste liquid after the device fabrication, acyloxy or alkylcarbonate groups at β-position are hydrolyzable under basic conditions so that the sulfonic acids are transformed into less accumulative fluorine compounds of lower molecular weight. In the disposal by combustion, the sulfonic acids are more combustible because of a low degree of fluorine substitution.

DESCRIPTION OF EMBODIMENTS

Figure 1:
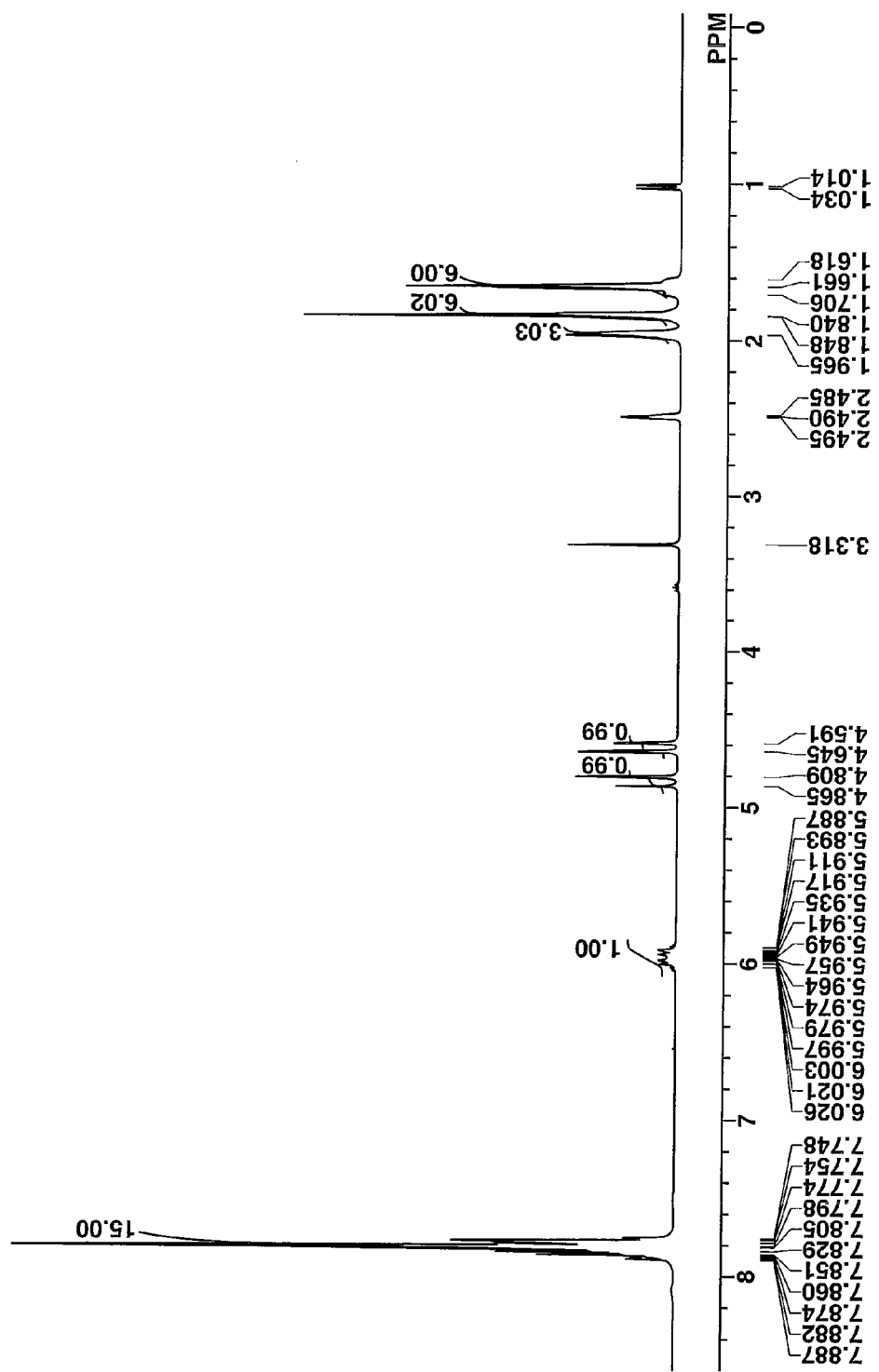
FIG. 1 is a diagram showing the $^1$H-NMR/DMSO-$d_6$ spectrum of PAG-A in Synthesis Example 1-31.

The singular forms "a," "an" and "the" include plural referents unless the context clearly dictates otherwise. The notation (Cn-Cm) means a group containing from n to m carbon atoms per group. PAG stands for photoacid generator.

Photoacid Generator

The photoacid generators of the invention are compounds as typified by sulfonium salts and iodonium salts. These compounds are sensitive to high-energy radiation such as UV, deep-UV, EUV, electron beam, x-ray, excimer laser, gamma-ray and synchrotron radiation and generate sulfonic acids having the general formula (1) in response to high-energy radiation, so that they are useful as photoacid generators in chemically amplified resist compositions.

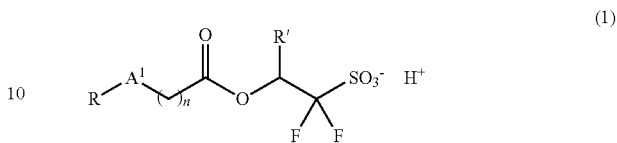

Herein R is a substituted or unsubstituted, monovalent hydrocarbon group having an aromatic ring or alicyclic hydrocarbon structure of at least 5 carbon atoms, R' is hydrogen or trifluoromethyl, $A^1$ is an ester bond, ether bond, thioether bond, amide bond or carbonate bond, and n is an integer of 1 to 3.

In formula (1), R is a substituted or unsubstituted, monovalent hydrocarbon group having an aromatic ring or alicyclic hydrocarbon structure of at least 5 carbon atoms. Suitable substituent groups include polar groups such as carbonyl, hydroxyl and carboxylic acid. By endowing R with a bulky structure and selecting an integer "n" from the range of 1 to 3, that is, interposing an ethylene, propylene or butylene group between the bulky acyl group and the sulfo group, the photoacid generator is given an adequate mobility despite the bulky structure. Then the photoacid generator has an adequate acid diffusibility. Consequently, a resist composition comprising the photoacid generator is improved simultaneously in several properties including resolution, exposure latitude, and LWR and suited for micropatterning. If n=0, the mobility is short and no desired properties are exerted. Values of n which are 4 or greater are impractical because of the unavailability of starting reactants and the difficulty of synthesis. The details of the synthesis method will be described later.

Examples of R include cyclopentyl, cyclohexyl, cycloheptyl, 4-methylcyclohexyl, cyclohexylmethyl, norbornyl, adamantyl, 2-oxocyclopentyl, 2-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, 2-(adamantyl-1-carbonyloxy)-4-oxa-tricyclo[4.2.1.0$^{3,7}$]nonan-5-on-9-yl, 4-oxoadamantyl, phenyl, naphthyl, anthranyl, thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, methylnaphthyl, ethylnaphthyl, methoxynaphthyl, ethoxynaphthyl, dimethylnaphthyl, diethylnaphthyl, dimethoxynaphthyl, diethoxynaphthyl, benzyl, 1-phenylethyl, 2-phenylethyl, and 2-aryl-2-oxoethyl groups such as 2-phenyl-2-oxoethyl, 2-(1-naphthyl)-2-oxoethyl, and 2-(2-naphthyl)-2-oxoethyl.

Preferably R has an adamantyl group because a resist composition comprising the corresponding photoacid generator has so high an acid diffusion inhibitory ability that it may be more improved in resolution and exposure latitude and reduced in LWR at the same time.

Where R further has a polar group such as carbonyl, hydroxyl or carboxylic acid, exposure latitude and LWR are accordingly improved. This is probably because the polar group has an affinity to polar units contained largely in the base resin in the resist composition. As a result, the PAG is uniformly dispersed in the polymer matrix.

$A^1$ is an ester bond (—COO—), ether bond (—O—), thio-ether bond (—S—), amide bond (—CONH—) or carbonate bond (—O—COO—). Preferably $A^1$ is an ester or ether bond.
Examples of the sulfonic acids represented by formula (1) include, but are not limited to, the following.
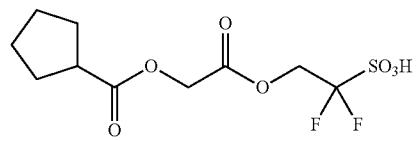
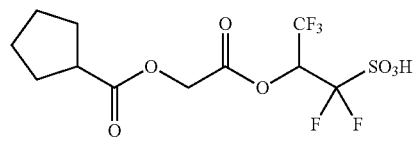
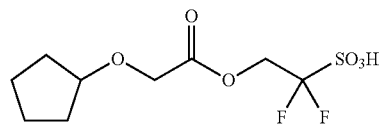
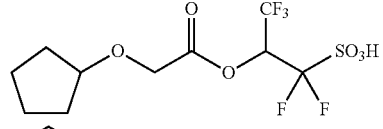
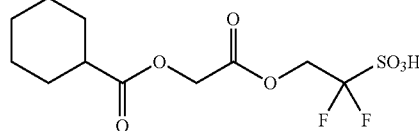
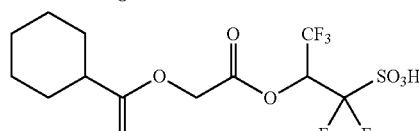
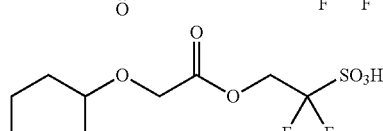
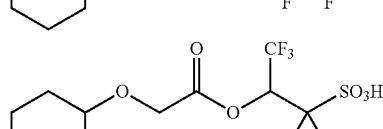
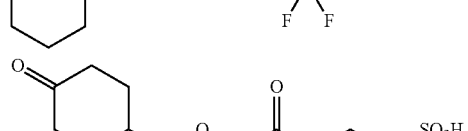
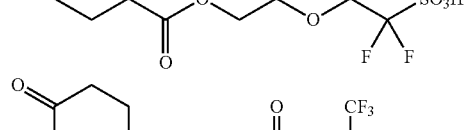
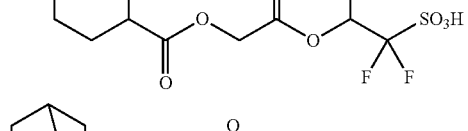
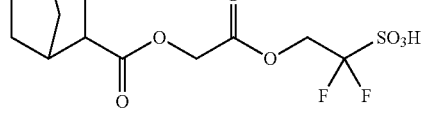
-continued
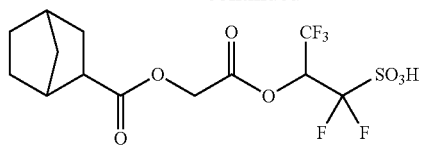
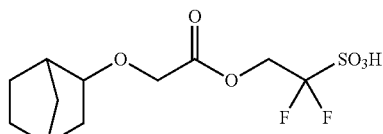
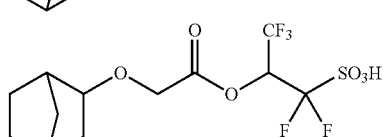
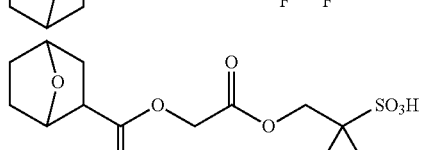
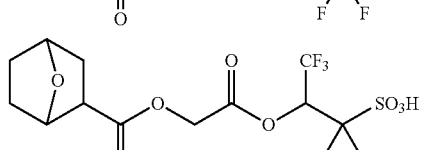
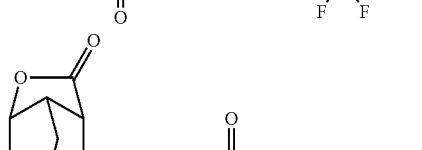
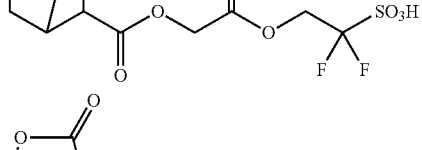
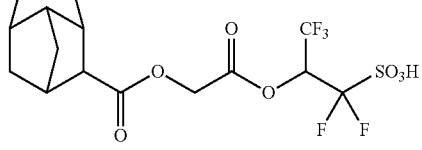
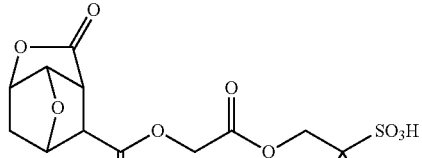
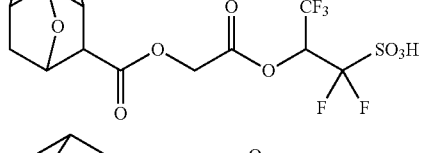
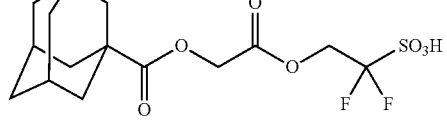

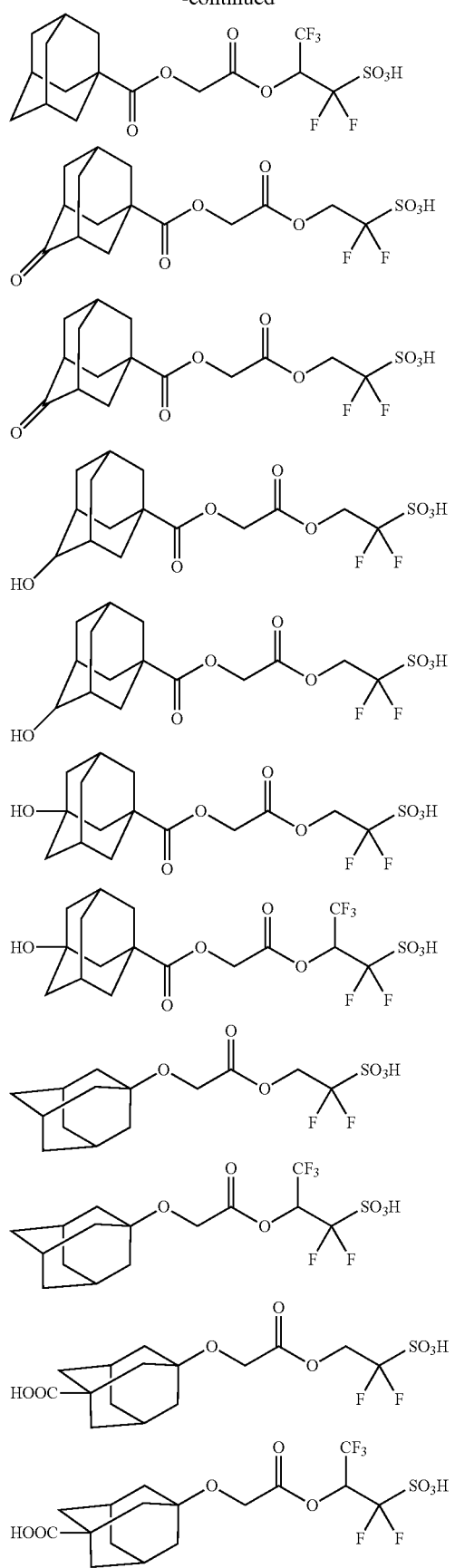
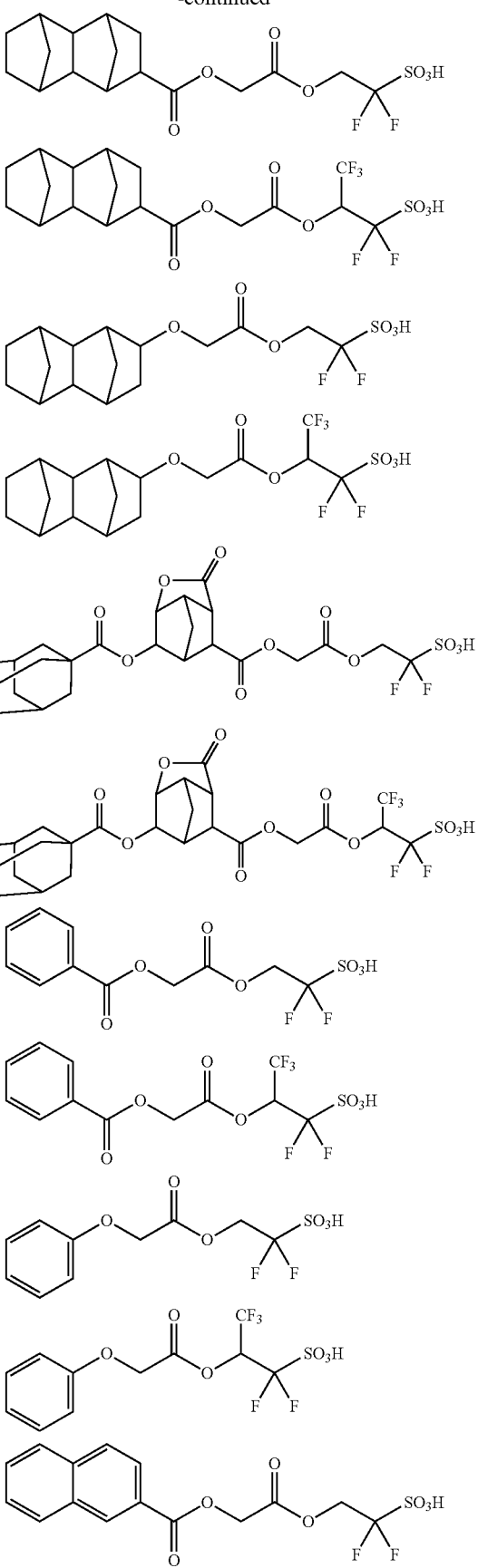

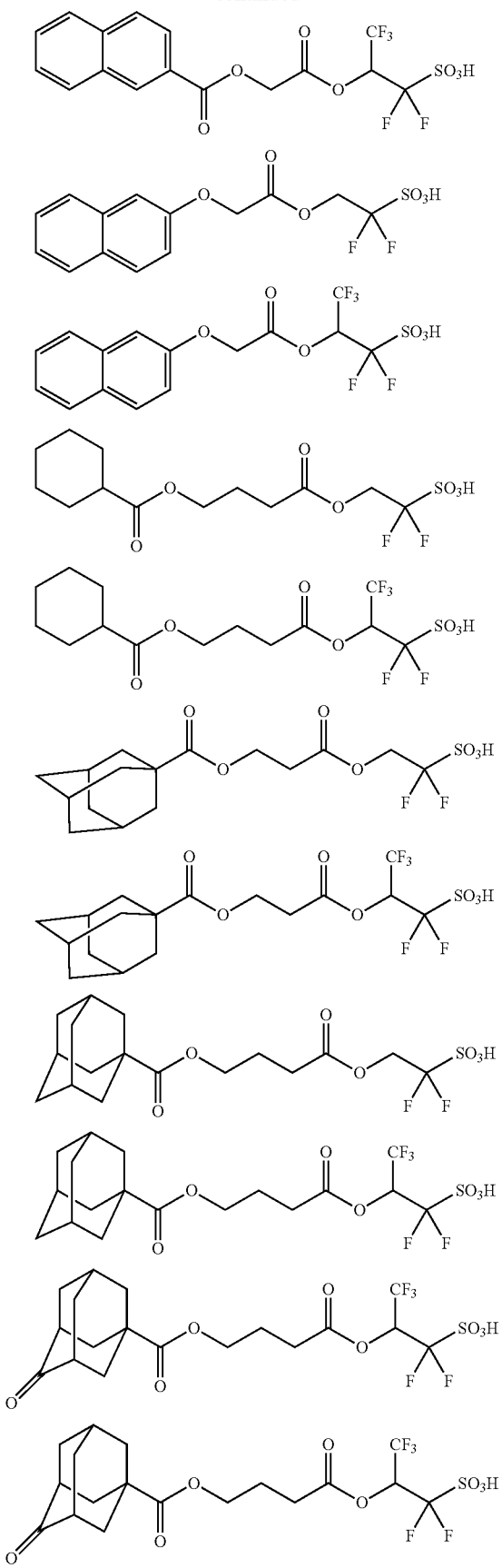

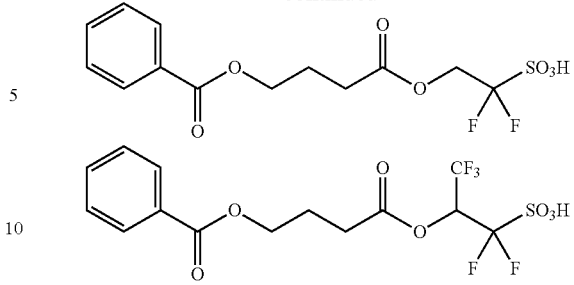

One important feature of the invention is that the structure of R may be readily altered into a variety of structures by the technique to be described later. A high freedom of structural alteration ensures that properties are easily adjusted by alteration of the acyl group. Then a PAG in which R has an optimum structure may be selected in accordance with exposure conditions and the type and composition of the polymer.

Sulfonium Salt

The sulfonium salt of the invention has the general formula (2).

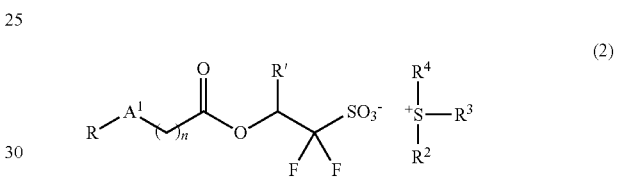

Herein R, $A^1$, n and R' are as defined above, $R^2$, $R^3$, and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom.

In formula (2), R, $A^1$, n and R' are as defined above. $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or any two or more of $R^2$, $R^3$ and $R^4$ may bond together to form a ring with the sulfur atom (in the formula). Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl, and thienyl; 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When two or more of $R^2$, $R^3$ and $R^4$ bond together to form a cyclic structure with the sulfur atom, divalent organic groups such as 1,4-butylene and 3-oxa-1,5-pentylene are exemplary of the cyclic structure-forming group. Also included are aryl groups having polymerizable substituent radicals such as acryloyloxy and methacryloyloxy radicals, and examples of such aryl groups are 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl groups.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 5-phenyldibenzothiophenium, 10-phenylphenoxathiinium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and 4-tert-butoxycarbonylmethyloxyphenyldiphenylsulfonium. Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, (4-acryloyloxy-3,5-dimethylphenyl)diphenylsulfonium, and the like. For these polymerizable sulfonium cations, reference may be made to JP-A H04-230645 and JP-A 2005-084365. These polymerizable sulfonium salts may be used as a monomer in forming a polymer to be described later.

Another embodiment is a sulfonium salt having the general formula (3).

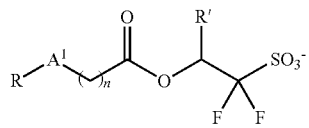

(3)

-continued

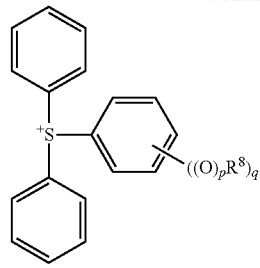

Herein R, $A^1$, n and R' are as defined above, $R^8$ is a substituted or unsubstituted, straight, branched or cyclic $C_1$-$C_{20}$ alkyl or alkenyl group or a substituted or unsubstituted $C_6$-$C_{14}$ aryl group, p is 0 or 1, and q is an integer of 1 to 5.

In formula (3), R, $A^1$, n and R' are as defined above. The substitution position of $R^8$—$(O)_p$— group is not particularly limited, but is preferably 4- or 3-position on the phenyl group, and more preferably 4-position. Examples of groups represented by $R^8$ include methyl, ethyl, n-propyl, sec-propyl, cyclopropyl, n-butyl, sec-butyl, isobutyl, tert-butyl, n-pentyl, cyclopentyl, n-hexyl, cyclohexyl, n-octyl, n-decyl, n-dodecyl, trifluoromethyl, phenyl, 4-methoxyphenyl, and 4-tert-butylphenyl. In the case of p=1, acryloyl, methacryloyl, vinyl, and allyl are exemplary of The letter p is 0 (zero) or 1, and q is an integer of 1 to 5, and preferably 1.

Illustrative examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, (4-n-hexyloxy-3,5-dimethylphenyl)diphenylsulfonium, (4-methacryloyloxy-3,5-dimethylphenyl)diphenylsulfonium, and (4-acryloyloxy-3,5-dimethylphenyl)diphenylsulfonium.

Iodonium Salt

A further embodiment of the invention is a iodonium salt having the general formula (4).

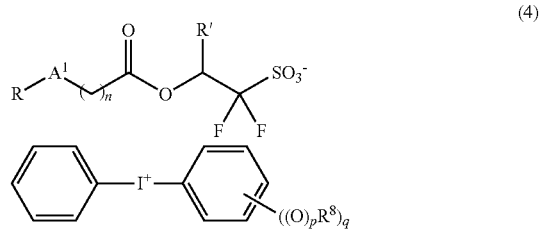

(4)

wherein R, $A^1$, n, R', $R^8$, p and q are as defined above.

In formula (4), R, $A^1$, n, R', $R^8$, p and q are as defined and illustrated above. The substitution position of $R^8$—$(O)_p$— group is not particularly limited, but is preferably 4- or 3-position on the phenyl group, and more preferably 4-position.

Illustrative examples of the iodonium cation include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with the bis(4-tert-butylphenyl)iodonium being preferred.

Described below is how to synthesize the sulfonium salts of formula (2). First reference is made to the synthesis of those sulfonium salts of formula (2) wherein R' is hydrogen. They may be synthesized by starting with triphenylsulfonium 1,1-difluoro-2-hydroxyethanesulfonate.

Described below is how to synthesize triphenylsulfonium 1,1-difluoro-2-hydroxyethanesulfonate. One exemplary compound may be synthesized by reacting 2-bromo-2,2-difluoroethanol with a carboxylic acid chloride to form 2-bromo-2,2-difluoroethyl alkanecarboxylate or 2-bromo-2,2-difluoroethyl arenecarboxylate, converting the bromo group into sodium sulfinate using a sulfur compound such as sodium dithionite, and converting the sulfinic acid into sulfonic acid using an oxidizing agent such as hydrogen peroxide. The outline of the process is illustrated below.

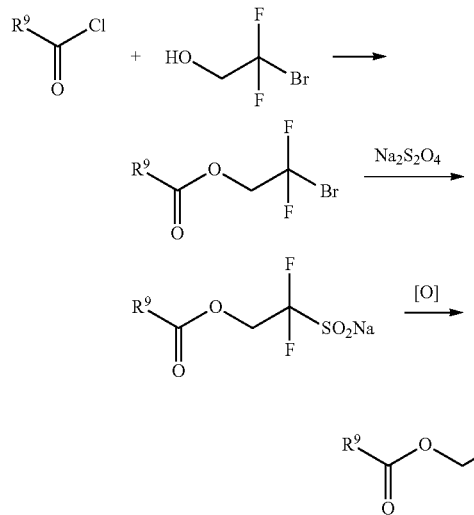

Herein $R^9$ is a straight, branched or cyclic $C_1$-$C_{20}$ alkyl group which may contain a heteroatom.

The steps of esterification, conversion from alkane halide to sodium sulfinate, and conversion to sulfonic acid are well known, while the formulations used in the latter two steps are described in JP-A 2004-002252.

Subsequent ion exchange reaction between the resulting sodium sulfonate and a sulfonium salt compound yields the desired sulfonium salt. With respect to ion exchange reaction, reference is made to JP-A 2007-145797.

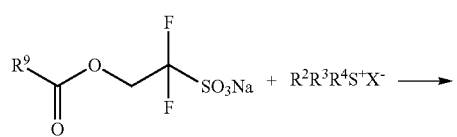

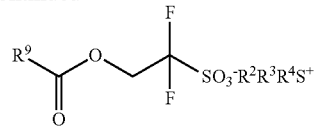

Herein, $R^2$, $R^3$, $R^4$, and $R^9$ are as defined above. $X^-$ is a counter anion. Exemplary anions include, but are not limited to, halide anions such as $I^-$, $Br^-$ and $Cl^-$, sulfuric acid or alkylsulfuric acid anions such as sulfuric acid anion and methylsulfuric acid anion, carboxylic acid anions such as acetate and benzoate, alkanesulfonate anions such as methanesulfonate and propanesulfonate, arenesulfonate anions such as benzenesulfonate and p-toluenesulfonate, and hydroxide.

Further, the acyl group $R^9CO$— introduced as above is subjected to ester hydrolysis or solvolysis, completing the synthesis of triphenylsulfonium 1,1-difluoro-2-hydroxyethane-sulfonate. The outline of the process is illustrated below.

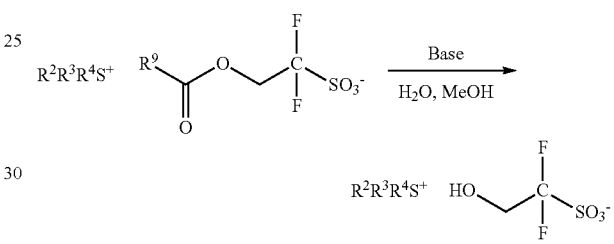

Note that $R^2$, $R^3$, $R^4$, and $R^9$ are as defined above, and Me is methyl.

This formulation ensures possible introduction from 1,1-difluoro-2-hydroxyethanesulfonate even when $R^9$ is a substituent group which is unstable under the conditions of the previous anion synthesis process (conversion of a bromo group into sodium sulfinate using a sulfur compound such as sodium dithionite and subsequent conversion of sulfinic acid into sulfonic acid using an oxidizing agent such as hydrogen peroxide).

The sulfonium salts of formula (3) and the iodonium salts of formula (4) may be similarly synthesized.

The starting sulfonium and iodonium salts may be synthesized according to the teachings of The Chemistry of Sulfonium Group Part 1, John-Wiley & Sons (1981), Advanced Photochemistry, vol. 17, John-Wiley & Sons (1992), J. Org. Chem., 1988, 53, 5571-5573, JP-A H08-311018, JP-A H09-15848, JP-A 2001-122850, JP-A H07-25846, JP-A 2001-181221, JP-A 2002-193887, and JP-A 2002-193925. An onium cation having an acryloyloxy or methacryloyloxy group as a polymerizable substituent group may be synthesized according to the methods of JP-A H04-230645 and JP-A 2005-84365, by reacting a hydroxyphenyldiphenylsulfonium halide (preformed) with acryloyl chloride or methacryloyl chloride under basic conditions.

A photoacid generator of formula (2) may be synthesized by reacting triphenylsulfonium 1,1-difluoro-2-hydroxyethane-sulfonate, synthesized as above, with an carboxylic acid halide having the general formula (5):

R-A$^1$-(CH$_2$)$_n$—COCX$^1$ (5)

wherein R, A$^1$ and n are as defined above, and X$^1$ is a halogen atom, under basic conditions.

Alternatively, a compound having formula (2) wherein $A^1$ is an ester bond or ether bond may be synthesized by reacting triphenylsulfonium 1,1-difluoro-2-hydroxyethanesulfonate with a chloroalkylcarboxylic acid halide under basic conditions, to form 2-(haloalkylcarbonyloxy)-1,1-difluoro-2-hydroxyethane-sulfonate, and further reacting it with a compound having the general formula (6):

wherein R is as defined above, M is lithium, sodium or potassium, and m is 0 or 1.

Next the synthesis of those sulfonium salts of formula (2) wherein R' is trifluoromethyl is described. Once triphenylsulfonium 1,1,3,3,3-pentafluoro-2-hydroxypropane-sulfonate is synthesized instead of triphenylsulfonium 1,1-difluoro-2-hydroxyethanesulfonate, the same procedure as used where R' is hydrogen is followed, whereby a photoacid generator of formula (2) wherein R' is trifluoromethyl is synthesized. With respect to the synthesis of triphenylsulfonium 1,1,3,3,3-pentafluoro-2-hydroxypropane-sulfonate, reference may be made to JP-A 2007-145804.

While the methods for the synthesis of the photoacid generators of formula (1) have been described, they are merely exemplary of the synthesis method and are not intended to limit the invention thereto.

As described above, a first embodiment of the present invention provides a photoacid generator for chemically amplified resist compositions which generates a sulfonic acid having formula (1) upon exposure to high-energy radiation. A second embodiment of the present invention provides a sulfonium salt and iodonium salt serving as photoacid generators in chemically amplified resist compositions. A third embodiment of the present invention provides a resist composition comprising a photoacid generator which generates a sulfonic acid having formula (1) upon exposure to high-energy radiation and a resin which changes its solubility in an alkaline developer liquid under the action of acid. The resist composition may be either positive or negative, with a positive resist composition being preferred from the standpoint of resolution or the like.

Resist Composition

The positive resist composition is defined herein as comprising, in addition to a PAG capable of generating a sulfonic acid having formula (1), (A) a base resin which changes its solubility in an alkaline developer liquid under the action of acid,
(B) an organic solvent, and optionally,
(C) an acid generator other than the inventive PAG,
(D) a quencher, and
(E) a surfactant.

The negative resist composition is defined herein as comprising, in addition to a PAG capable of generating a sulfonic acid having formula (1), (A') a base resin which is soluble in an alkaline developer,
(B) an organic solvent, and optionally,
(C) an acid generator other than the inventive PAG,
(D) a quencher,
(E) a surfactant, and
(F) a crosslinker which induces crosslinkage under the action of acid.

These components are described in detail.

In the resist composition, the inventive PAG is specifically compounded in an amount of 0.1 to 80 parts, more specifically 1 to 40 parts by weight per 100 parts by weight of the base resin (A) or (A'). Too much amounts of the PAG may give rise to problems such as degradation of resolution and foreign particles during development or resist removal. It is noted that parts by weight per 100 parts by weight of the resin is often abbreviated as "phr".

Component (A) is a base resin which changes its solubility in an alkaline developer liquid under the action of acid. The base resin for use in chemically amplified positive resist compositions may be a polymer comprising recurring units of at least one type selected from the following general formulae (11) to (15).

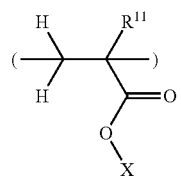

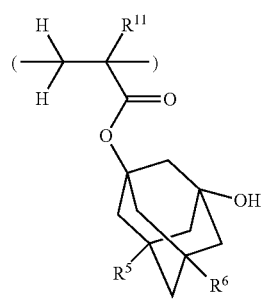

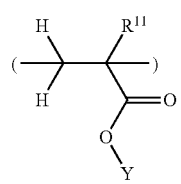

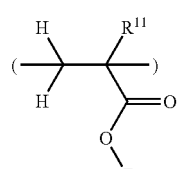

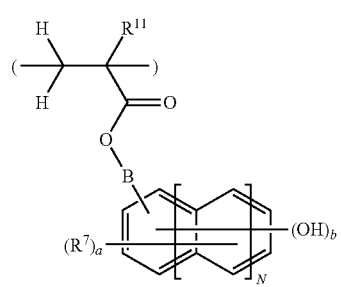

Herein $R^{11}$ is hydrogen, fluorine, methyl or trifluoromethyl, $R^5$ and $R^6$ are each independently a hydrogen atom or hydroxyl group, X is an acid labile group, Y is a lactone structure-containing substituent group, Z is hydrogen, a $C_1$-$C_{15}$ fluoroalkyl group or a $C_1$-$C_{15}$ fluoroalcohol-containing substituent group, N is an integer of 0 to 2, $R^7$ is a hydrogen atom or $C_1$-$C_{10}$ alkyl group, B is a single bond or a divalent organic group, typically $C_1$-$C_{10}$ alkylene, which may have oxygen substituted thereon, a is an integer of 0 to 3, and b is an integer of 1 to 3.

Under the action of an acid, a polymer comprising recurring units of formula (11) is decomposed to generate a carboxylic acid and turns into an alkali-soluble polymer.

The acid labile group represented by X may be selected from a variety of such groups, for example, groups of the following general formulae (L1) to (L4) and (L2-2), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

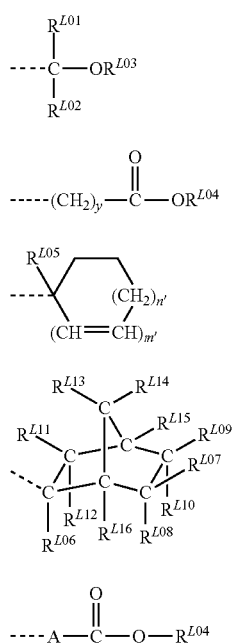

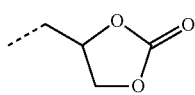

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L2-2), $R^{L04}$ is as defined above, and examples of the moiety of the formula:

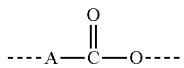

are given below.

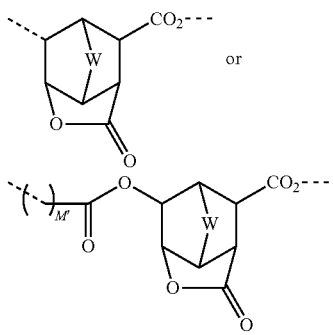

Herein the broken line indicates a valence bond, W is an oxygen atom or $CH_2$, and M' is an integer of 1 to 3.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m' is 0 or 1, n' is 0, 1, 2 or 3, and 2 m'+n' is equal to 2 or 3.

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the substituted alkyl groups are shown below.

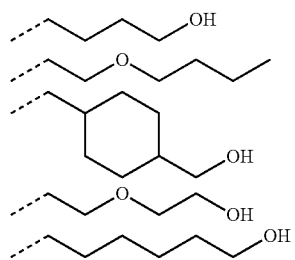

In formula (L4), $R^{L06}$ is a substituted or unsubstituted, $C_1$-$C_8$ straight, branched or cyclic alkyl group or a substituted or unsubstituted $C_6$-$C_2$, aryl group. Examples of these groups are the same as exemplified for $R^{L05}$. $R^{L07}$ to $R^{L16}$ independently represent hydrogen or monovalent $C_1$-$C_1$, hydrocarbon groups. Exemplary hydrocarbon groups are straight, branched or cyclic alkyl groups such as methyl, ethyl, propyl, isopropyl, n-butyl, sec-butyl; tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

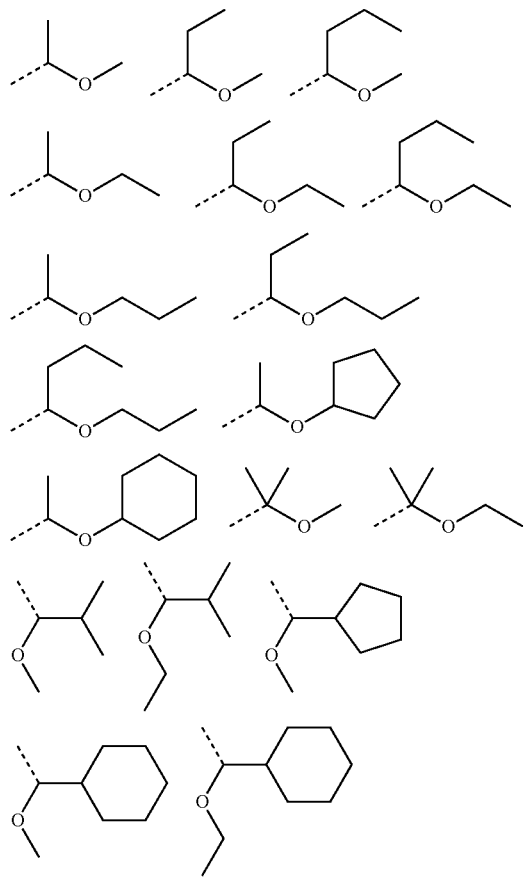

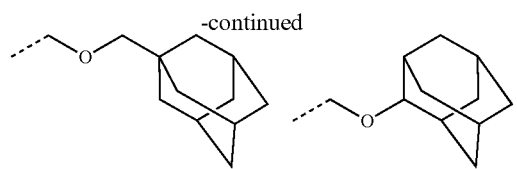

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L2-2) include 9-(tert-butyloxycarbonyl)-5-oxo-4-oxatricyclo[4.2.1.0$^{3,7}$]-nonan-2-yl, 9-(tert-amyloxycarbonyl)-5-oxo-4-oxatricyclo[4.2.1.0$^{3,7}$]nonan-2-yl, 9-(2-(adamantan-1-yl)propan-2-yloxycarbonyl)-5-oxo-4-oxatricyclo[4.2.1.0$^{3,7}$]nonan-2-yl, 9-(1-ethylcyclopentyloxycarbonyl)-5-oxo-4-oxatricyclo-[4.2.1.0$^{3,7}$]nonan-2-yl, 9-(1-butylcyclopentyloxycarbonyl)-5-oxo-4-oxatricyclo-[4.2.1.0$^{3,7}$]nonan-2-yl, 9-(1-ethylcyclohexyloxycarbonyl)-5-oxo-4-oxatricyclo-[4.2.1.0$^{3,7}$]nonan-2-yl, 9-(1-butylcyclohexyloxycarbonyl)-5-oxo-4-oxatricyclo-[4.2.1.0$^{3,7}$]nonan-2-yl, 9-(2-methyl-2-adamantyloxycarbonyl)-5-oxo-4-oxatricyclo-[4.2.1.0$^{3,7}$]nonan-2-yl, 9-(2-ethyl-2-adamantyloxycarbonyl)-5-oxo-4-oxatricyclo-[4.2.1.0$^{3,7}$]nonan-2-yl, 9-(4-ethyltetracyclo[6.2.1.1$^{3,6}$.0$^{2,7}$]dodecan-4-yloxycarbonyl)-5-oxo-4-oxatricyclo[4.2.1.0$^{3,7}$]nonan-2-yl, 2-(9-(tert-butyloxycarbonyl)-5-oxo-4-oxatricyclo[4.2.1.0$^{3,7}$]-nonan-2-yloxy)-2-oxoethyl, 2-(9-(tert-amyloxycarbonyl)-5-oxo-4-oxatricyclo[4.2.1.0$^{3,7}$]-nonan-2-yloxy)-2-oxoethyl, 2-(9-(2-(adamantan-1-yl)propan-2-yloxycarbonyl)-5-oxo-4-oxatricyclo[4.2.1.0$^{3,7}$]nonan-2-yloxy)-2-oxoethyl, 2-(9-(1-ethylcyclopentyloxycarbonyl)-5-oxo-4-oxatricyclo-[4.2.1.0$^{3,7}$]nonan-2-yloxy)-2-oxoethyl, 2-(9-(1-butylcyclopentyloxycarbonyl)-5-oxo-4-oxatricyclo-[4.2.1.0$^{3,7}$]nonan-2-yloxy)-2-oxoethyl, 2-(9-(1-ethylcyclohexyloxycarbonyl)-5-oxo-4-oxatricyclo-[4.2.1.0$^{3,7}$]nonan-2-yloxy)-2-oxoethyl, 2-(9-(1-butylcyclohexyloxycarbonyl)-5-oxo-4-oxatricyclo-[4.2.1.0$^{3,7}$]nonan-2-yloxy)-2-oxoethyl, 2-(9-(2-methyl-2-adamantyloxycarbonyl)-5-oxo-4-oxatricyclo-[4.2.1.0$^{3,7}$]nonan-2-yloxy)-2-oxoethyl, 2-(9-(2-ethyl-2-adamantyloxycarbonyl)-5-oxo-4-oxatricyclo-[4.2.1.0$^{3,7}$]nonan-2-yloxy)-2-oxoethyl, 2-(9-(4-ethyltetracyclo[6.2.1.1$^{3,6}$.0$^{2,7}$]dodecan-4-yloxy-carbonyl)-5-oxo-4-oxatricyclo[4.2.1.0$^{3,7}$]nonan-2-yloxy)-2-oxoethyl, 4-(9-(tert-butyloxycarbonyl)-5-oxo-4-oxatricyclo[4.2.1.0$^{3,7}$]-nonan-2-yloxy)-4-oxobutyl, 4-(9-(tert-amyloxycarbonyl)-5-oxo-4-oxatricyclo[4.2.1.0$^{3,7}$]-nonan-2-yloxy)-4-oxobutyl, 4-(9-(2-(adamantan-1-yl)propan-2-yloxycarbonyl)-5-oxo-4-oxatricyclo[4.2.1.0$^{3,7}$]nonan-2-yloxy)-4-oxobutyl, 4-(9-(1-ethylcyclopentyloxycarbonyl)-5-oxo-4-oxatricyclo-[4.2.1.0$^{3,7}$]nonan-2-yloxy)-4-oxobutyl, 4-(9-(1-butylcyclopentyloxycarbonyl)-5-oxo-4-oxatricyclo-[4.2.1.0$^{3,7}$]nonan-2-yloxy)-4-oxobutyl, 4-(9-(1-ethylcyclohexyloxycarbonyl)-5-oxo-4-oxatricyclo-[4.2.1.0$^{3,}$ 7]nonan-2-yloxy)-4-oxobutyl, 4-(9-(1-butylcyclohexyloxycarbonyl)-5-oxo-4-oxatricyclo-[4.2.1.0$^{3,7}$]nonan-2-yloxy)-4-oxobutyl, 4-(9-(2-methyl-2-adamantyloxycarbonyl)-5-oxo-4-oxatricyclo-[4.2.1.0$^{3,7}$]nonan-2-yloxy)-4-oxobutyl, 4-(9-(2-ethyl-2-adamantyloxycarbonyl)-5-oxo-4-oxatricyclo-[4.2.1.0$^{3,7}$]nonan-2-yloxy)-4-oxobutyl, 4-(9-(4-ethyltetracyclo[6.2.1.1$^{3,6}$.0$^{2,7}$]dodecan-4-yloxy-carbonyl)-5-oxo-4-oxatricyclo[4.2.1.0$^{3,7}$]nonan-2-yloxy)-4-oxobutyl, etc.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are more preferred.

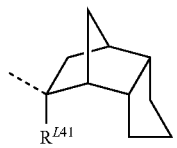

(L4-1)

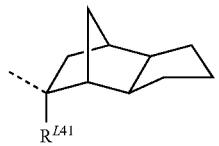

(L4-2)

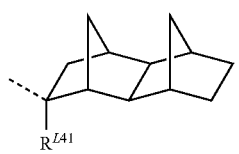

(L4-3)

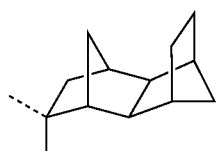

(L4-4)

In formulae (L4-1) to (L4-4), the broken line denotes a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

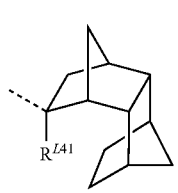

(L4-3-1)

(L4-3-2)

Similarly, the general formula (L4-4) represents one or a mixture of two or more selected from groups having the following general formulas (L4-4-1) to (L4-4-4).

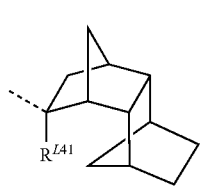

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

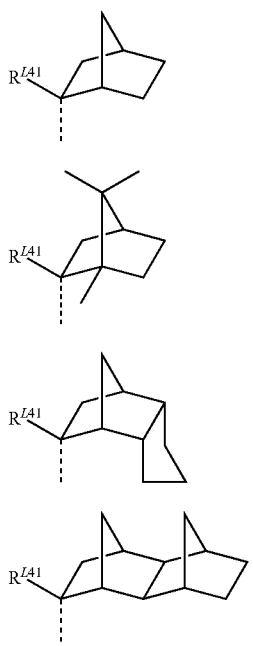

(L4-1-endo)
(L4-2-endo)
(L4-3-endo)
(L4-4-endo)

Illustrative examples of the acid labile group of formula (L4) are given below, but not limited thereto.

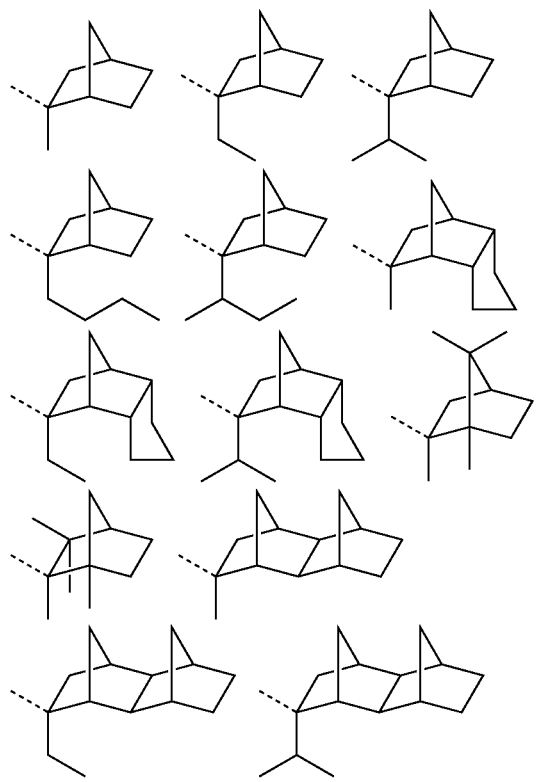

Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.

Illustrative, non-limiting examples of the recurring units of formula (11) are given below. Although only (meth)acrylates are illustrated, those which are separated by a divalent linking group of formula (L2) or (L2-2) are also useful.

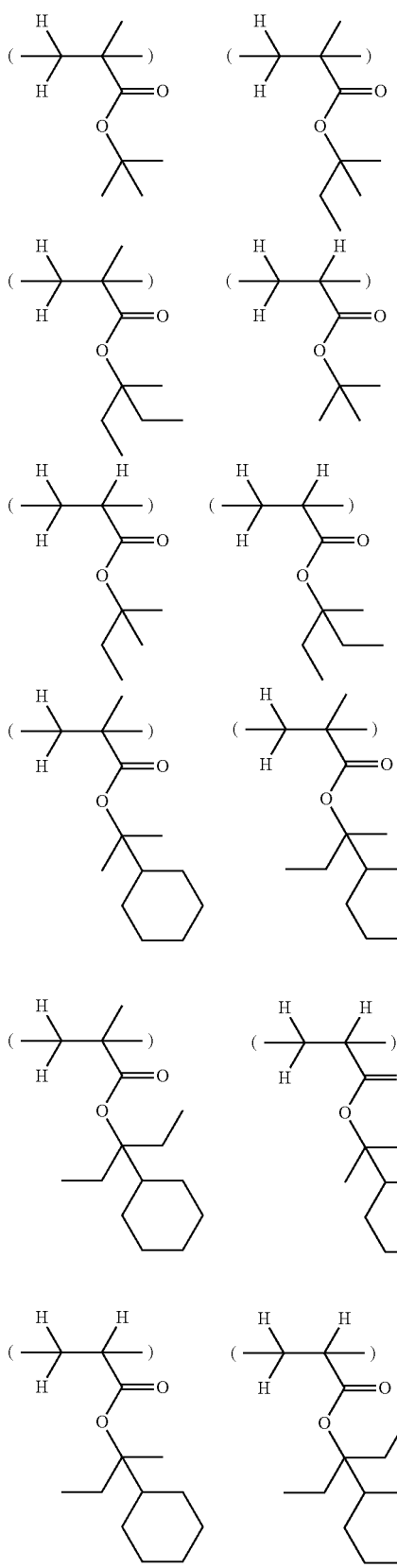

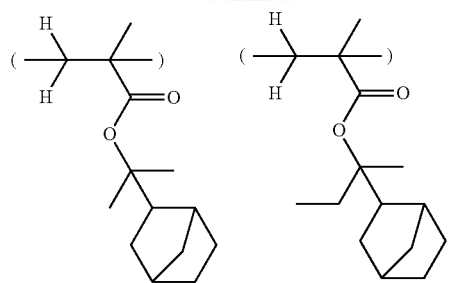
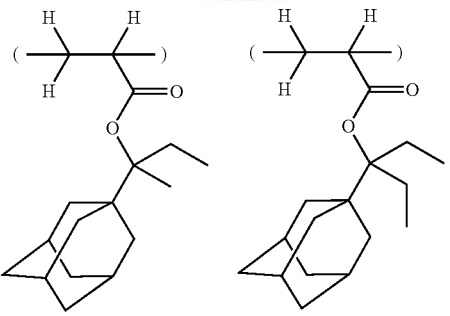
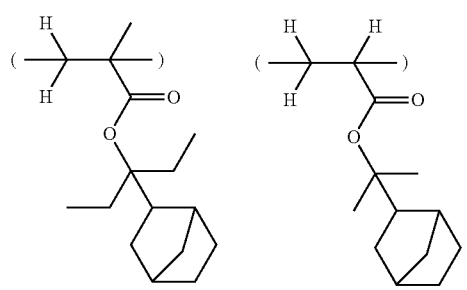
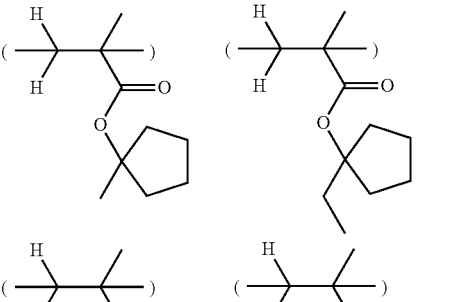
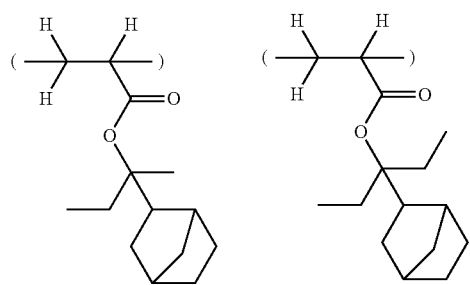
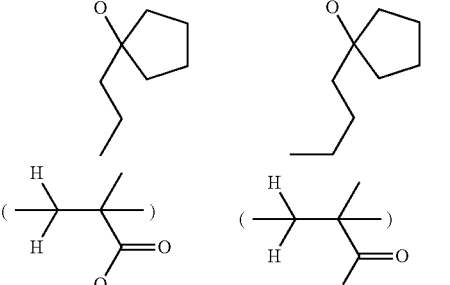
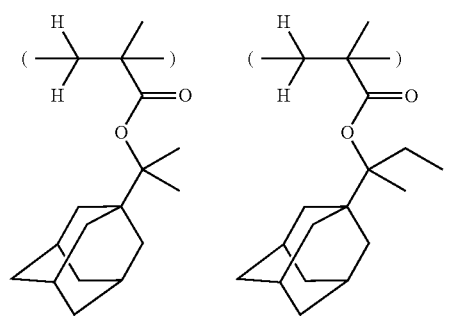
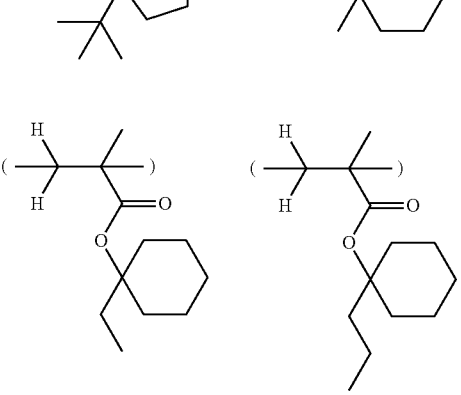
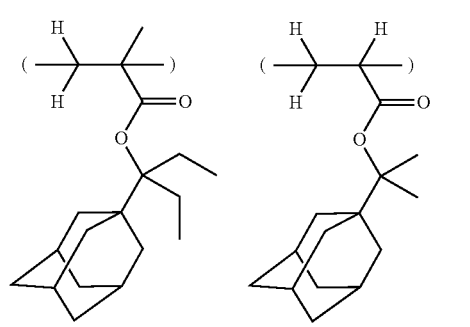
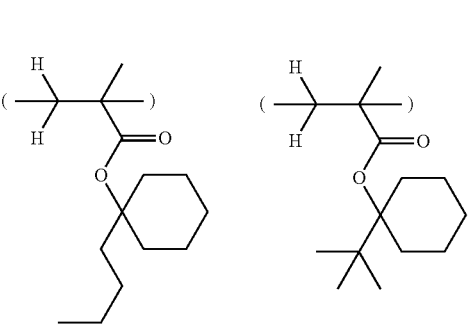

-continued
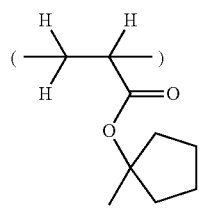 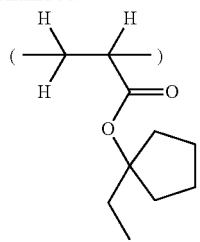
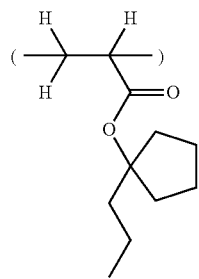 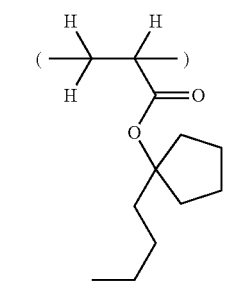
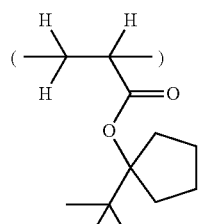 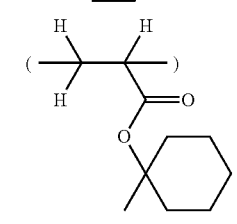
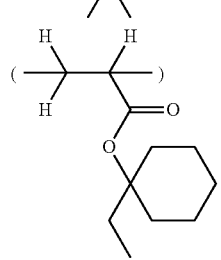 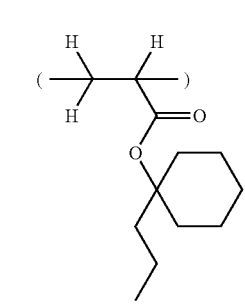
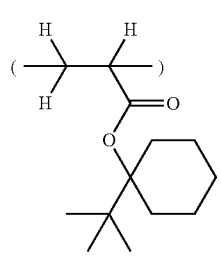 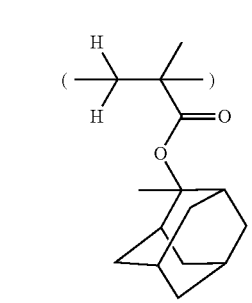
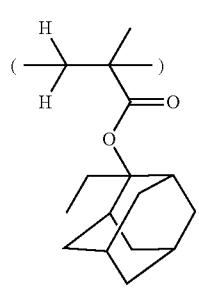 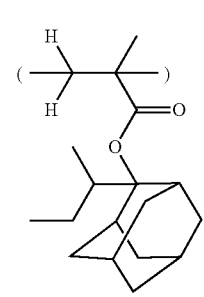
-continued
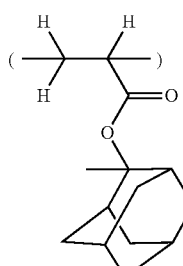 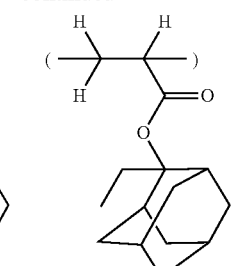
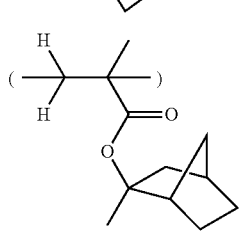 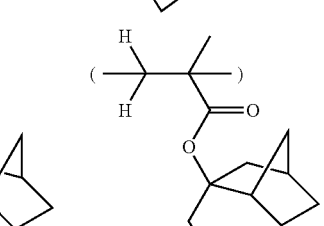
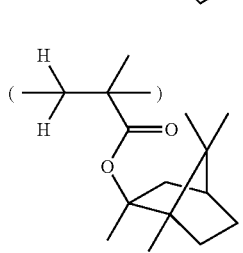 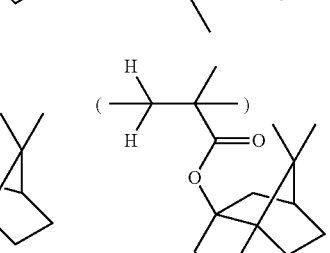
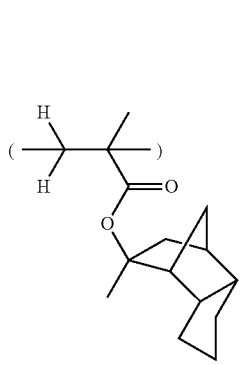 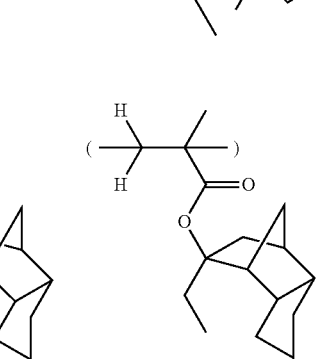
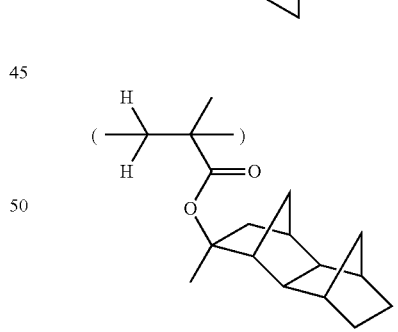
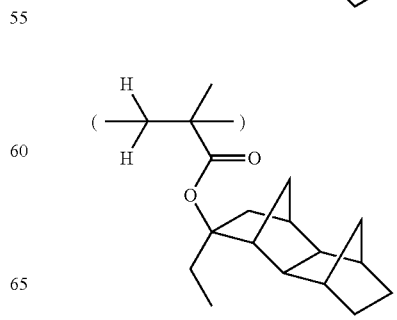

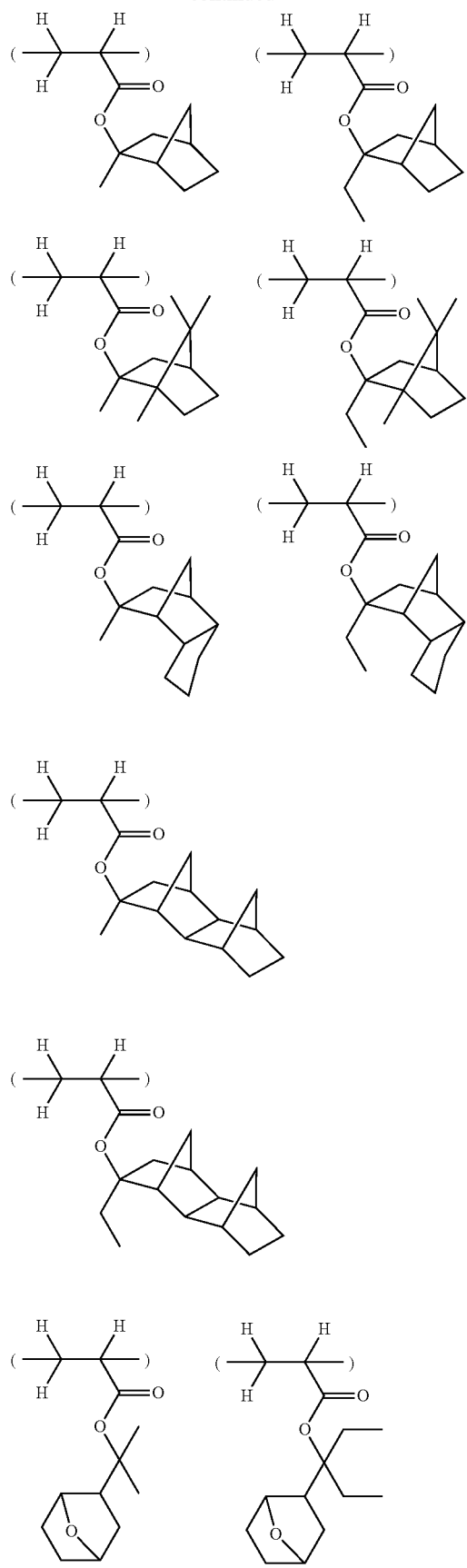
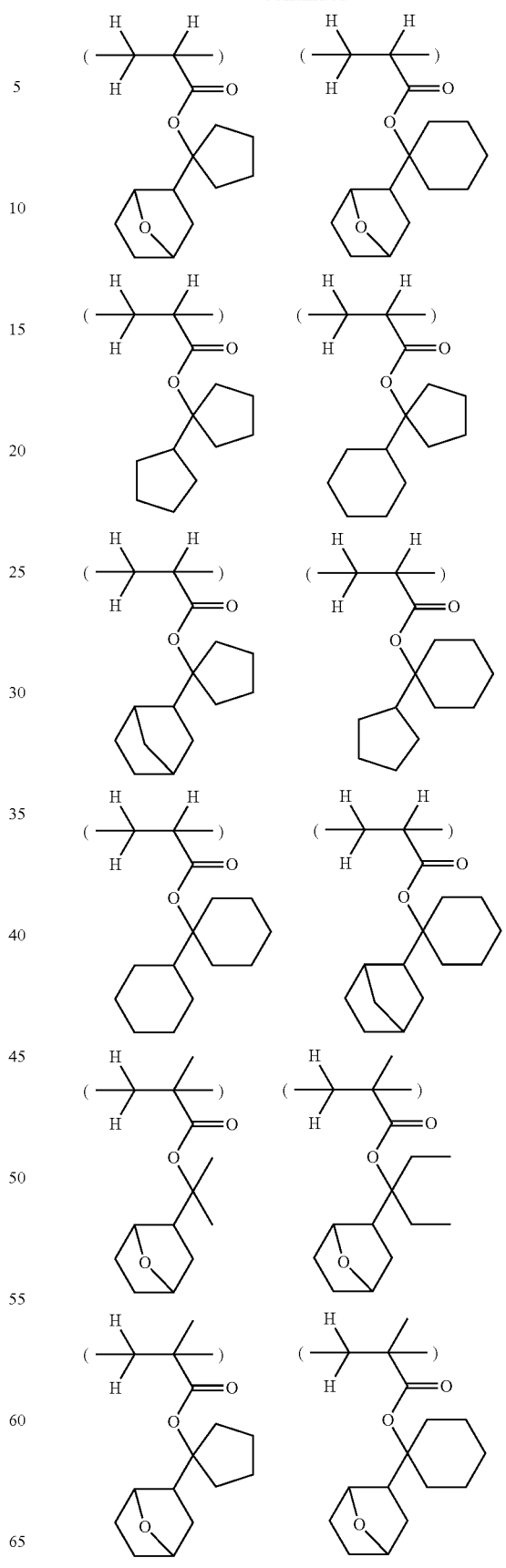

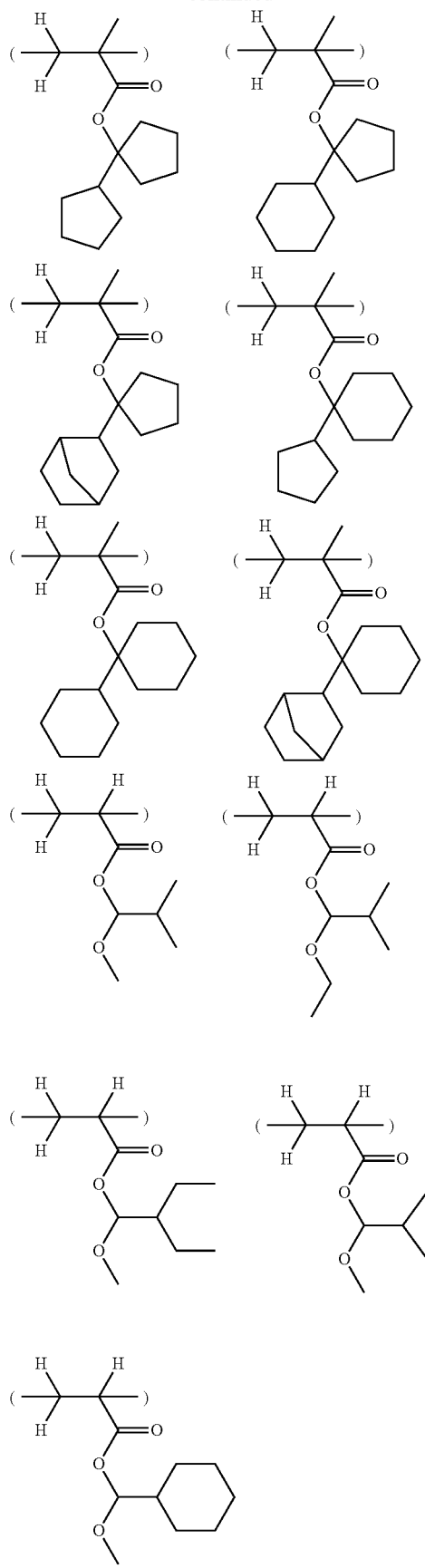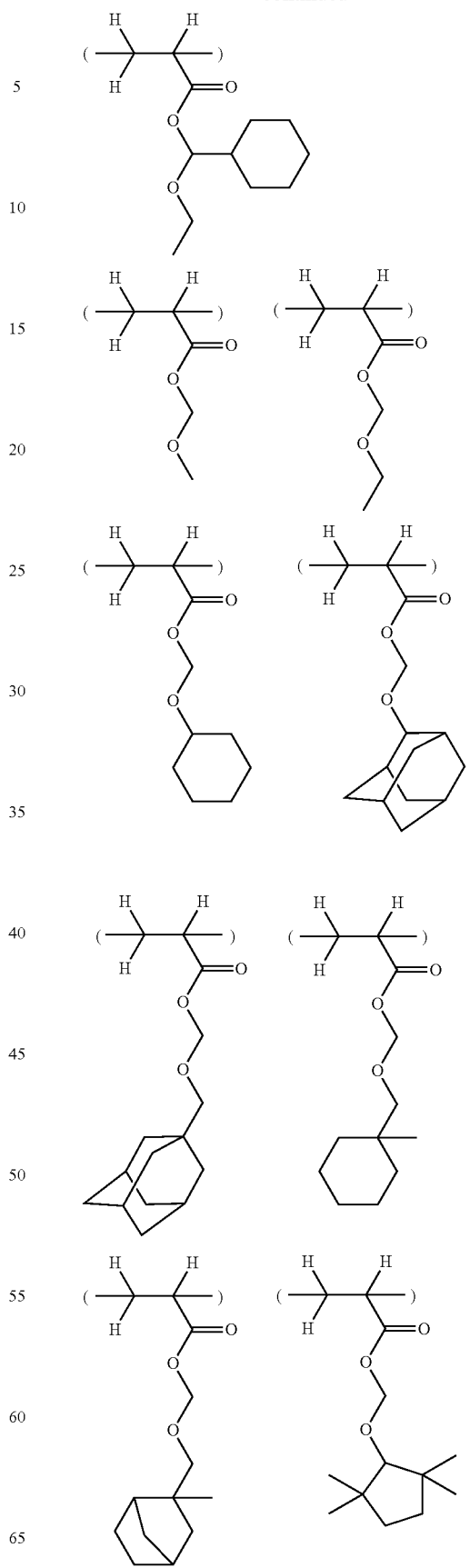

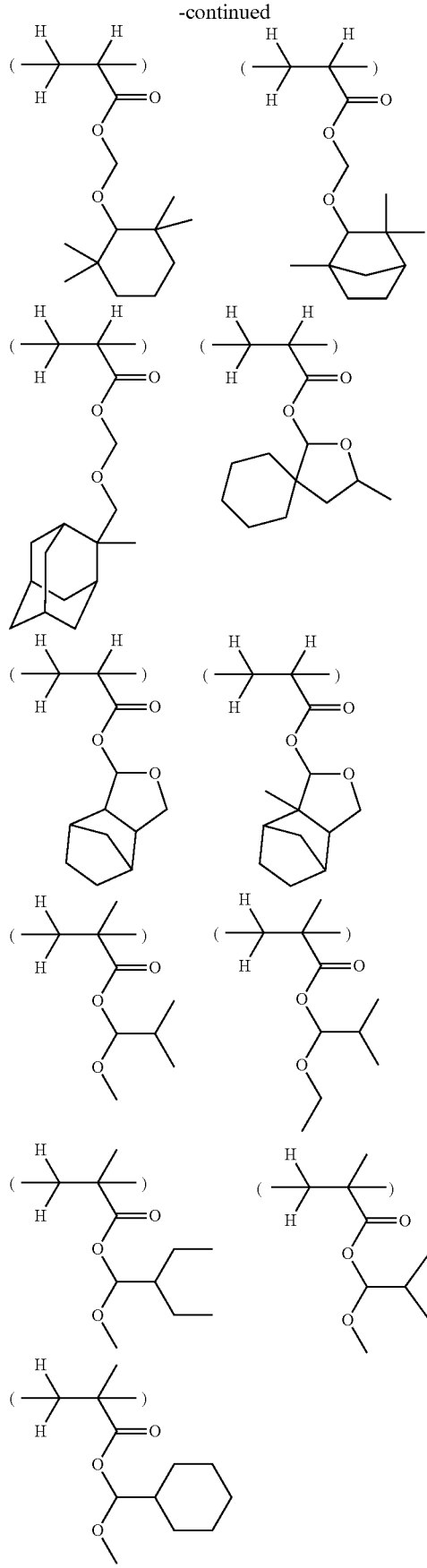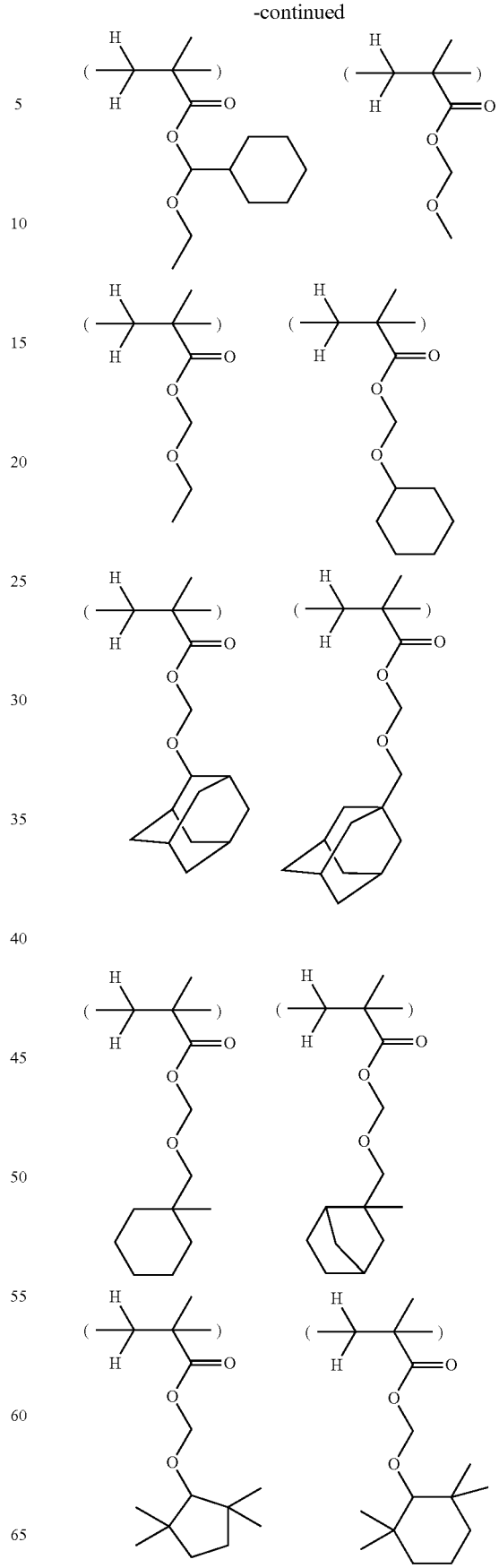

-continued

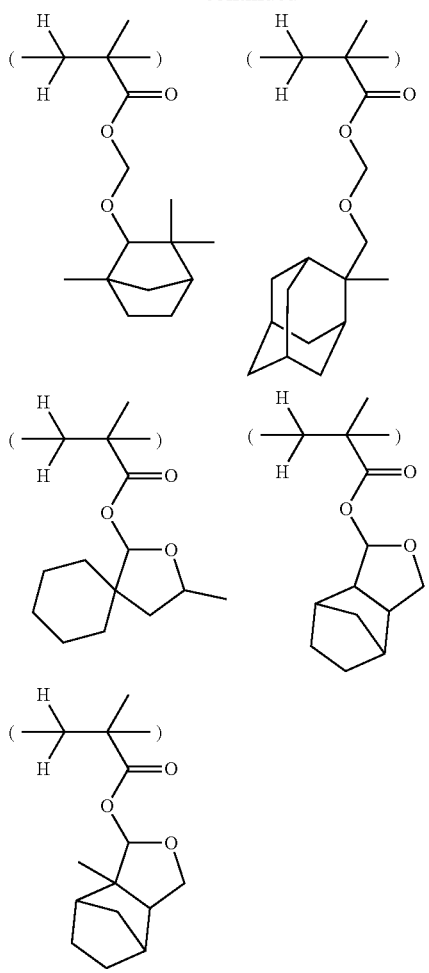

Illustrative, non-limiting examples of the recurring units of formula (12) are given below.

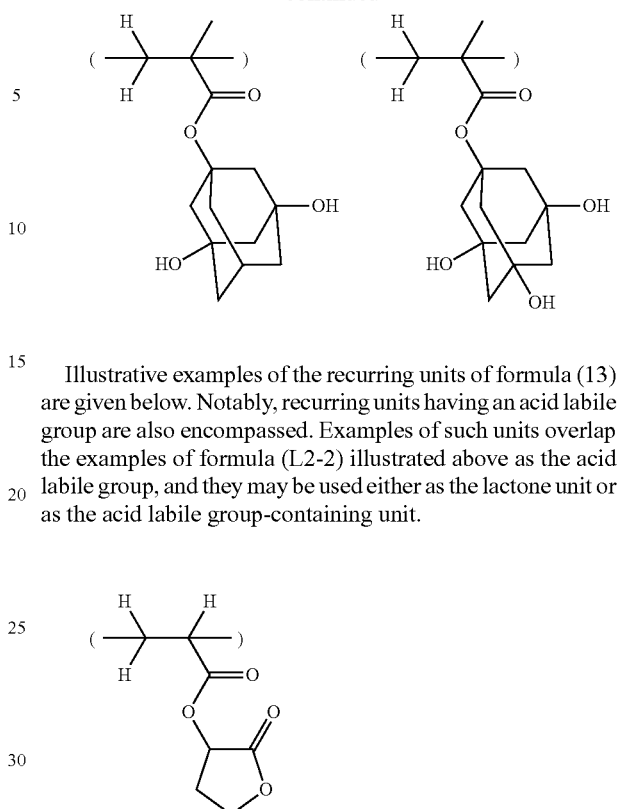

Illustrative examples of the recurring units of formula (13) are given below. Notably, recurring units having an acid labile group are also encompassed. Examples of such units overlap the examples of formula (L2-2) illustrated above as the acid labile group, and they may be used either as the lactone unit or as the acid labile group-containing unit.

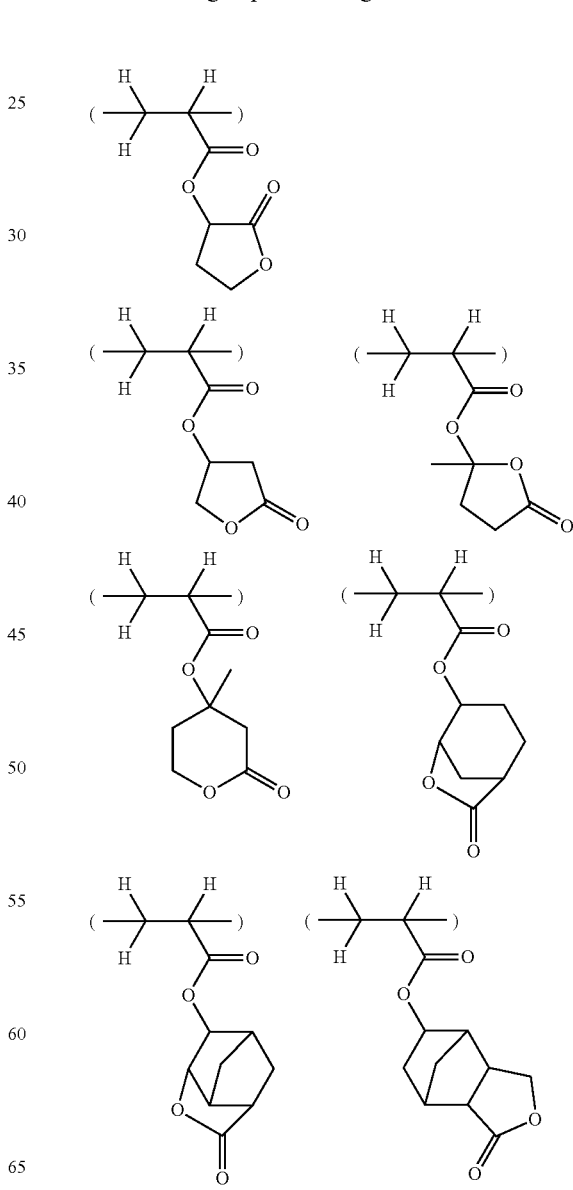

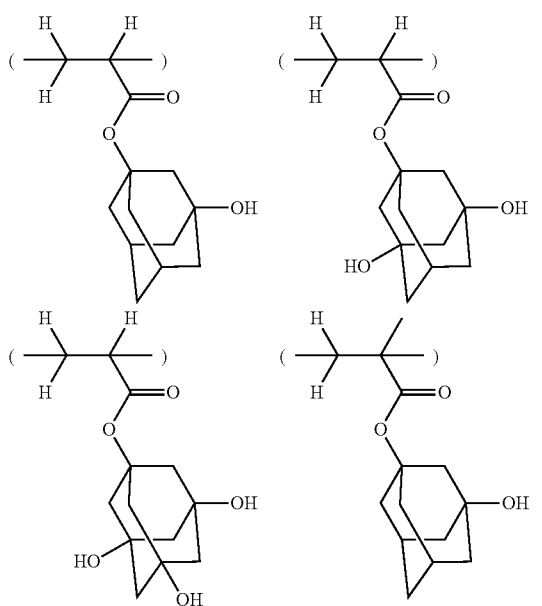

41
-continued
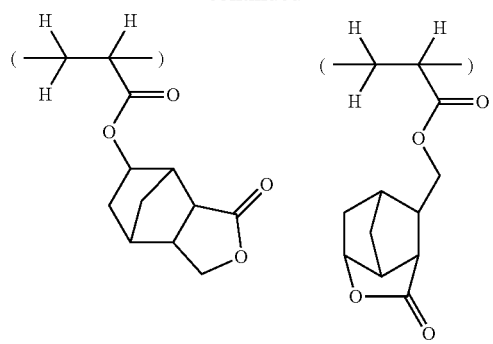
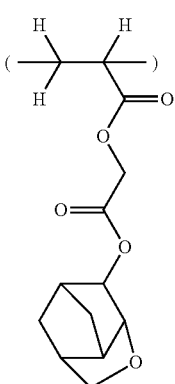
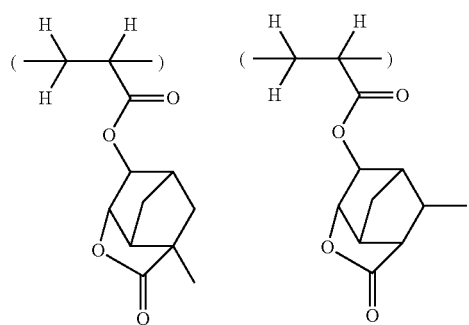
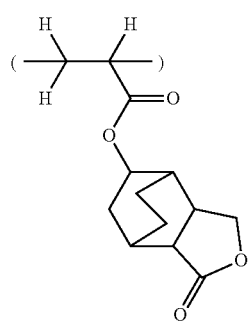
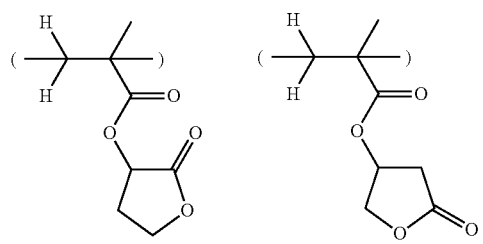
42
-continued
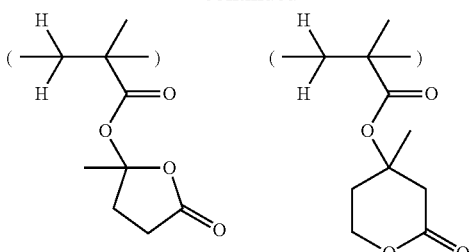
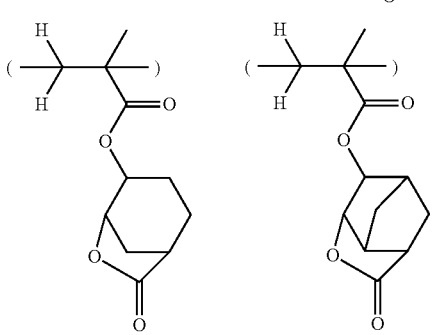
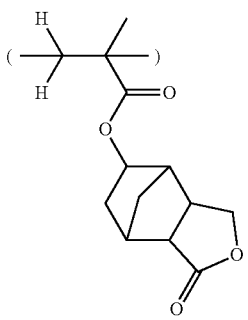
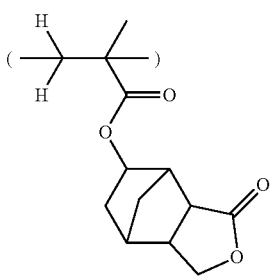
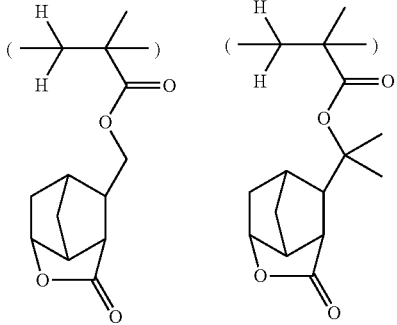

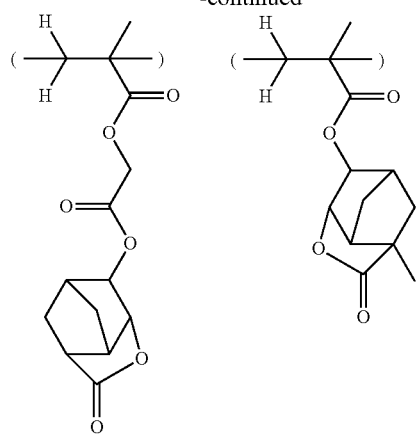
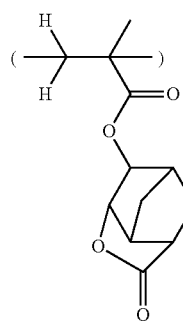
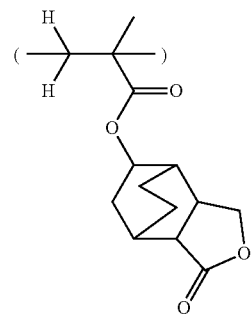
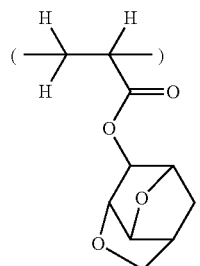
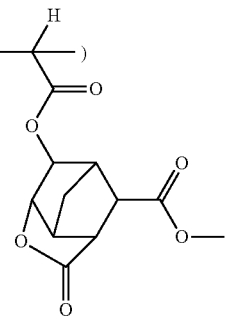
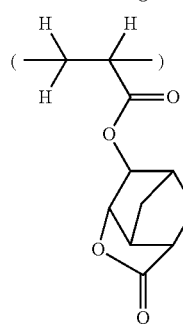
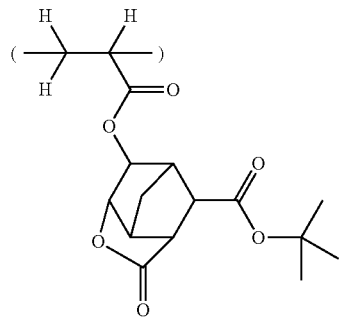
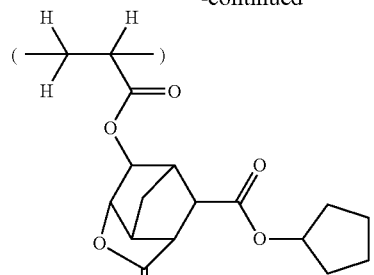
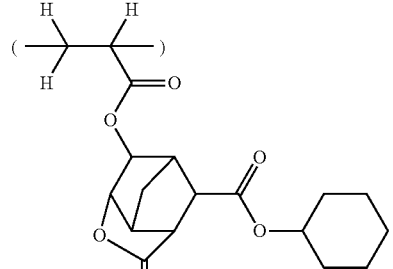
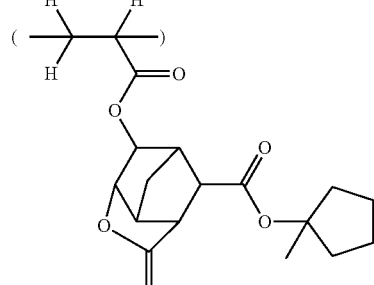
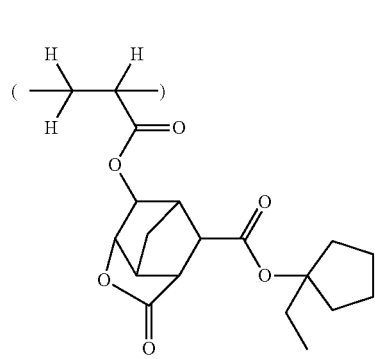
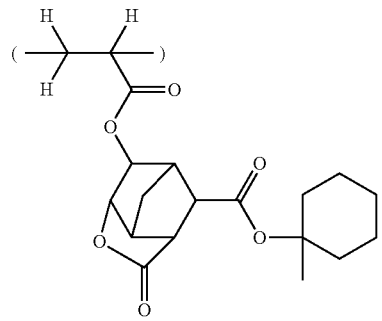

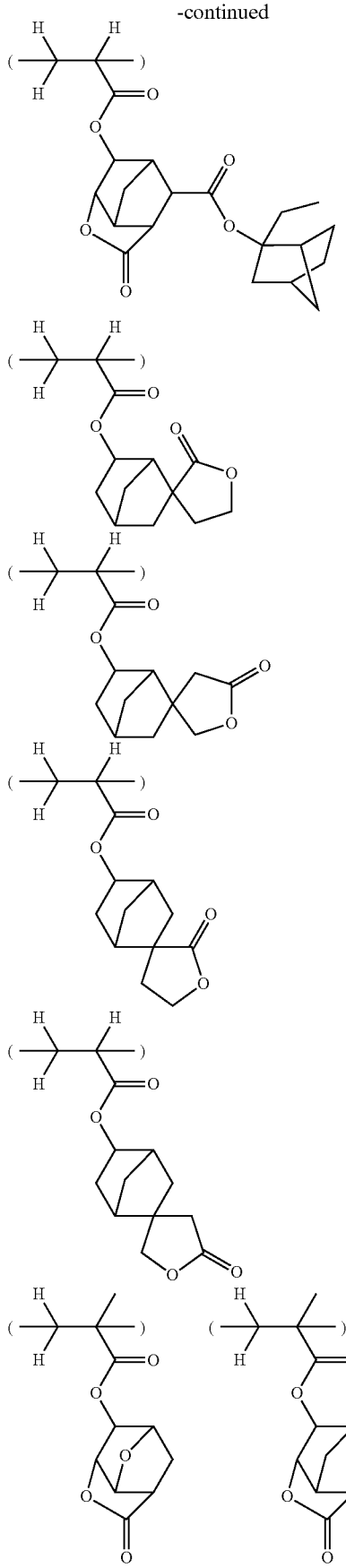
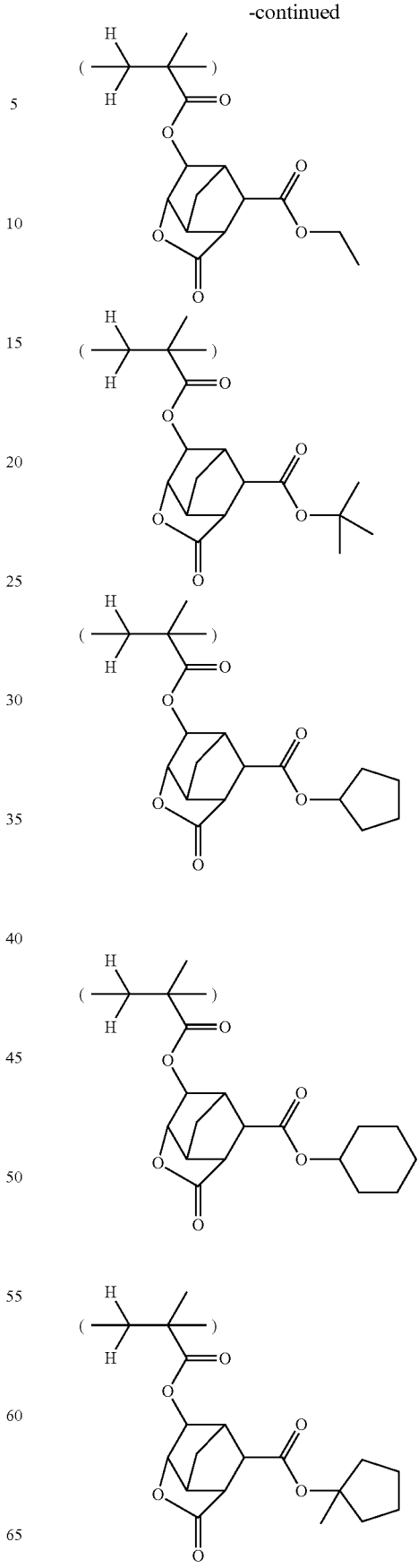

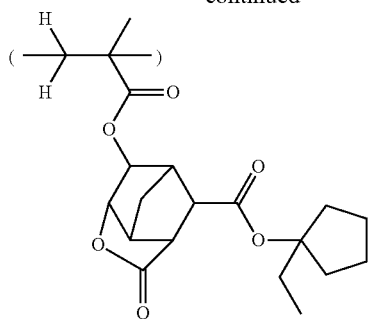

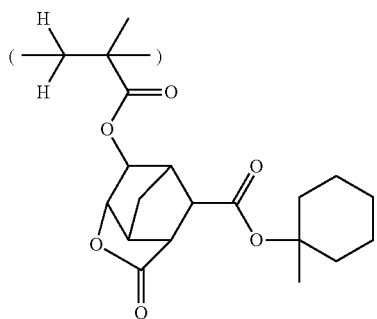

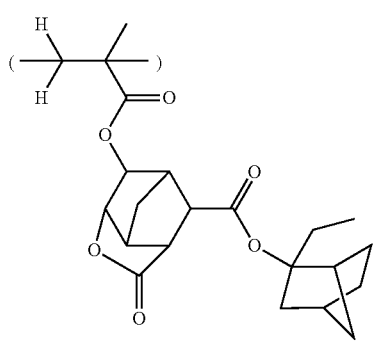

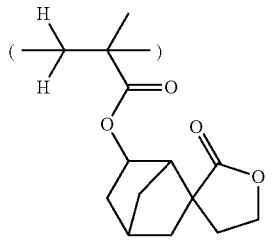

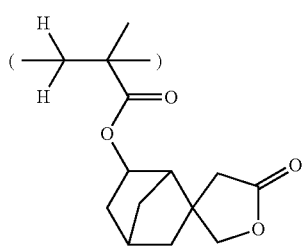

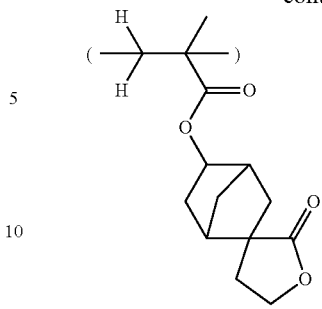

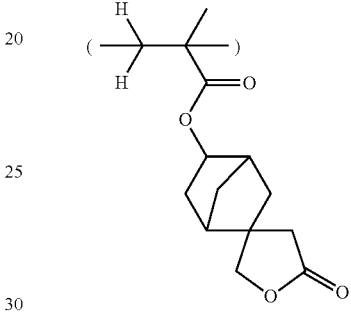

Also, units of the general formula (5L-1) may be advantageously used.

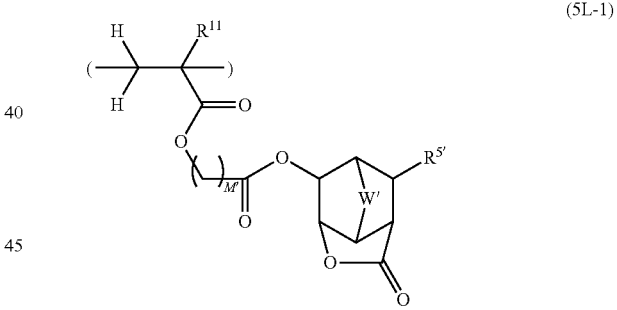

(5L-1)

In formula (5L-1), $R^{11}$ is hydrogen, fluorine, methyl or trifluoromethyl, and preferably methyl. $R^{5'}$ is hydrogen or $CO_2R^{5''}$ wherein $R^{5''}$ is hydrogen, halogen or a straight, branched or cyclic $C_1$-$C_{15}$ monovalent hydrocarbon group which may have oxygen. W' is $CH_2$, O or S. M' is an integer of 1 to 3.

Examples of $R^{5''}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, and methoxyethoxyethyl, as well as the groups shown below.

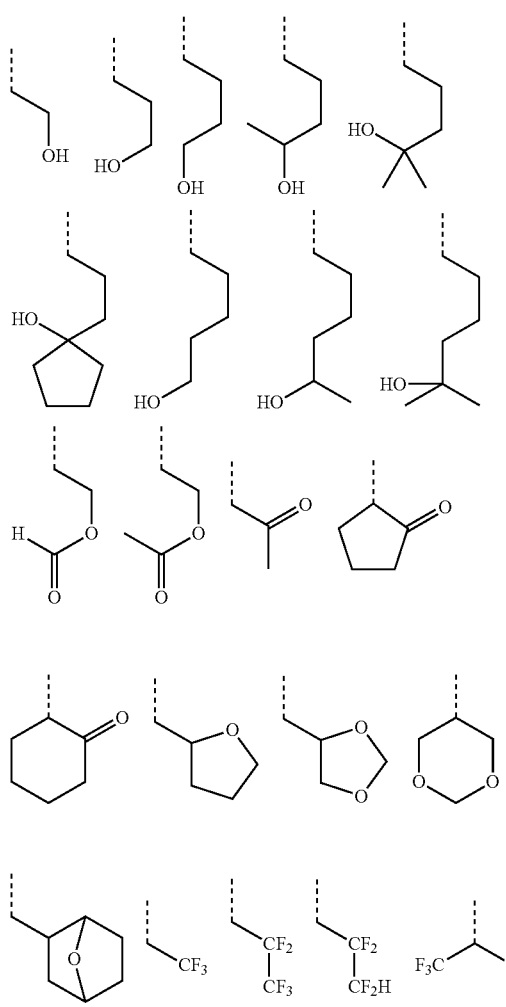

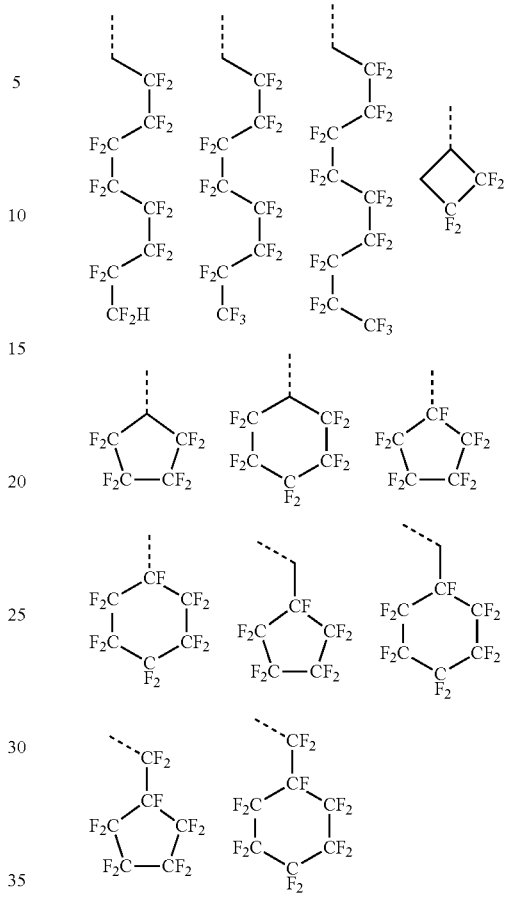

(The Broken Line Denotes a Valence Bond.)

Preferred examples of $R^{5''}$ include methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-ethyltetracyclo[6.2.1.1$^{3,6}$.0$^{2,7}$]dodecan-4-yl. Preferably W' is $CH_2$.

Examples of suitable monomers from which recurring units of formula (5L-1) are derived are given below.

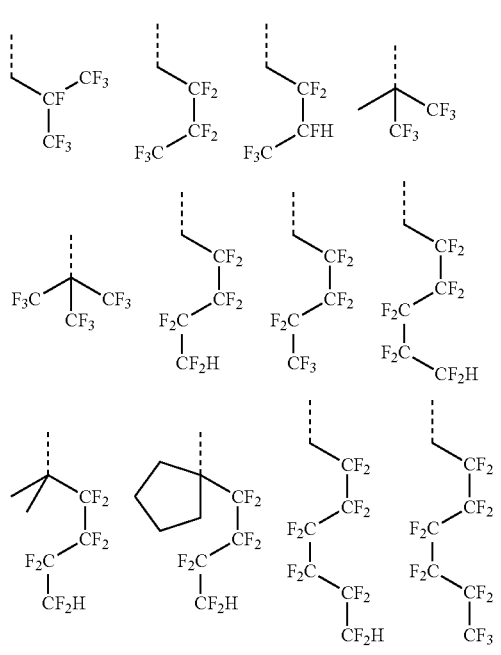

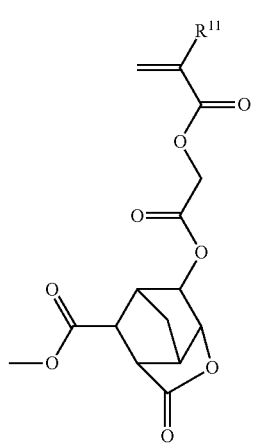

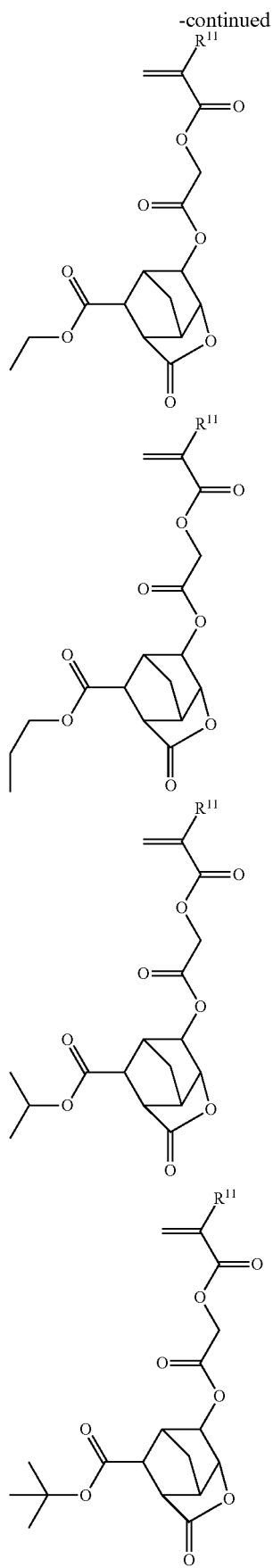
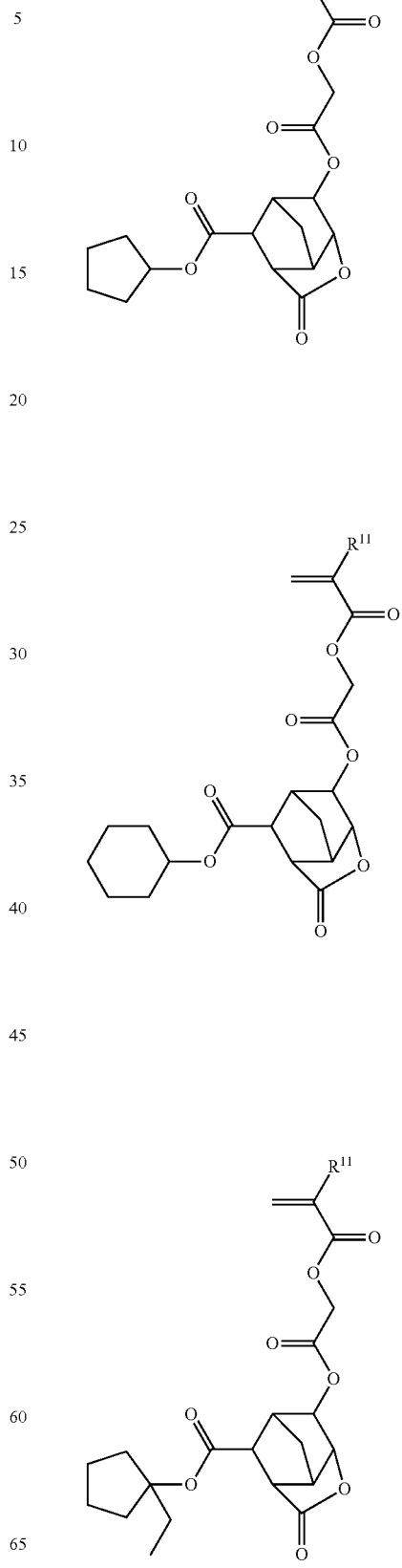

53
-continued
54
-continued
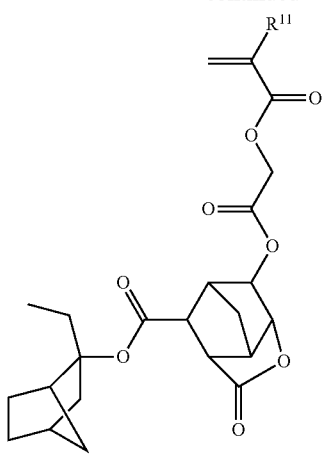
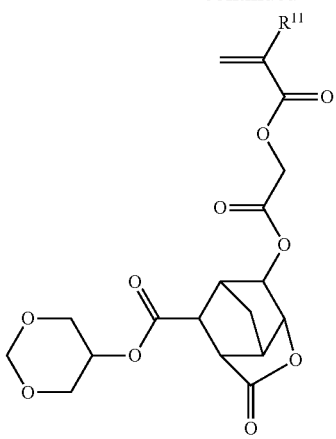
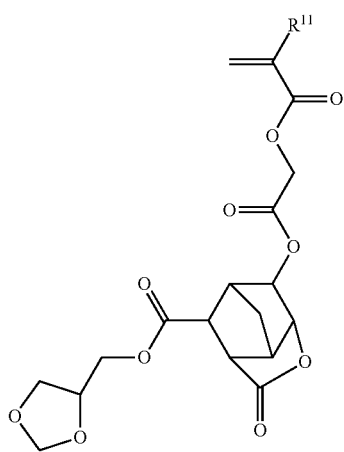

55
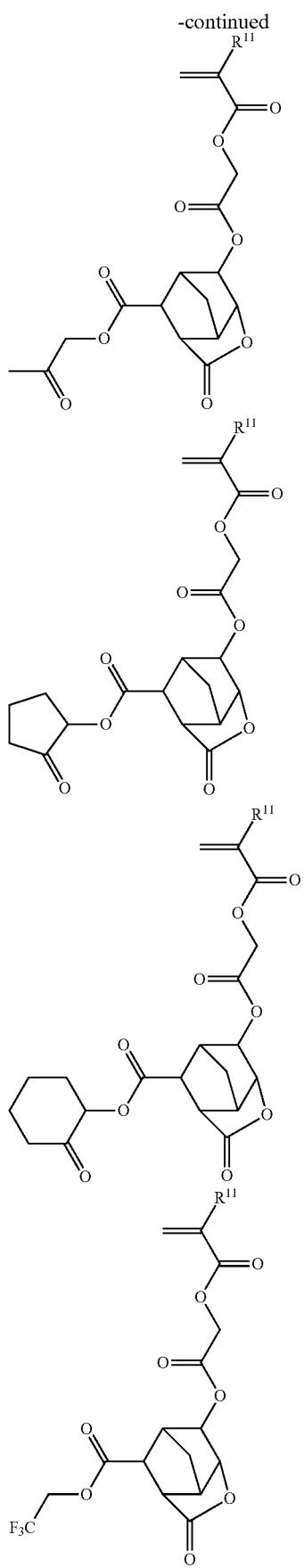
56
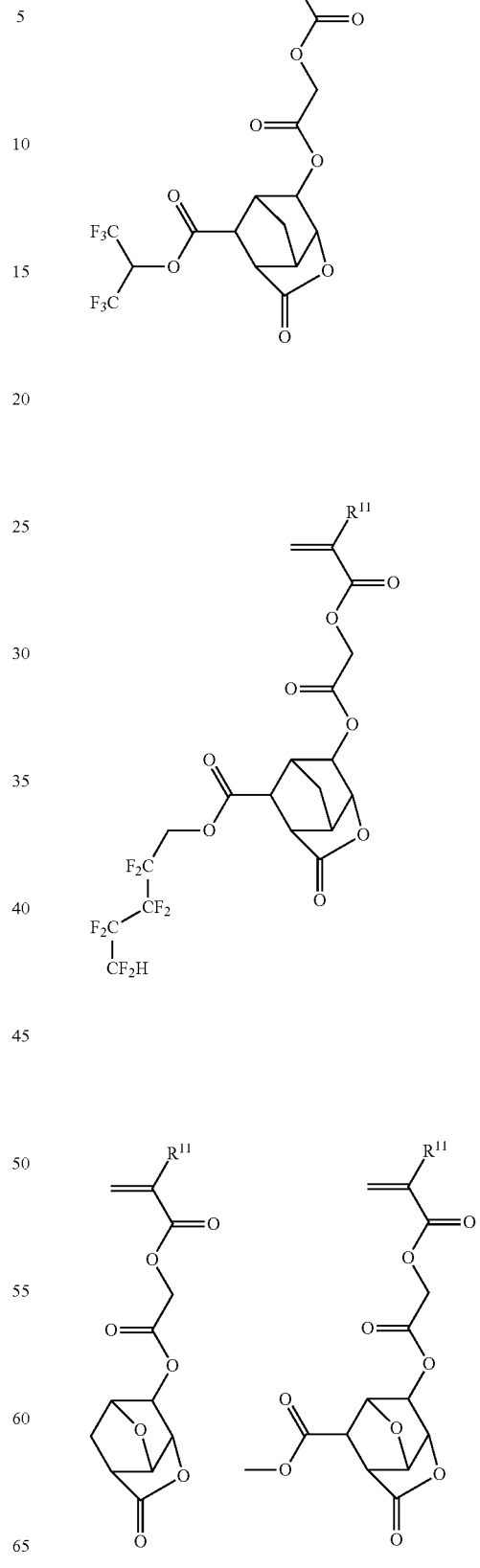

57
-continued
58
-continued
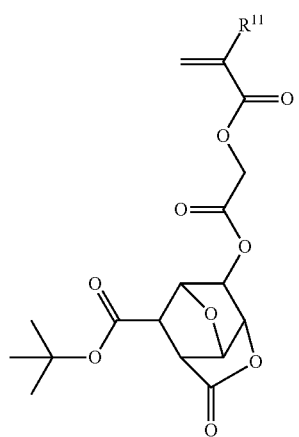
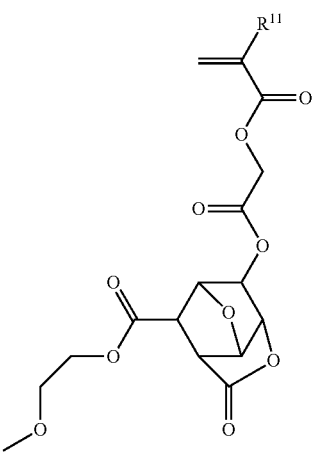
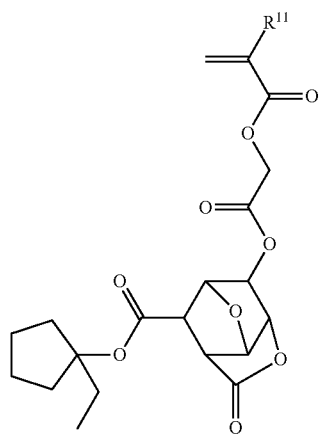
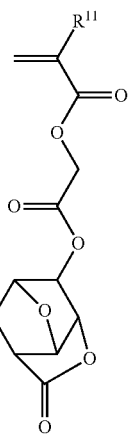

-continued
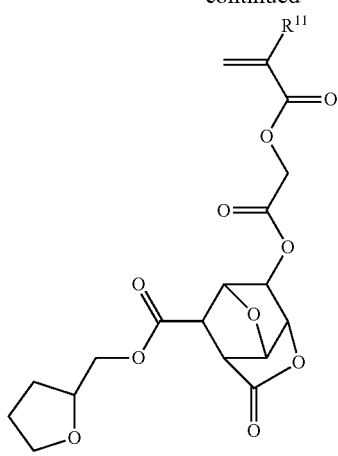
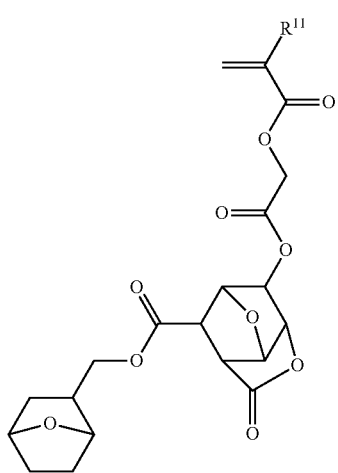
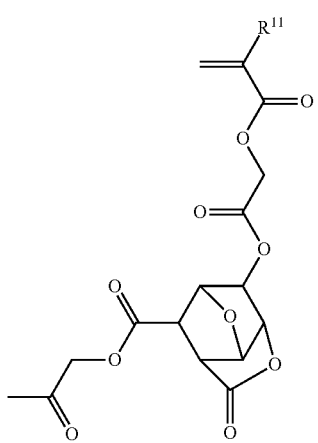
-continued
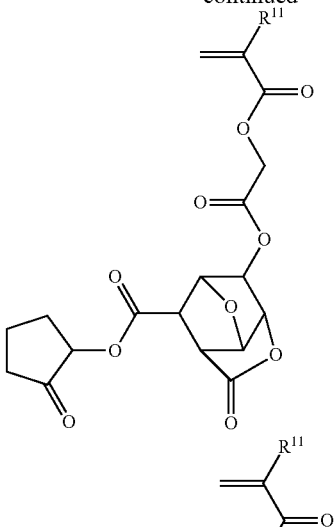
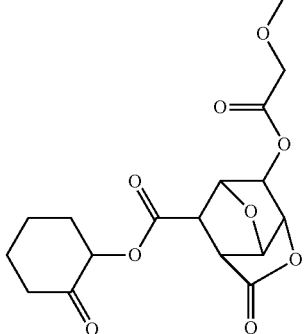
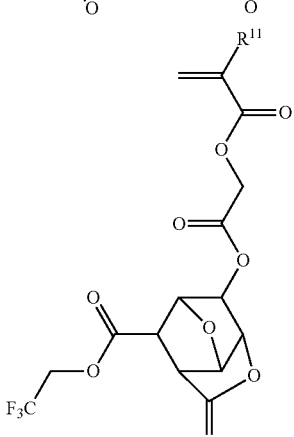
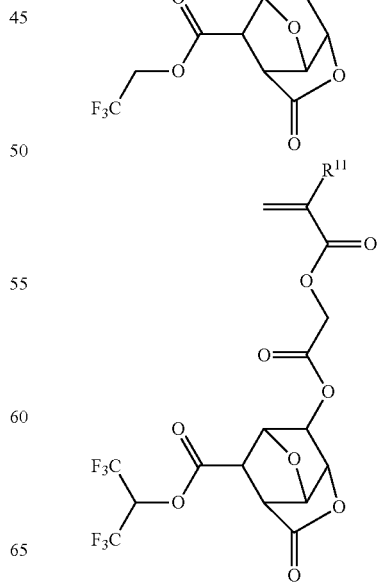

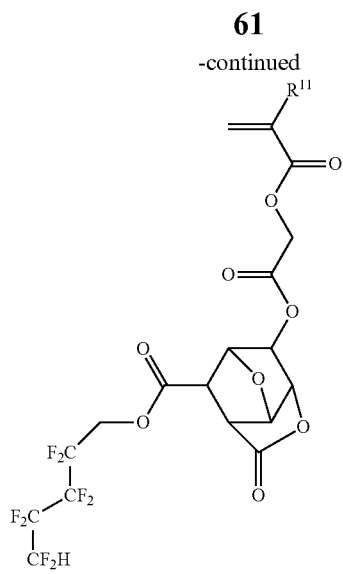

Herein $R^{11}$ is as defined above.

Of the monomers from which recurring units of formula (5L-1) are derived, those monomers wherein M'=1 are described in JP-A 2008-031298. Those monomers wherein M'=2 may be similarly synthesized aside from using 3-chloropropynyl chloride instead of chloroacetyl chloride used as the reactant in the synthesis of the compounds wherein M'=1. Those monomers wherein M'=3 may be similarly synthesized aside from using chlorobutyric chloride instead of chloroacetyl chloride used as the reactant in the synthesis of the compounds wherein M'=1.

Illustrative examples of the recurring units of formula (14) are given below.

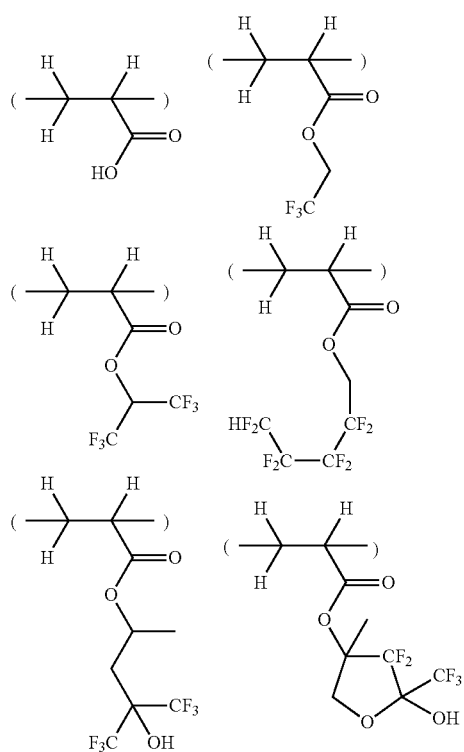

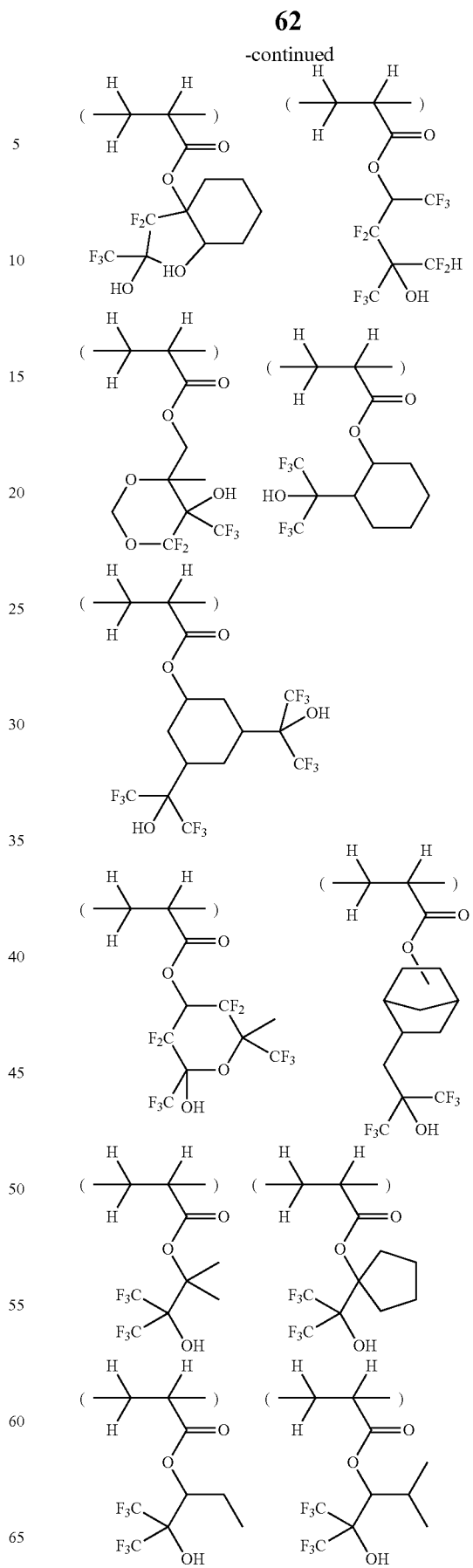

-continued
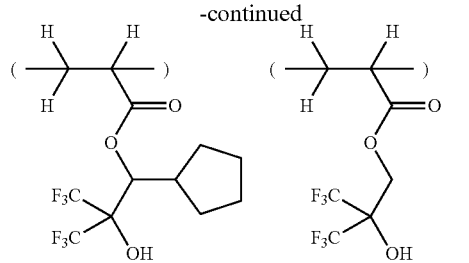
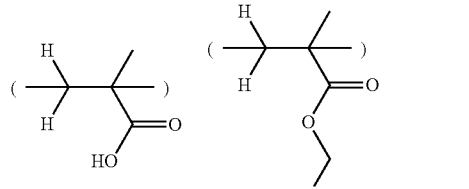
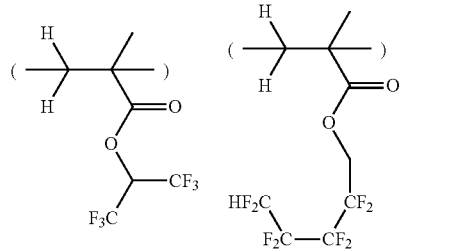
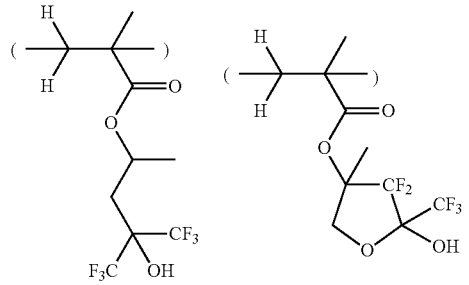
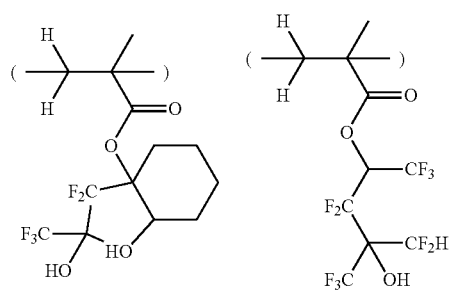
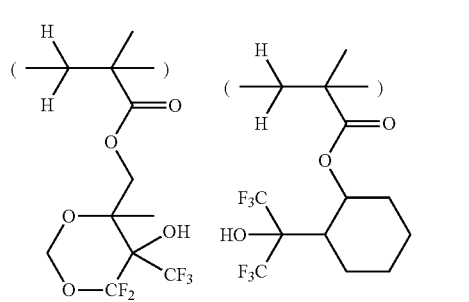
-continued
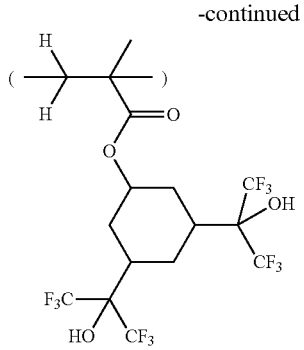
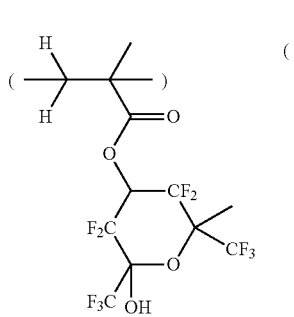
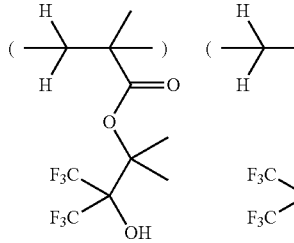
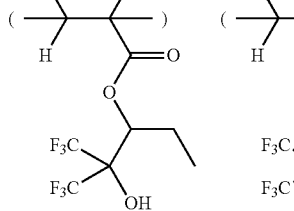
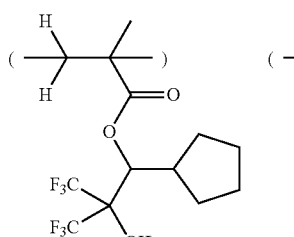
Illustrative examples of the recurring units of formula (15) are given below.

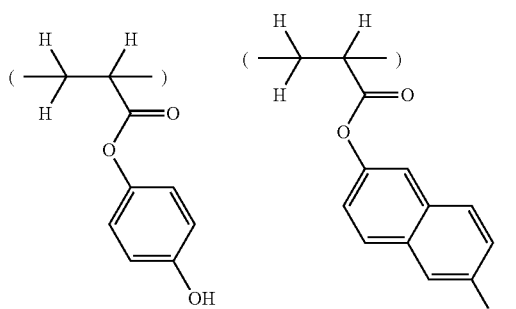
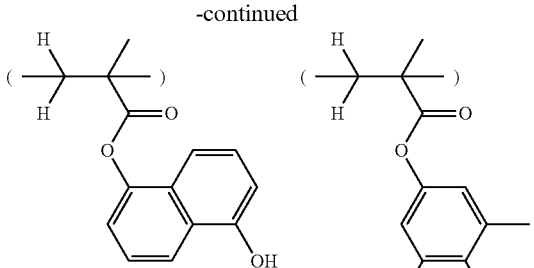
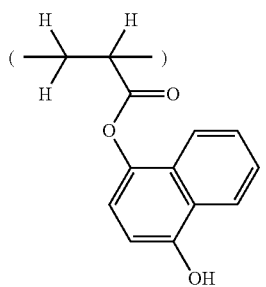
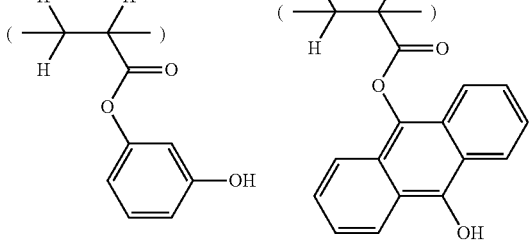
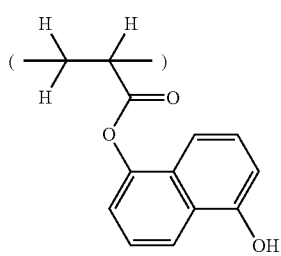
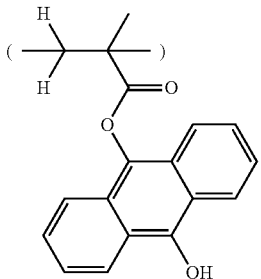
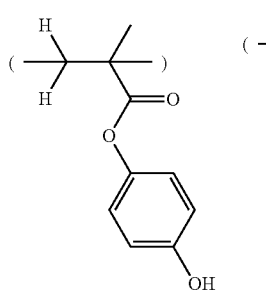
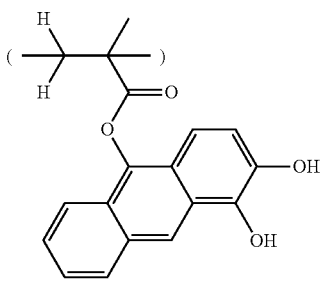
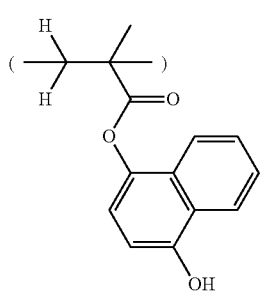
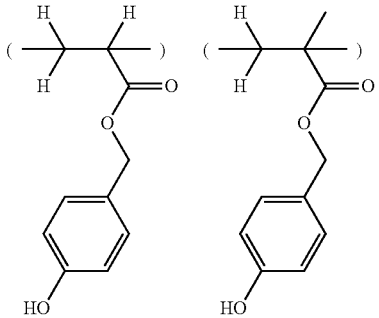
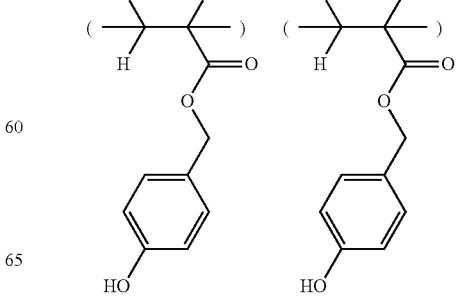

-continued

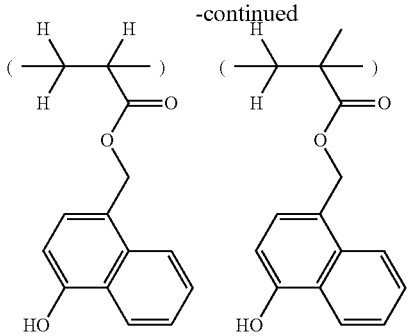

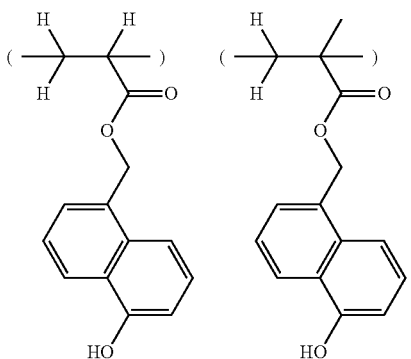

The polymer of the invention may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cycloolefins such as norbornene, norbornene derivatives, and tetracyclo [6.2.1.1$^{3,6}$.0$^{2,7}$]dodecene derivatives, unsaturated acid anhydrides such as itaconic anhydride, and other monomers.

The polymers of the invention are applicable not only to the ArF or EUV photolithography, but also to another lithography such as KrF or EB lithography.

In an embodiment wherein the resist composition is applied to the KrF or EB lithography, the polymer as the base resin may preferably comprise recurring units of at least one type selected from the general formulae (21) to (25) and optionally, recurring units of at least one type selected from the above formulae (11) to (15).

(21)

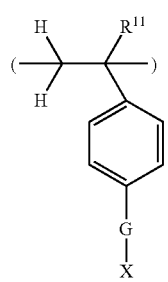

-continued (22)

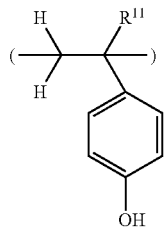

(23)

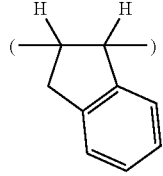

(24)

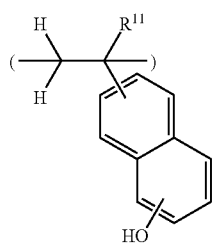

(25)

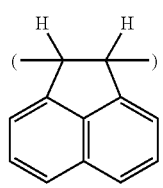

Herein R$^{11}$ and X are as defined above, and G is an oxygen atom or carbonyloxy group (—C(═O)O—).

Under the action of an acid, a polymer comprising recurring units of formula (21) is decomposed to generate a phenolic hydroxyl group and/or carboxylic acid whereby it becomes alkali soluble. The acid labile group X may be selected from a variety of such groups, for example, groups of formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, as illustrated previously.

Illustrative non-limiting examples of the recurring units of formula (21) are given below.

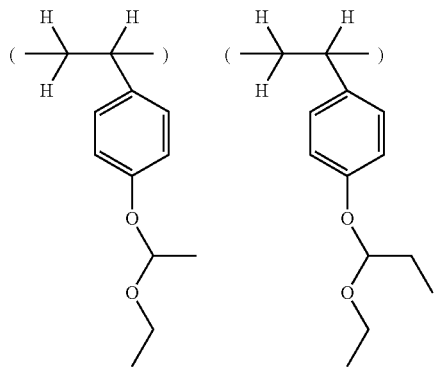

-continued

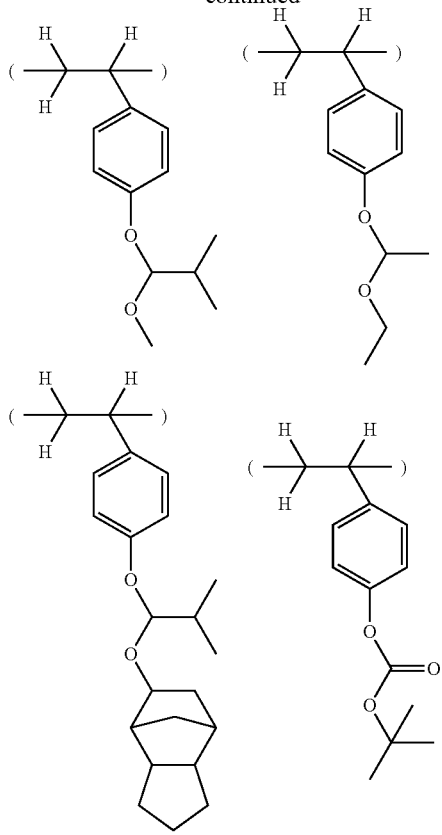

-continued

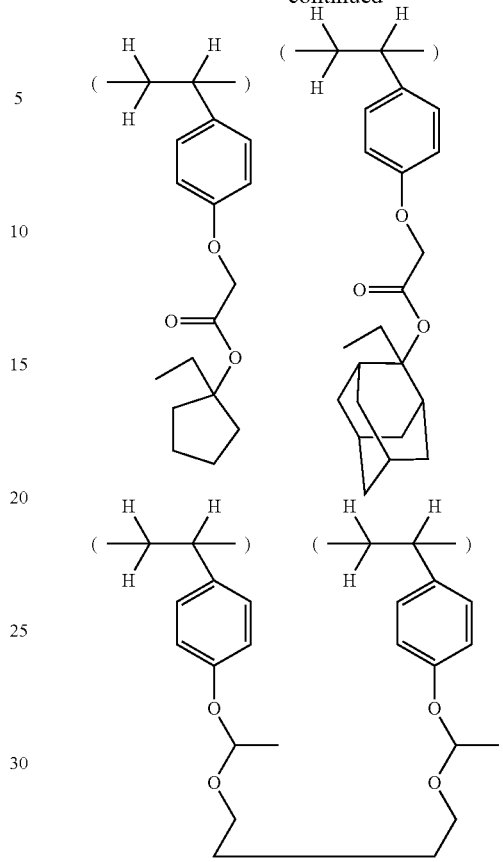

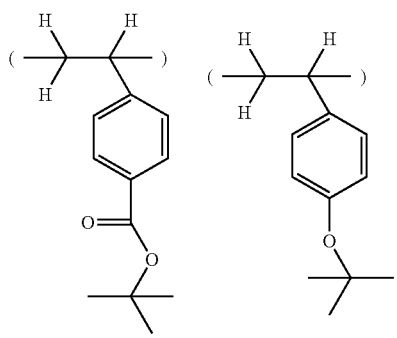

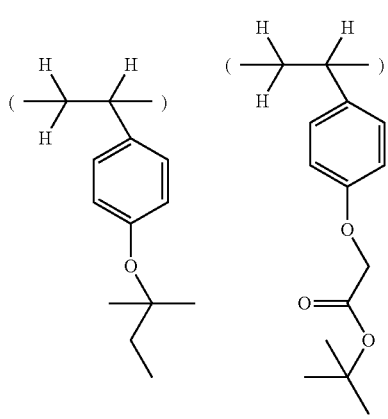

While hydroxyvinylnaphthalene of formula (24) may be substituted at arbitrary positions, typical substituted ones include 6-hydroxy-2-vinylnaphthalene and 4-hydroxy-1-vinylnaphthalene, with 6-hydroxy-2-vinylnaphthalene being preferred.

More preferred are those polymers comprising recurring units of any one type selected from formulae (21) to (25) and recurring units of formula (11) selected from among the recurring units of formulae (11) to (15).

The primary polymer comprising recurring units of any one or more type selected from formulae (21) to (25) may further comprise recurring units derived from another monomer having a carbon-to-carbon double bond other than the foregoing. Examples of the additional monomer include substituted acrylates such as methyl methacrylate, methyl crotonate, dimethyl maleate, and dimethyl itaconate, unsaturated carboxylic acids such as maleic acid, fumaric acid and itaconic acid, cycloolefins such as norbornene, norbornene derivatives, tetracyclo[6.2.1.1$^{3,6}$.0$^{2,7}$]dodecene derivatives, and norbornadiens, unsaturated acid anhydrides such as itaconic anhydride, styrene, acenaphthylene, vinylnaphthalene, and other monomers.

The polymers have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards.

In the polymer, the preferred proportion of respective recurring units derived from discrete monomers may fall, for example, in the range (mol %) shown below, but is not limited thereto. The polymer may consist essentially of (I) from more than 0 mol % to 100 mol %, preferably 70 to 100 mol %, and more preferably 80 to 100 mol % of constituent units of one or more type having formulae (11) to (15) and/or (21) to (25), and optionally (II) from 0 mol % to less than 100 mol %, preferably 0 to 30 mol %, and more preferably 0 to 20 mol % of constituent units of one or more type derived from the additional monomer(s).

The polymer used as the base resin in the chemically amplified positive resist composition should comprise recurring units of formula (11) or (21). Preferably the polymer comprises recurring units of formulae (11), (12) and (13), or formulae (21) and (22), and optionally recurring units of formulae (23) or (25).

The polymer may be prepared through copolymerization reaction using one or more compounds having a polymerizable double bond as a monomer(s). Various modes of copolymerization reaction may be used for the preparation of the polymer. The preferred modes are radical polymerization, anionic polymerization and coordination polymerization.

For radical polymerization, preferred reaction conditions include (a) a solvent selected from hydrocarbon solvents such as benzene, ether solvents such as tetrahydrofuran, alcohol solvents such as ethanol, and ketones such as methyl isobutyl ketone; (b) a polymerization initiator selected from azo compounds such as 2,2'-azobisisobutyronitrile and peroxides such as benzoyl peroxide and lauroyl peroxide; (c) a reaction temperature in the range of about 0° C. to about 100° C.; and (d) a reaction time in the range of about 0.5 to about 48 hours. Reaction parameters outside these ranges need not be excluded.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

Once a polymer is prepared by any of the above-described procedures, it may be modified by deprotecting some or all acid labile groups so that the polymer may be used in negative resist compositions as will be described later. Into the polymer in which acid labile groups have been deprotected, different acid labile groups may be introduced again. This indicates that acid labile groups different from the acid labile groups initially introduced during polymerization are introduced into the polymer.

For example, once a polymer is formed through radical polymerization of 4-ethoxyethoxystyrene with another polymerizable compound, the polymer may be tailored into a copolymer with hydroxystyrene by eliminating ethoxyethoxy groups from the polymer using acetic acid, pyridinium tosylate or the like. The tailored copolymer may be used as a base resin in negative resist compositions. By further reacting hydroxystyrene units of the copolymer with di-tert-butyl dicarbonate, tert-butyl chloroacetate, vinyl ether or the like, acid labile groups different from the acid labile groups (ethoxyethoxy) initially introduced during polymerization may be introduced into the copolymer.

The base resin as component (A) may comprise another resin, specifically another polymer having a dissolution rate in an alkaline developer that increases under the action of acid, if desired, as well as the above-described polymer (sometimes referred to as "primary polymer" merely for the distinguishing purpose). Exemplary other resins include, but are not limited to, (i) poly(meth)acrylic acid derivatives, (ii) norbornene derivative/maleic anhydride copolymers, (iii) hydrogenated products of ring-opening metathesis polymerization (ROMP) polymers, (iv) vinyl ether/maleic anhydride/(meth)acrylic acid derivative copolymers, and (v) polyhydroxystyrene derivatives.

Of these, the poly(meth)acrylic acid derivatives (i) are polymers comprising units of formulae (11) to (15) and other units in combination. The polyhydroxystyrene derivatives (v) include polymers comprising units of formulae (21) to (25) in combination and polymers comprising units of formulae (11) to (15) and formulae (21) to (25) in combination. In these polymers, a proportion of those units having acid labile groups, for example, monomer units of one or more types selected from among formulae (11) and (21) and a combination thereof is from more than 0 mole % to 80 mole %, preferably 1 to 50 mole %, and more preferably 10 to 40 mole %. A proportion of those units free of acid labile groups, for example, monomer units of one or more types selected from among formulae (12) to (15) and (22) to (25) and a combination thereof is from 0 mole % to less than 100 mole %, and when contained, preferably 20 to less than 100 mole %, more preferably 50 to 99 mole %, and even more preferably 60 to 90 mole %.

The hydrogenated ROMP polymers (iii) are synthesized by the method illustrated in Examples of JP-A 2003-66612.

The primary polymer and the other polymer are preferably blended in a weight ratio from 100:0 to 10:90, more preferably from 100:0 to 20:80. If the blend ratio of the primary polymer is below this range, the resist composition would become poor in some of the desired properties. The properties of the resist composition can be adjusted by properly changing the blend ratio of the primary polymer. The polymer is not limited to one type and a mixture of two or more polymers may be added. The use of plural polymers allows for easy adjustment of resist properties.

Organic Solvent

The organic solvent (B) used herein may be any organic solvent in which the base resin, acid generator, and other components are soluble. Examples of the organic solvent are described in U.S. Pat. No. 7,537,880 or JP-A 2008-111103, paragraphs [0144] to [0145]. An appropriate amount of the organic solvent used is mostly 200 to 15,000 parts, specifically 400 to 8,000 parts by weight per 100 parts by weight of the base resin although the amount is generally determined in accordance with the desired film thickness or the like.

Acid Generator

In addition to the photoacid generator of the invention, the resist composition may further contain (C) another acid generator. It may be any compound capable of generating an acid upon exposure to high-energy radiation. Suitable auxiliary photoacid generators include sulfonium salts, iodonium salts, sulfonyldiazomethane, N-sulfonyloxyimide, and oxime-O-sulfonate acid generators. The auxiliary photoacid generators may be used alone or in admixture of two or more. Examples of the acid generator are described in JP-A 2008-133448, JP-A 2007-145797, JP-A 2008-106045, and JP-A 2009-080474.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid as mentioned above) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the chemically amplified resist composition, the photoacid generator (C) may be added in any desired amount as long as the objects of the invention are not compromised. An appropriate amount of the photoacid generator (C), when added, is 0.1 to 80 parts, and more preferably 0.1 to 40 parts by weight per 100 parts by weight of the base resin in the composition. Too high a proportion of the photoacid generator (C) may give rise to problems of degraded resolution and foreign matter upon development and resist film peeling. The photoacid generators (C) may be used alone or in admixture of two or more. The transmittance of the resist film can be controlled by using a photoacid generator having a low transmittance at the exposure wavelength and adjusting the amount of the photoacid generator added.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996). Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior. In the resist composition, an appropriate amount of the acid amplifier compound is up to 20 parts, and especially up to 10 parts by weight per 100 parts by weight of the base resin. Excessive amounts of the acid amplifier compound make diffusion control difficult, leading to degradation of resolution and pattern profile.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of the quencher are described in U.S. Pat. No. 7,537,880 or JP-A 2008-111103, paragraphs [0146] to [0163].

Tertiary amines are especially preferred as the quencher. Examples include tri-n-butylamine, tri-n-pentylamine, tri-n-hexylamine, tri-n-octylamine, N,N-dimethylaniline, triethanolamine, triisopropanolamine, tris(2-methoxymethoxyethyl)amine, tris(2-methoxyethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Further examples of the quencher include 1-[2-(methoxymethoxy)ethyl]pyrrolidine, 1-[2-(methoxymethoxy)ethyl]piperidine, 4-[2-(methoxymethoxy)ethyl]morpholine, 1-[2-(methoxymethoxy)ethyl]imidazole, 1-[2-(methoxymethoxy)ethyl]benzimidazole, 1-[2-(methoxymethoxy)ethyl]-2-phenylbenzimidazole, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 1-[2-[(2-methoxyethoxy)methoxy]ethyl]imidazole, 1-[2-[(2-methoxyethoxy)methoxy]ethyl]benzimidazole, 1-[(2-[(2-methoxyethoxy)methoxy]ethyl]-2-phenylbenzimidazole, 1-[2-[2-(2-methoxyethoxy)ethoxy]ethyl]pyrrolidine, 1-[2-[2-(2-methoxyethoxy)ethoxy]ethyl]piperidine, 4-[2-[2-(2-methoxyethoxy)ethoxy]ethyl]morpholine, 1-[2-[2-(2-methoxyethoxy)ethoxy]ethyl]imidazole, 1-[2-[2-(2-methoxyethoxy)ethoxy]ethyl]benzimidazole, 1-[2-[2-(2-methoxyethoxy)ethoxy]ethyl]-2-phenylbenzimidazole, 1-[2-[2-(2-butoxyethoxy)ethoxy]ethyl]pyrrolidine, 1-[2-[2-(2-butoxyethoxy)ethoxy]ethyl]piperidine, 4-[2-[2-(2-butoxyethoxy)ethoxy]ethyl]morpholine, 1-[2-[2-(2-butoxyethoxy)ethoxy]ethyl]imidazole, 1-[2-[2-(2-butoxyethoxy)ethoxy]ethyl]benzimidazole, 1-[2-[2-(2-butoxyethoxy)ethoxy]ethyl]-2-phenylbenzimidazole, 1-[2-[2-[2-(2-methoxyethoxy)ethoxy]ethoxy]ethyl]pyrrolidine, 1-[2-[2-[2-(2-methoxyethoxy)ethoxy]ethoxy]ethyl]piperidine, 4-[2-[2-[2-(2-methoxyethoxy)ethoxy]ethoxy]ethyl]morpholine, 1-[2-[2-[2-(2-methoxyethoxy)ethoxy]ethoxy]ethyl]imidazole, 1-[2-[2-[2-(2-methoxyethoxy)ethoxy]ethoxy]ethyl]benzimidazole, 1-[2-[2-[2-(2-methoxyethoxy)ethoxy]ethoxy]ethyl]-2-phenyl-benzimidazole, 4-[2-[2-[2-(2-butoxyethoxy)ethoxy]ethoxy]ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazolyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benzimidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl) ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl) ethyl 2-[2-(2-methoxyethoxy)ethoxy]acetate, 2-(1-benzimidazolyl)ethyl 2-[2-(2-methoxyethoxy)ethoxy]acetate, 2-(2-phenyl-1-benzimidazolyl)ethyl 2-[2-(2-methoxyethoxy)-ethoxy]acetate, 2-morpholinoethyl butyrate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl) cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl) ethyl benzoate, 2-piperidinoethyl benzoate, 2-morpholinoethyl benzoate, 2-(1-imidazolyl)ethyl benzoate, 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, etc.

The quenchers may be used alone or in admixture of two or more. The quencher is preferably formulated in an amount of 0.01 to 20 parts, and especially 0.1 to 10 parts by weight, per 100 parts by weight of the total base resin. Less than 0.01 phr of the quencher may achieve no addition effect whereas more than 20 phr may lead to too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Examples of the surfactant are described in U.S. Pat. No. 7,537,880 or JP-A 2008-111103, paragraphs [0165] to [0166].

Additional useful surfactants include partially fluorinated oxetane ring-opened polymers having the structural formula (surf-1).

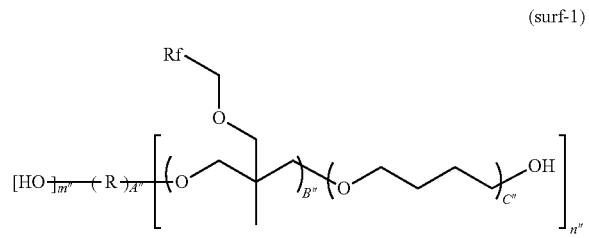

(surf-1)

It is provided herein that R, Rf, A", B", C", m", and n" are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

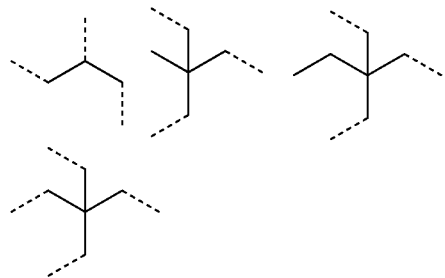

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m" is an integer of 0 to 3, n" is an integer of 1 to 4, and the sum of m" and n", which represents the valence of R, is an integer of 2 to 4. A" is equal to 1, B" is an integer of 2 to 25, and C" is an integer of 0 to 10. Preferably, B" is an integer of 4 to 20, and C" is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430 (3M), Surflon S-381, Surfynol E1004, KH-20 and KH-30 (Asahi Glass Co., Ltd.), and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage.

In the resist composition, the polymeric surfactant is preferably formulated in an amount of 0.001 to 20 parts, and more preferably 0.01 to 10 parts by weight, per 100 parts by weight of the base resin. Reference should also be made to JP-A 2007-297590.

A further embodiment is a chemically amplified negative working resist composition comprising the primary polymer. When used in this embodiment, the primary polymer should contain recurring units having a substituent group capable of forming a crosslinked structure with an acid crosslinker. Examples of such recurring units include, but are not limited to, those units derived from acrylic acid, methacrylic acid, hydroxystyrene (which may be substituted at any positions), and hydroxyvinylnaphthalene (which may be substituted at any positions).

Besides the primary polymer, any alkali-soluble resins may be added. Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

The primary polymer and the other alkali-soluble resin are preferably blended in a weight ratio from 100:0 to 10:90, more preferably from 100:0 to 20:80. If the blend ratio of the primary polymer is below this range, the resist composition would become poor in some of the desired properties. The properties of the resist composition can be adjusted by properly changing the blend ratio of the primary polymer.

Notably, the alkali-soluble resin is not limited to one type and a mixture of two or more resins may be added. The use of plural resins allows for easy adjustment of resist properties.

Crosslinker

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker (F) is, though not limited thereto, 1 to 20 parts, and especially 5 to 15 parts by weight per 100 parts by weight of the base resin. The crosslinkers may be used alone or in admixture of two or more.

While the resist composition of the invention typically comprises a polymer or base resin, acid generator, organic solvent and quencher as described above, there may be added optional other ingredients such as surfactants and crosslinkers, as well as dissolution inhibitors, acidic compounds, stabilizers, and dyes. Optional ingredients may be added in conventional amounts so long as this does not compromise the objects of the invention.

In forming a pattern from the resist composition of the invention, any well-known lithography may be employed. For example, the composition is applied onto a substrate for integrated circuitry fabrication (e.g., Si, $SiO_2$, SiN, SiON, TiN, WSi, BPSG, SOG, organic antireflective coating, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 20 minutes, preferably 80 to 140° C. for 1 to 10 minutes, to form a resist film of 0.05 to 2.0 μm thick. A patterning mask having the desired pattern is then placed over the resist film, and the film exposed through the mask to an electron beam or to high-energy radiation such as deep-UV, excimer laser or x-ray. The exposure dose is preferably 1 to 200 mJ/cm$^2$, more preferably 10 to 100 mJ/cm$^2$ for radiation exposure and preferably 0.1 to 20 μC/cm$^2$, more preferably 3 to 10 μC/cm$^2$ for EB exposure. Light exposure may be done by a conventional exposure process or in some cases, by an immersion process of providing liquid impregnation between the mask and the resist film. In the case of immersion lithography, a protective coating which is insoluble in water may be used. The resist film is then post-exposure baked (PEB) on a hot plate at 60 to 150° C. for 1 to 20 minutes, and preferably at 80 to 140° C. for 1 to 10 minutes. Finally, development is carried out using as the developer an aqueous alkali solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV having a wavelength of 250 to 190 nm, excimer laser, x-ray, or electron beam. The desired pattern may not be obtainable outside the upper and lower limits of the above range.

The water-insoluble protective coating which is used in the immersion lithography is to prevent the resist coating from being leached and to improve water slippage at the coating surface and is generally divided into two types. The first type is an organic solvent-strippable protective coating which must be stripped, prior to alkaline development, with an organic solvent in which the resist coating is not dissolvable. The second type is an alkali-soluble protective coating which is soluble in an alkaline developer so that it can be removed simultaneously with the removal of solubilized areas of the resist coating. The protective coating of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective coating of the second type is formed.

Any desired step may be added to the pattern forming process. For example, after a photoresist coating is formed, a step of rinsing with pure water (post-soaking) may be introduced to extract the acid generator or the like from the coating surface or wash away particles. After exposure, a step of rinsing (post-soaking) may be introduced to remove any water remaining on the coating after exposure.

In a still further embodiment, a photomask is produced by applying the resist composition onto a photomask blank and processing the resist coating to form a resist pattern. The pattern forming process of the invention is advantageously applicable particularly when the photomask blank has a coating of chromium base material as the outermost surface, because the resist pattern is little affected by the substrate (minimized substrate dependence). Also when a resist pattern is formed on a material containing silicon, oxygen and nitrogen, typically a molybdenum-silicon compound, a photomask can be produced in a reliable manner due to the high resolution and aging stability of the resist composition.

Any well-known techniques may be employed in processing the photomask blank using the resist pattern as an etching mask. In general, the processing technique is dry etching with oxygen-containing chlorine gas when the photomask blank has a chromium base compound as the outermost surface. Dry etching with fluorine gas is used when the photomask blank has a transition metal-silicon compound as the outermost surface.

EXAMPLE

Examples and Comparative Examples are given below by way of illustration and not by way of limitation. Mw is a weight average molecular weight, as measured by gel permeation chromatography (GPC) versus polystyrene standards.

Synthesis Example 1-1

Synthesis of Triphenylsulfonium Chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was allowed to mature for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was allowed to mature for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 1-2

Synthesis of 4-tert-butylphenyldiphenylsulfonium bromide

The target compound was obtained by following the procedure of Synthesis Example 1-1 aside from using 4-tert-butylbromobenzene instead of the chlorobenzene in Synthesis Example 1-1 and increasing the amount of water for extraction.

Synthesis Example 1-3

Synthesis of 4-tert-butoxyphenyldiphenylsulfonium chloride

The target compound was obtained by following the procedure of Synthesis Example 1-1 aside from using 4-tert-butoxychlorobenzene instead of the chlorobenzene in Synthesis Example 1-1, using dichloromethane containing 5 wt % of triethylamine as the solvent, and increasing the amount of water for extraction.

Synthesis Example 1-4

Synthesis of tris(4-methylphenyl)sulfonium chloride

The target compound was obtained by following the procedure of Synthesis Example 1-1 aside from using bis(4-methylphenyl)sulfoxide instead of the diphenyl sulfoxide and 4-chlorotoluene instead of the chlorobenzene in Synthesis Example 1-1, and increasing the amount of water for extraction.

Synthesis Example 1-5

Synthesis of tris(4-tert-butylphenyl)sulfonium bromide

The target compound was obtained by following the procedure of Synthesis Example 1-1 aside from using bis(4-tert-butylphenyl)sulfoxide instead of the diphenyl sulfoxide and 4-tert-butylbromobenzene instead of the chlorobenzene in Synthesis Example 1-1, and increasing the amount of water for extraction.

Synthesis Example 1-6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling. A mixture of 35 g of acetic anhydride and 95 g of conc. sulfuric acid was added dropwise thereto at a temperature below 30° C. The reaction solution was allowed to mature for 3 hours at room temperature and ice to cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water, the washing step being repeated three times. After washing, the organic layer was concentrated in vacuum, obtaining a crude target product. The product was used in the subsequent reaction without further purification.

Synthesis Example 1-7

Synthesis of Dimethylphenylsulfonium Sulfate

A mixture of 6.2 g (0.05 mole) of thioanisole and 6.9 g (0.055 mole) of dimethyl sulfate was stirred for 12 hours at room temperature. To the reaction solution were added 100 g of water and 50 ml of diethyl ether. The aqueous layer was taken out, which was an aqueous solution of the target compound, dimethylphenylsulfonium sulfate.

Synthesis Example 1-8

Synthesis of Phenacyltetrahydrothiophenium Bromide

In 220 g of nitromethane were dissolved 88.2 g (0.44 mole) of phenacyl bromide and 39.1 g (0.44 mole) of tetrahydrothiophene. The solution was stirred for 4 hours at room temperature. To the reaction solution were added 800 g of water and 400 g of diethyl ether. The aqueous layer was taken out, which was an aqueous solution of the target compound, phenacyltetrahydrothiophenium bromide.

Synthesis Example 1-9

Synthesis of sodium 2-(pivaloyloxy)-1,1-difluoroethane-sulfonate

Pivalic acid chloride and 2-bromo-2,2-difluoroethanol were mixed in tetrahydrofuran and ice cooled. Triethylamine was added to the mixture. By standard separation operation and solvent distillation, 2-bromo-2,2-difluoroethyl pivalate was obtained. This compound was converted into a sodium sulfinate with sodium dithionite and then oxidized with hydrogen peroxide, yielding the target compound, sodium 2-(pivaloyloxy)-1,1-difluoroethanesulfonate.

Synthesis of carboxylic ester is well known, and synthesis of sulfinic acid and sulfonic acid from alkyl halide is also well known. The latter is described, for example, in JP-A 2004-002252.

Synthesis Example 1-10

Synthesis of triphenylsulfonium 2-(pivaloyloxy)-1,1-difluoroethanesulfonate In 700 g of dichloromethane and 400 g of water were dissolved 159 g (0.37 mole) of sodium 2-(pivaloyloxy)-1,1-difluoroethanesulfonate (purity 63%) and 132 g (0.34 mole) of triphenylsulfonium iodide. The organic layer was separated, washed three times with 200 g of water, and concentrated. Diethyl ether was added to the residue for recrystallization, obtaining the target compound as white crystals. 164 g (yield 95%).

Synthesis Example 1-11

Synthesis of 4-tert-butylphenyldiphenylsulfonium 2-(pivaloyloxy)-1,1-difluoroethanesulfonate In 150 g of dichloromethane were dissolved 20 g (0.052 mole) of sodium 2-(pivaloyloxy)-1,1-difluoroethanesulfonate (purity 70%) and 217 g (0.052 mole) of an aqueous solution of 4-tert-butylphenyldiphenylsulfonium bromide. The organic layer was separated, washed three times with 50 g of water, and concentrated. Diethyl ether was added to the residue for recrystallization, obtaining the target compound as white crystals. 26 g (yield 79%).

Synthesis Example 1-12

Synthesis of triphenylsulfonium 1,1-difluoro-2-hydroxy-ethanesulfonate [PAG1]

Triphenylsulfonium 2-(pivaloyloxy)-1,1-difluoroethanesulfonate, 243.5 g (0.48 mole), was dissolved in 760 g of methanol and ice cooled. An aqueous sodium hydroxide solution (40 g of sodium hydroxide in 120 g of water) was added dropwise at a temperature below 5° C. The solution was allowed to mature for 8 hours at room temperature. At a temperature below 10° C., dilute hydrochloric acid (99.8 g of 12N hydrochloric acid in 200 g of water) was added to quench the reaction. The methanol was distilled off in vacuum. To the residue was added 1,000 g of dichloromethane. The organic layer was washed three times with 30 g of saturated sodium chloride aqueous solution and concentrated. Diisopropyl ether, 1 L, was added to the concentrate for crystallization. The crystals were filtered and dried, obtaining the target compound. Amount 187 g (purity 78%, reduced yield 78%).

The target compound (PAG1) has the following structure.

PAG 1

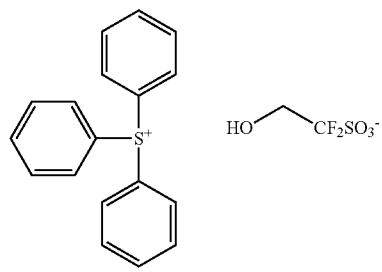

Synthesis Example 1-13

Synthesis of triphenylsulfonium 1,1-difluoro-2-hydroxy-ethanesulfonate [PAG1]

Triphenylsulfonium 2-(pivaloyloxy)-1,1-difluoroethanesulfonate, 50.9 g (0.1 mole), was dissolved in 200 g of methanol and ice cooled. 2.0 g of a 28 wt % methanol solution of sodium methoxide was added. The solution was allowed to mature for 24 hours at room temperature. At a temperature below 10° C., 1.0 g of 12N hydrochloric acid was added to quench the reaction. The methanol was distilled off in vacuum. To the residue was added 250 g of dichloromethane. The inorganic salt was filtered off, after which the filtrate was concentrated. Diisopropyl ether, 150 g, was added to the concentrate for crystallization. The crystals were filtered and dried, obtaining the target compound. Amount 42 g (purity 99%, reduced yield 99%).

Synthesis Examples 1-14 to 1-20

The target compounds were synthesized as in Synthesis Examples 1-10 and 1-12 aside from using the sulfonium or iodonium salts prepared in Synthesis Examples 1-2 to 1-8. These onium salts (PAG2 to PAG8) are shown below.

PAG 2

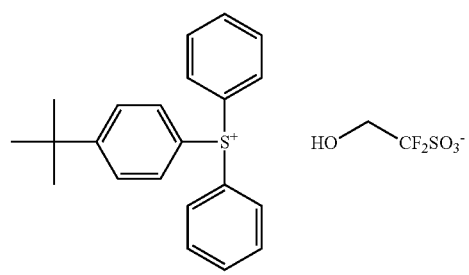

PAG 3

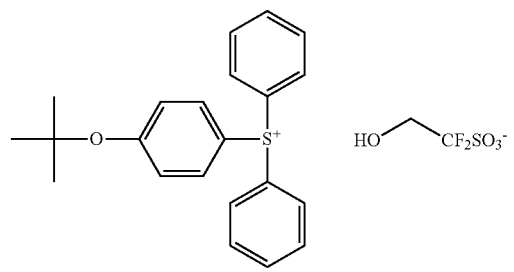

PAG 4

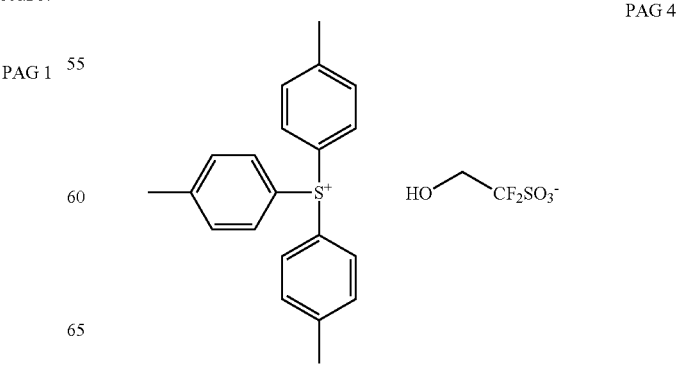

PAG 5

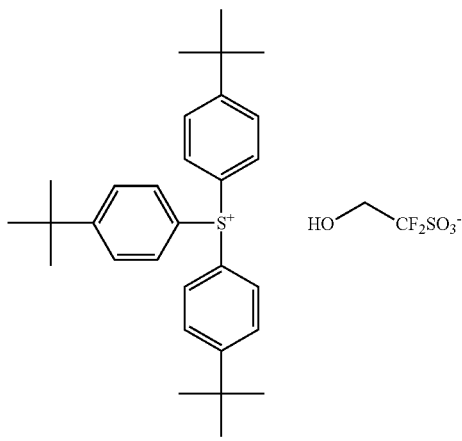

PAG 6

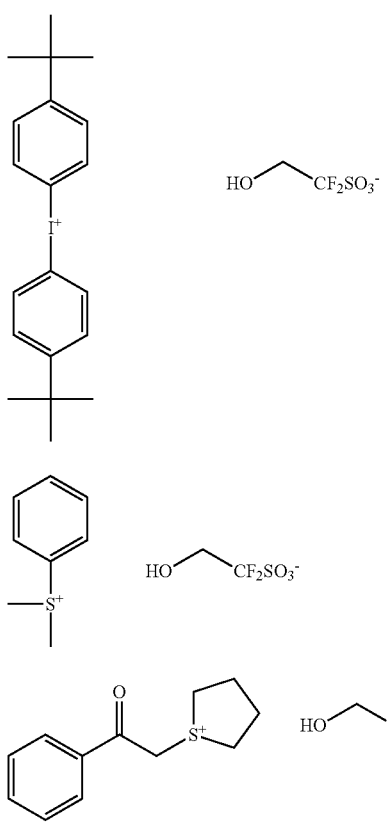

PAG 7

PAG 8

Synthesis Example 1-21

Synthesis of sodium 2-benzoyloxy-1,1,3,3,3-pentafluoro-1-propane-1-sulfonate

In 72 g of water was dispersed 10.0 g of 1,1,3,3,3-pentafluoro-2-propan-2-yl benzoate, which had been synthesized by a conventional technique. Then 12.0 g of sodium hydrogen sulfite was added. The solution was allowed to react at 100° C. for 14 hours. It was allowed to cool and combined with toluene, followed by separatory operation to separate a water layer. A saturated sodium chloride aqueous solution was added to the water layer whereupon white crystals precipitated out. The crystals were collected by filtration, washed with a small volume of saturated sodium chloride aqueous solution and then dried in vacuum, obtaining the target compound, sodium 2-benzoyloxy-1,1,3,3,3-pantafluoro-propane-1-sulfonate. White crystals, 5.85 g (yield 43%).

Synthesis Example 1-22

Synthesis of triphenylsulfonium 2-benzoyloxy-1,1,3,3,3-pentafluoropropane-1-sulfonate To 50 g of dichloromethane were added an amount (corresponding to 0.011 mole) of the triphenylsulfonium chloride aqueous solution obtained in Synthesis Example 1-1 and 3.6 g (0.01 mole) of sodium 2-benzoyloxy-1,1,3,3,3-pantafluoropropane-1-sulfonate synthesized in Synthesis Example 1-21, followed by stirring. The organic layer was separated and washed three times with 50 g of water. The organic layer was concentrated and 25 g of diethyl ether was added to the concentrate for crystallization. The crystals were filtered and dried, obtaining the target compound. White crystals, 4.5 g (yield 75%).

Synthesis Example 1-23

Synthesis of triphenylsulfonium 2-hydroxy-1,1,3,3,3-pentafluoropropane-1-sulfonate [PAG9]

In 72 g of methanol was dissolved 34.4 g of triphenylsulfonium 2-benzoyloxy-1,1,3,3,3-pentafluoropropane-1-sulfonate synthesized in Synthesis Example 1-22. While the solution was stirred under ice cooling, 54.0 g of 5% sodium hydroxide aqueous solution was added dropwise at a temperature below 10° C. The reaction solution was allowed to mature at the temperature for 4 hours. At a temperature below 10° C., 6.8 g of 12N hydrochloric acid was added to quench the reaction. The methanol was distilled off in vacuum, after which 270 g of dichloromethane was added to the residue. The organic layer was washed with 40 g of water three times. The organic layer was concentrated, and 60 g of diethyl ether was added to the concentrate for crystallization. The crystals were filtered and dried, obtaining the target compound. White crystals, 24.3 g (yield 85%). The compound (PAG9) had the following structure.

PAG 9

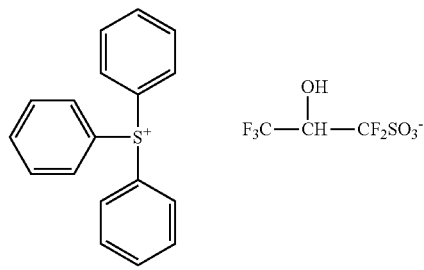

Synthesis Examples 1-24 to 1-30

Target compounds were synthesized as in Synthesis Examples 1-22 and 1-23 except that the sulfonium or iodonium salts prepared in Synthesis Examples 1-2 to 1-8 were used. The resulting onium salts PAG10 to PAG16 are shown below.

PAG 10

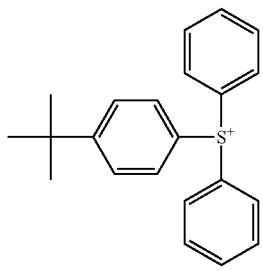 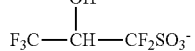

PAG 11

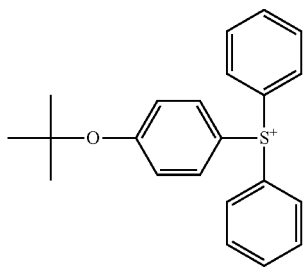 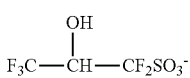

PAG 12

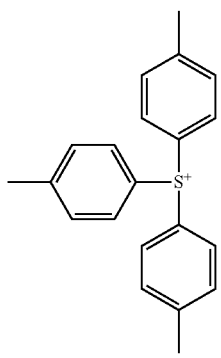 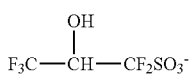

PAG 13

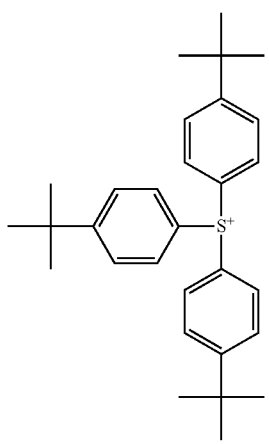 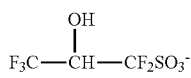

-continued

PAG 14

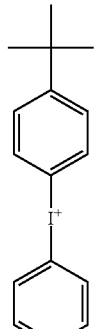 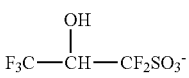

PAG 15

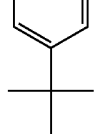 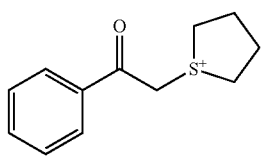

PAG 16

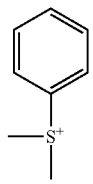 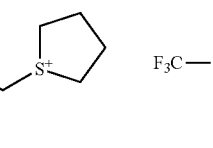

Synthesis Example 1-31

Synthesis of triphenylsulfonium 1-(difluorosulfomethyl)-2,2,2-trifluoroethyl 2-(adamantane-1-carbonyloxy)acetate [PAG-A]

By forming t-butyl 2-(adamantane-1-carbonyloxy)acetate from 1-adamantanecarboxylic acid and t-butyl chloroacetate and effecting deprotection reaction with acid and subsequent reaction with oxalyl chloride, there was synthesized 2-(adamantane-1-carbonyloxy)acetic chloride.

In 40 g of dichloromethane were dissolved 9.8 g (0.02 mole) of triphenylsulfonium 2-hydroxy-1,1,3,3,3-pentafluoro-propane-1-sulfonate (PAG9) in Synthesis Example 1-23, 2.2 g (0.022 mole) of triethylamine, and 0.24 g (0.002 mole) of N,N-dimethylaminopyridine. While the solution was ice cooled, 5.6 g (0.022 mole) of 2-(adamantane-1-carbonyloxy)acetic chloride synthesized above was added at a temperature below 5° C. Stirring was continued for one hour at room temperature. A dilute hydrochloric acid aqueous solution prepared from 3 g of 12N hydrochloric acid and 10 g of water was added, and 80 g of methyl isobutyl ketone and 20 g of water then added. The organic layer was separated and washed twice with 50 g of water, after which the solvent was distilled off in vacuum. Diisopropyl ether was added to the residue for crystallization, obtaining the target compound. White crystals, 12.0 g (yield 84%), m.p. 110-111° C. The target compound had the following structure.

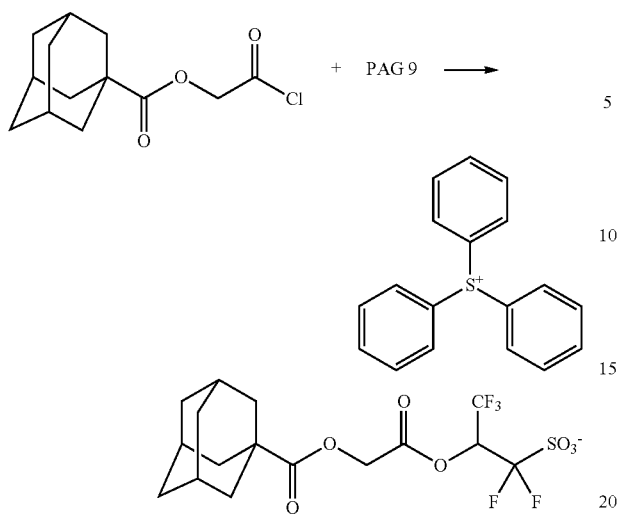

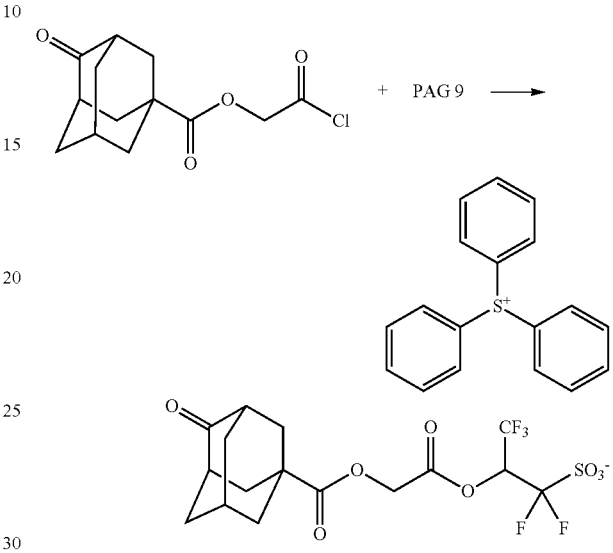

Figure 2:
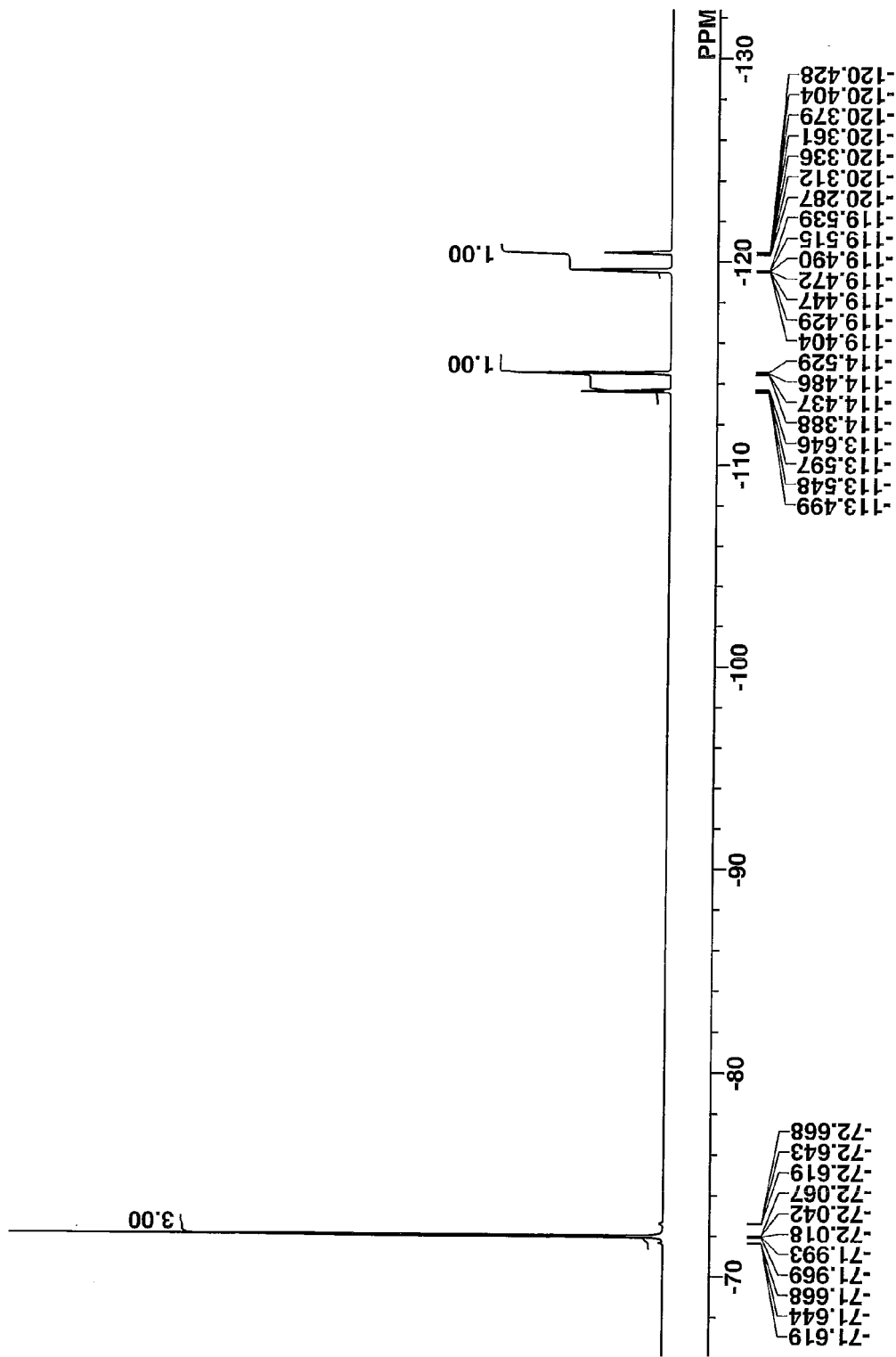
FIG. 2 is a diagram showing the $^{19}$F-NMR/DMSO-$d_6$ spectrum of PAG-A in Synthesis Example 1-31.

The compound was analyzed by spectroscopy. The nuclear magnetic resonance spectra, $^1$H-NMR and $^{19}$F-NMR/DMSO-$d_6$ are shown in FIGS. 1 and 2. Note that in $^1$H-NMR, traces of residual solvents (diisopropyl ether, water) were observed. The data of time-of-flight mass spectrometry (TOFMS) are also shown below.

IR spectra (KBr, cm$^{-1}$): 2933, 2908, 2854, 1787, 1735, 1476, 1448, 1373, 1324, 1266, 1249, 1216, 1177, 1105, 1094, 1071, 995, 938, 835, 751, 684, 642, 578, 552, 535, 505

TOFMS (MALDI): Positive M$^+$263 (corresponding to (C$_6$H$_5$)$_3$S$^+$)

Negative M$^-$449 (corresponding to (C$_{11}$H$_{15}$O$_2$—CH$_2$CO$_2$)CH(CF$_3$)CF$_2$SO$_3^-$)

Analogous compounds were synthesized by following the procedure of Synthesis Example 1-31 aside from using one of PAG11 to PAG16 instead of PAG9, i.e., triphenylsulfonium 2-hydroxy-1,1,3,3,3-pentafluoropropane-1-sulfonate. The compounds correspond to PAG-A wherein the cation is replaced by 4-tert-butoxyphenyldiphenylsulfonium, tris(4-methylphenyl)-sulfonium, tris(4-tert-butylphenyl)sulfonium, bis(4-tert-butylphenyl)iodonium, dimethylphenylsulfonium, and phenacyltetrahydrothiophenium.

Synthesis Example 1-32

Synthesis of triphenylsulfonium 1-(difluorosulfomethyl)-2,2,2-trifluoroethyl 2-(4-oxo-adamantane-1-carbonyloxy)-acetate [PAG-B]

By forming t-butyl 2-(4-oxo-adamantane-1-carbonyloxy)-acetate from 4-oxo-1-adamantanecarboxylic acid and t-butyl chloroacetate and effecting deprotection reaction with acid and subsequent reaction with oxalyl chloride, there was synthesized 2-(4-oxo-adamantane-1-carbonyloxy)acetic chloride.

The acid chloride, 3.1 g (0.01 mole), was combined with 4.9 g (0.01 mole) of triphenylsulfonium 2-hydroxy-1,1,3,3,3-pentafluoropropane-1-sulfonate and 20 g of methylene chloride. To this solution, a mixture of 1.1 g (0.01 mole) of triethylamine, 0.24 g (0.002 mole) of 4-dimethylaminopyridine, and 5.0 g of methylene chloride was added dropwise. Stirring was continued for 3 hours at room temperature. Thereafter, 11 g of 5% hydrochloric acid was added to quench the reaction. The organic layer was taken out of the reaction solution and washed with 20 g of water, after which the dichloromethane was distilled off in vacuum. To the residue were added 30 g of methyl isobutyl ketone and 15 g of dilute aqueous ammonia. The organic layer was separated and washed with 20 g of water. Methyl isobutyl ketone was distilled off in vacuum. The residue was washed with diisopropyl ether and dried in vacuum, obtaining the target compound. Colorless oil, 6.8 g (yield 94%). The target compound had the following structure.

Figure 3:
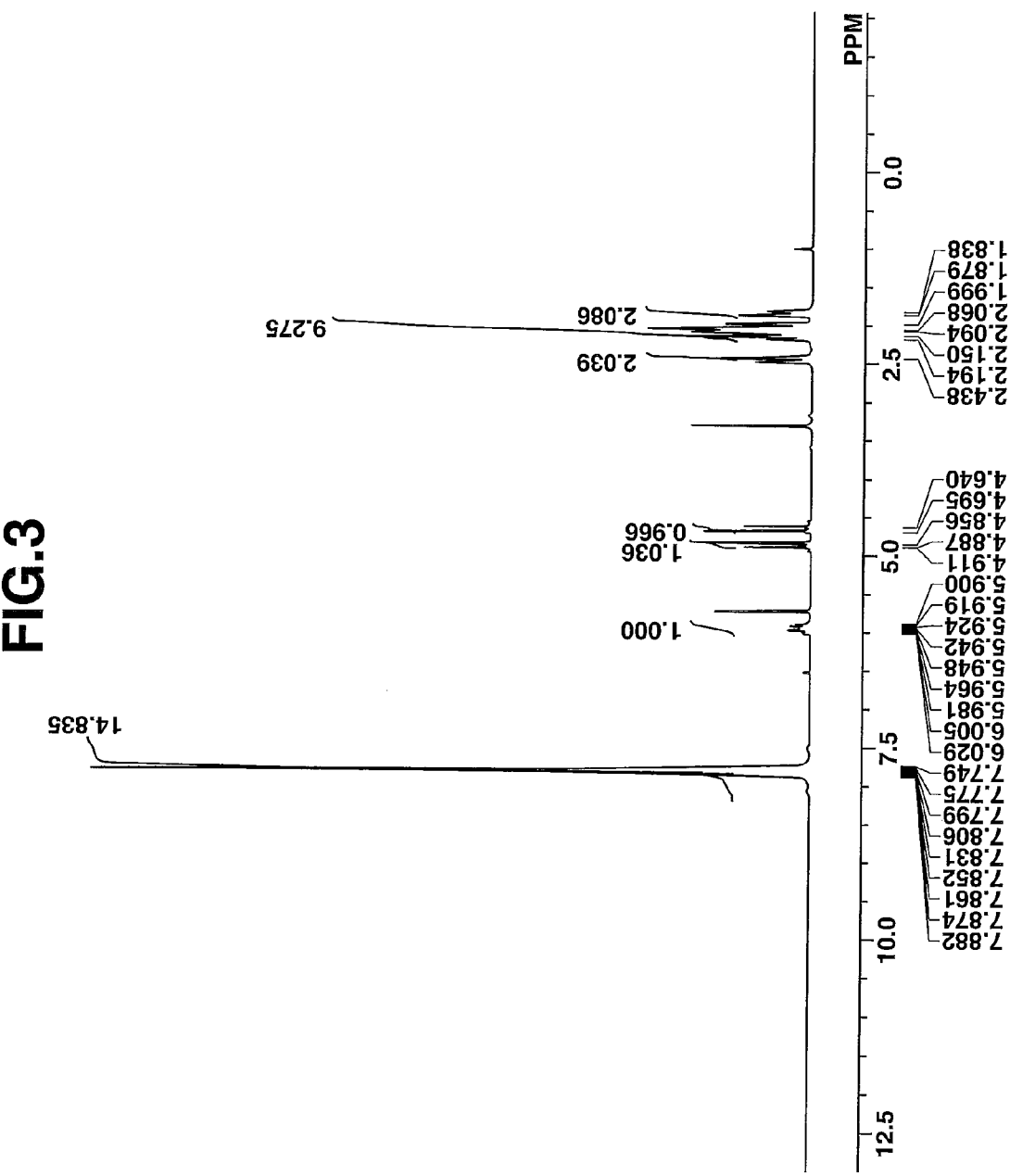
FIG. 3 is a diagram showing the $^1$H-NMR/DMSO-$d_6$ spectrum of PAG-B in Synthesis Example 1-32.
Figure 4:
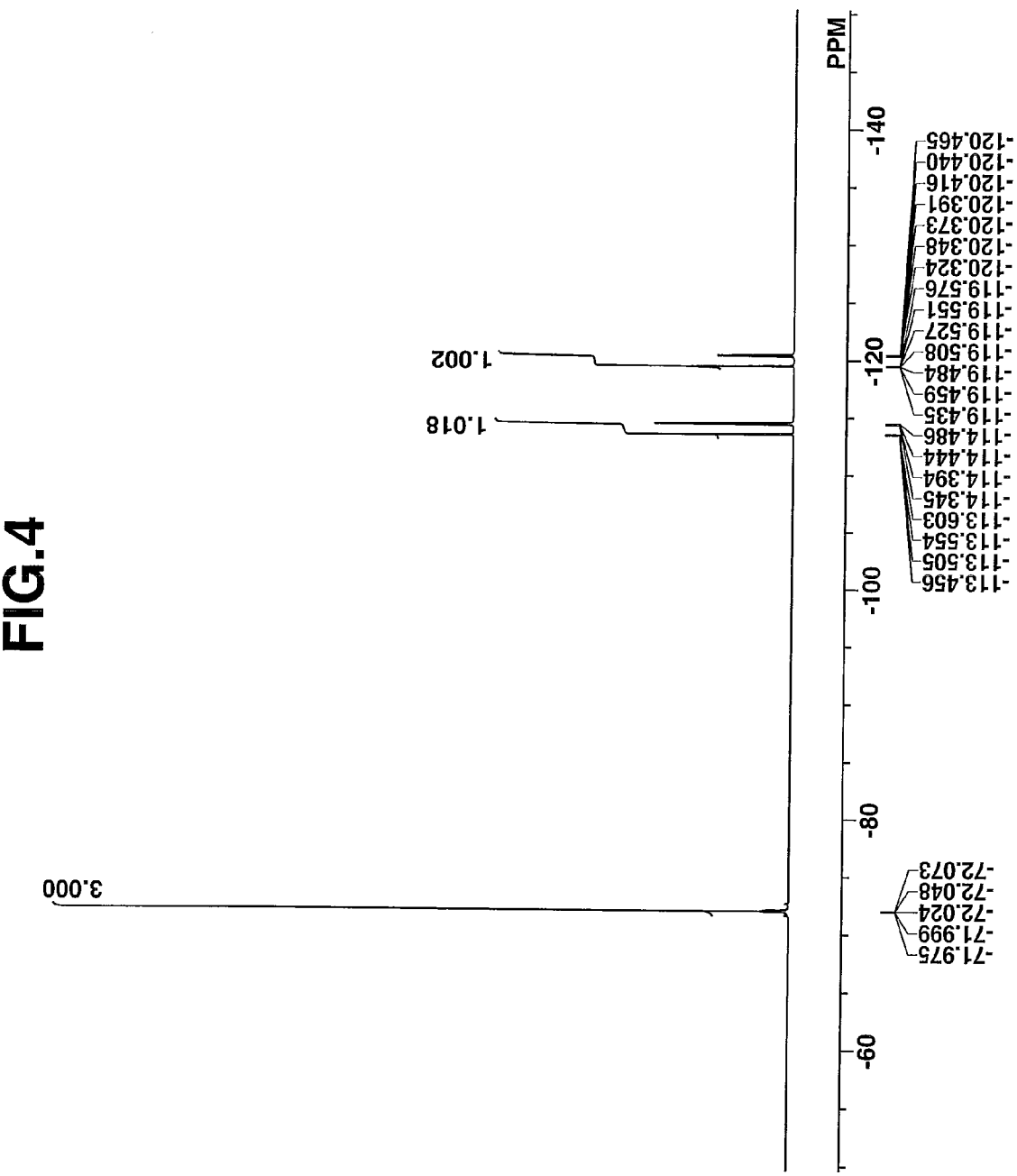
FIG. 4 is a diagram showing the $^{19}$F-NMR/DMSO-$d_6$ spectrum of PAG-B in Synthesis Example 1-32.

The compound was analyzed by spectroscopy. The nuclear magnetic resonance spectra, $^1$H-NMR and $^{19}$F-NMR/DMSO-$d_6$ are shown in FIGS. 3 and 4. Note that in $^1$H-NMR, traces of residual solvents (methylene chloride, diisopropyl ether, water) were observed. The data of time-of-flight mass spectrometry (TOFMS) are also shown below.

IR spectra (KBr, cm$^{-1}$): 2936, 2862, 1788, 1738, 1721, 1476, 1447, 1373, 1251, 1217, 1176, 1102, 1070, 995, 750, 685, 642

TOFMS (MALDI): Positive M$^+$263 (corresponding to (C$_6$H$_5$)$_3$S$^+$)

Negative M$^-$463 (corresponding to (C$_{11}$H$_{13}$O$_3$—CH$_2$CO$_2$)CH(CF$_3$)CF$_2$SO$_3^-$)

Analogous compounds were synthesized by following the procedure of Synthesis Example 1-32 aside from using one of PAG10 to PAG16 instead of PAG9, i.e., triphenylsulfonium 2-hydroxy-1,1,3,3,3-pentafluoropropane-1-sulfonate. The compounds correspond to PAG-B wherein the cation is replaced by 4-tert-butylphenyldiphenylsulfonium, 4-tert-butoxyphenyl-diphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-33

Synthesis of triphenylsulfonium 1,1-difluorosulfoethyl 2-(4-oxo-adamantane-1-carbonyloxy)acetate [PAG-C]

As in Synthesis Example 1-32, 2-(4-oxo-adamantane-1-carbonyloxy)acetic chloride was synthesized.

The acid chloride, 3.1 g (0.01 mole), was combined with 4.3 g (0.01 mole) of triphenylsulfonium 1,1-difluoro-2-hydroxyethanesulfonate and 20 g of methylene chloride. To this solution, a mixture of 1.1 g (0.01 mole) of triethylamine, 0.24 g (0.002 mole) of 4-dimethylaminopyridine, and 5.0 g of methylene chloride was added dropwise. Stirring was continued for 6 hours at room temperature. Thereafter, 11 g of 5% hydrochloric acid was added to quench the reaction. The organic layer was taken out of the reaction solution and washed with 20 g of water and then with dilute aqueous ammonia, after which the dichloromethane was distilled off in vacuum. To the residue was added 30 g of methyl isobutyl ketone. The residual water and methyl isobutyl ketone were azeotroped off. The residue was washed with diisopropyl ether and dried in vacuum, obtaining the target compound. Colorless oil, 5.1 g (yield 77%). The target compound had the following structure.

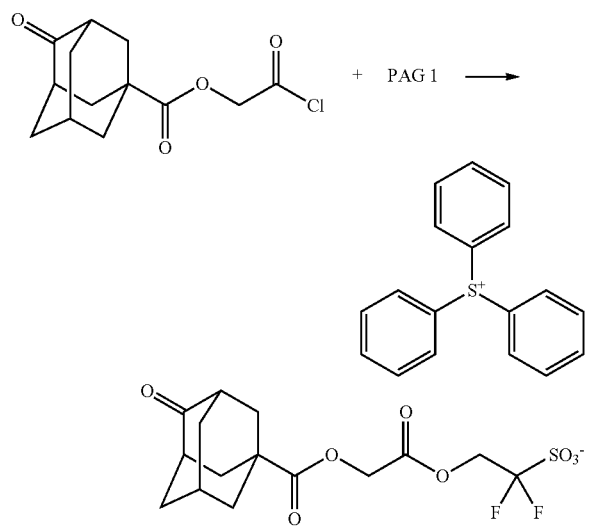

Figure 5:
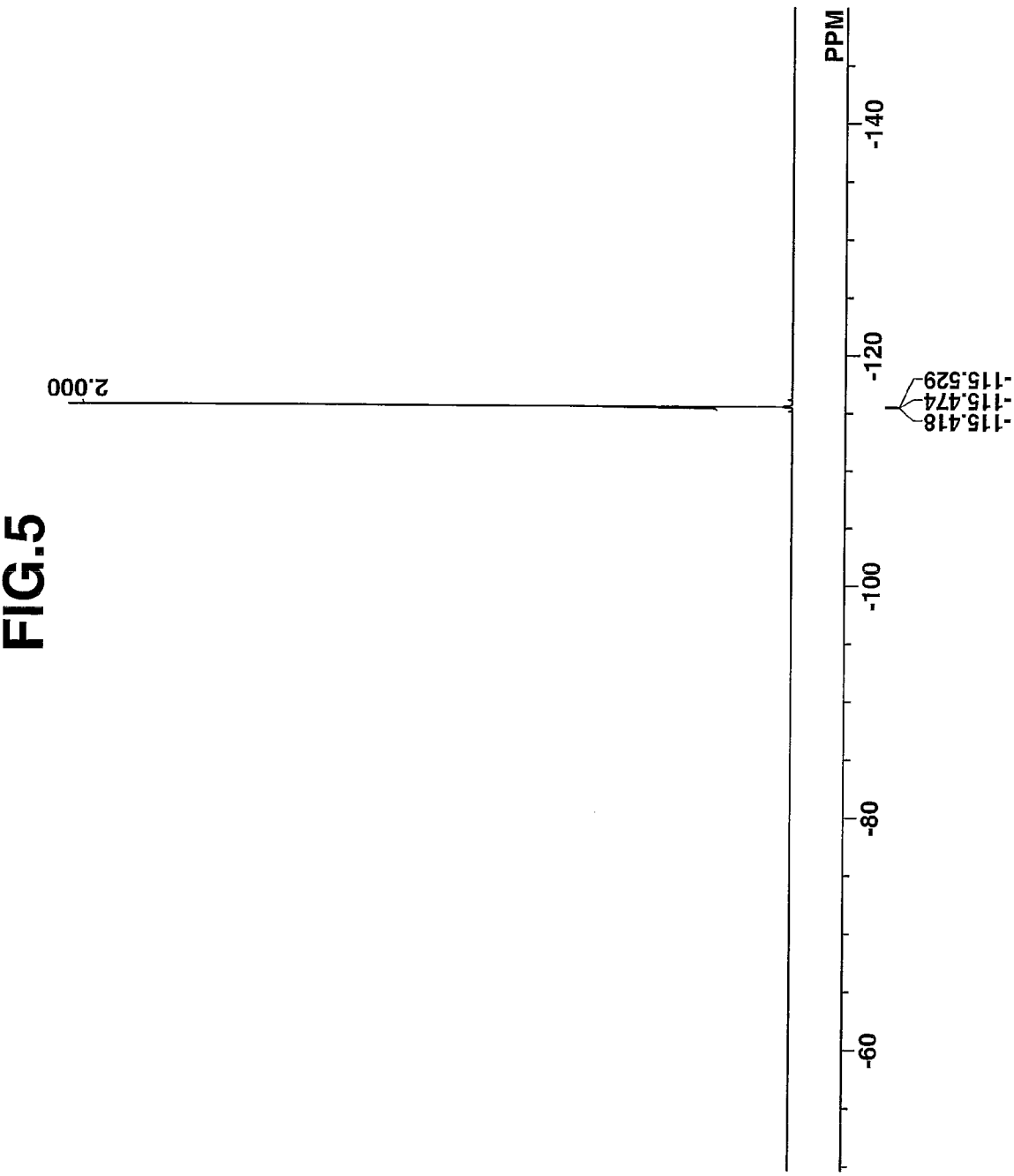
FIG. 5 is a diagram showing the $^{19}$F-NMR/DMSO-$d_6$ spectrum of PAG-C in Synthesis Example 1-33.

The compound was analyzed by spectroscopy. The nuclear magnetic resonance spectrum, $^{19}$F-NMR/DMSO-$d_6$ is shown in FIG. 5. The data of time-of-flight mass spectrometry (TOFMS) are shown below.

TOFMS (MALDI): Positive M$^+$263 (corresponding to $(C_6H_5)_3S^+$)

Negative M$^-$395 (corresponding to $(C_{11}H_{13}O_3$—$CH_2CO_2)CH_2CF_2SO_3^-$)

Analogous compounds were synthesized by following the procedure of Synthesis Example 1-33 aside from using one of PAG2 to PAG8 instead of PAG1, i.e., triphenylsulfonium 2-hydroxy-1,1-difluoroethanesulfonate. The compounds correspond to PAG-C wherein the cation is replaced by 4-tert-butylphenyldiphenylsulfonium, 4-tert-butoxyphenyl-diphenylsulfonium, tris(4-methylphenyl)sulfonium, tris(4-tert-butylphenyl)sulfonium, bis(4-tert-butylphenyl)iodonium, dimethylphenylsulfonium, and phenacyltetrahydrothiophenium.

Synthesis Example 1-34

Synthesis of triphenylsulfonium 2-(4-chlorobutyryloxy)-1,1-difluoroethanesulfonate [PAG intermediate 1]

To a mixed solution of 6.34 g (0.015 mole) of triphenylsulfonium 1,1-difluoro-2-hydroxyethanesulfonate, 1.9 g (0.013 mole) of chlorobutyric chloride, and 32 g of acetonitrile, 1.42 g (0.018 mole) of pyridine was added dropwise. The reaction solution was stirred at room temperature for 4 hours. Thereafter, a dilute hydrochloric acid solution prepared from 3 g of 12N hydrochloric acid and 30 g of water was added to the reaction solution, which was concentrated. Then 30 g of dichloromethane was added to the concentrate whereupon the organic layer was separated. The organic layer was then washed with 20 g of water, after which dichloromethane was distilled off in vacuum. 20 g of methyl isobutyl ketone was added to the residue, whereupon the methyl isobutyl ketone was distilled off in vacuum. Ether was added to the residue. Decantation and vacuum drying gave the target compound. Brown oil, 6.52 g (yield 87%). The target compound had the structure shown below.

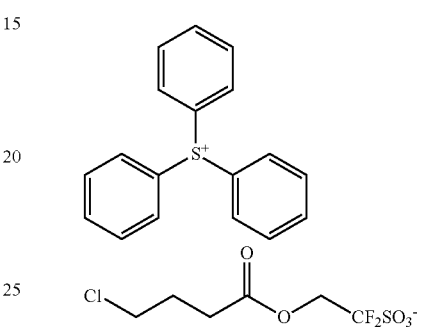

Figure 6:
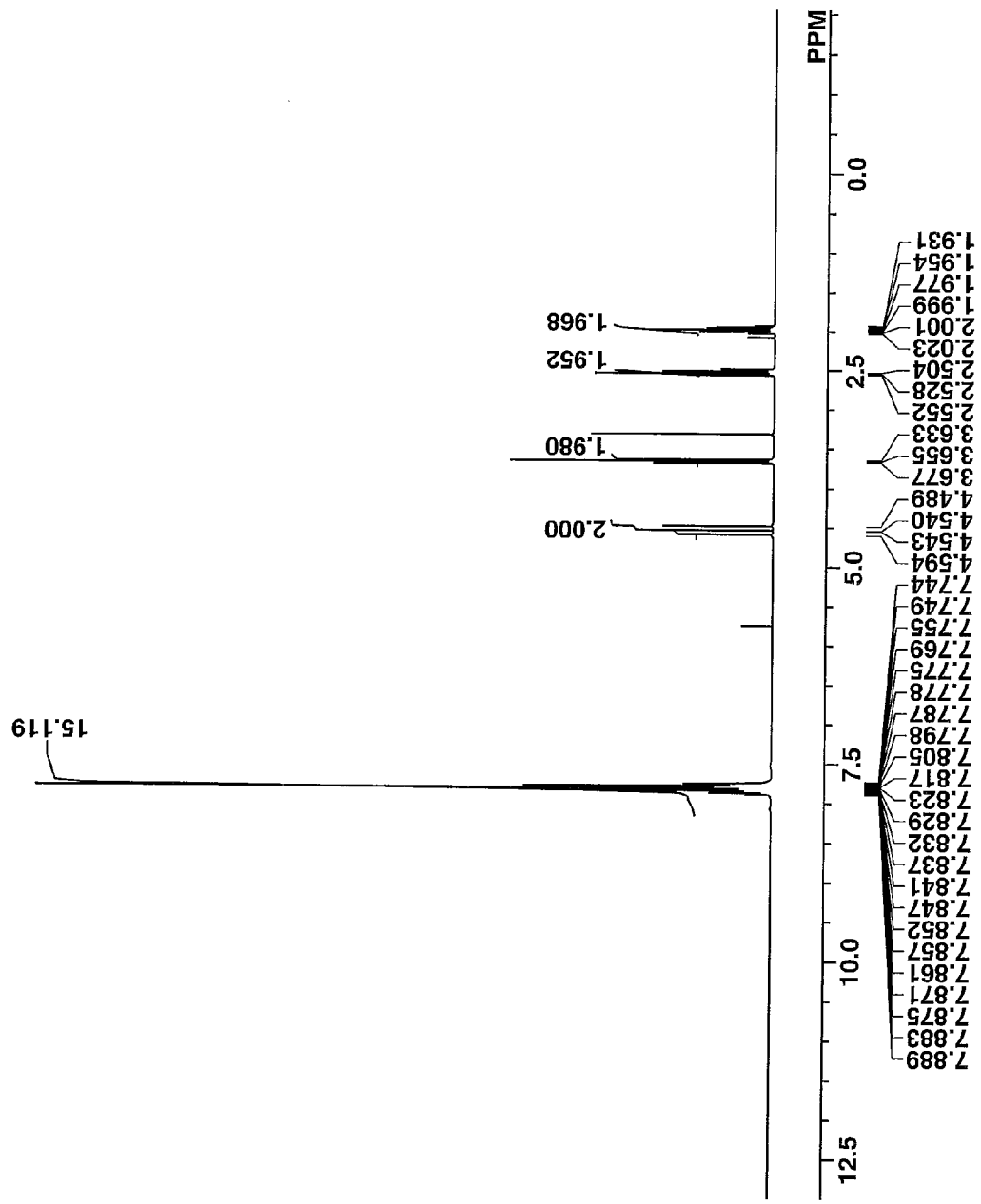
FIG. 6 is a diagram showing the $^1$H-NMR/DMSO-$d_6$ spectrum of PAG intermediate 1 in Synthesis Example 1-34.
Figure 7:
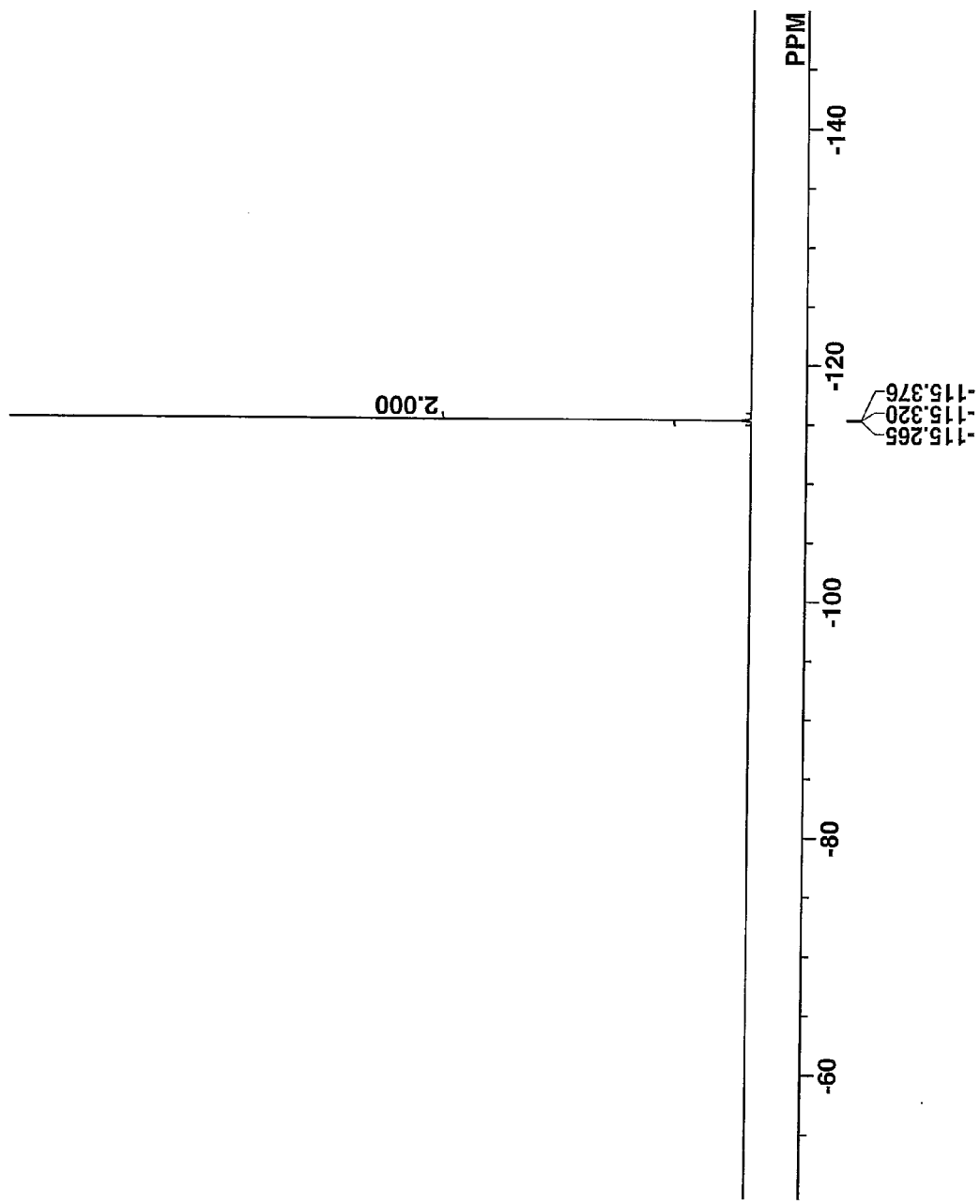
FIG. 7 is a diagram showing the $^{19}$F-NMR/DMSO-$d_6$ spectrum of PAG intermediate 1 in Synthesis Example 1-34.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 6 and 7. In $^1$H-NMR analysis, a minute amount of water was observed.

IR spectra (KBr, cm$^{-1}$): 3436, 3062, 1745, 1477, 1448, 1255, 1178, 1132, 1105, 997, 946, 750, 684, 642, 551, 524, 503

TOFMS (MALDI): Positive M$^+$263 (corresponding to $(C_6H_5)_3S^+$)

Negative M$^-$265 (corresponding to CH$_2$(OCO—C$_3$H$_6$Cl) CF$_2$SO$_3^-$)

Synthesis Example 1-35

Synthesis of triphenylsulfonium 1,1-difluorosulfoethyl 2-(adamantane-1-carbonyloxy)butanoate [PAG-D]

To 60 g of dimethylformamide were added 9.7 g (0.02 mole) of triphenylsulfonium 2-(4-chlorobutyryloxy)-1,1-difluoroethanesulfonate in Synthesis Example 1-34, 4.5 g (0.02 mole) of sodium adamantane-1-carboxylate, and 0.6 g (0.004 mole) of sodium iodide. The reaction solution was heated and stirred at 90° C. for 15 hours. The solution was allowed to cool to room temperature, after which 150 g of water and 300 g of dichloromethane were added. The organic layer was separated and washed with water, then with dilute hydrochloric acid, and again with water. Following the washing, the organic layer was distilled in vacuum. 30 g of methyl isobutyl ketone was added to the residue. The residual water and methyl isobutyl ketone were azeotroped off. The residue was washed with diisopropyl ether and dried in vacuum, obtaining the target compound. Brown oil, 11.9 g (yield 96%). The target compound had the structure shown below.

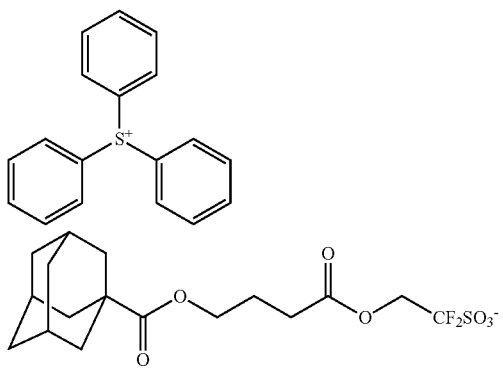

Figure 8:
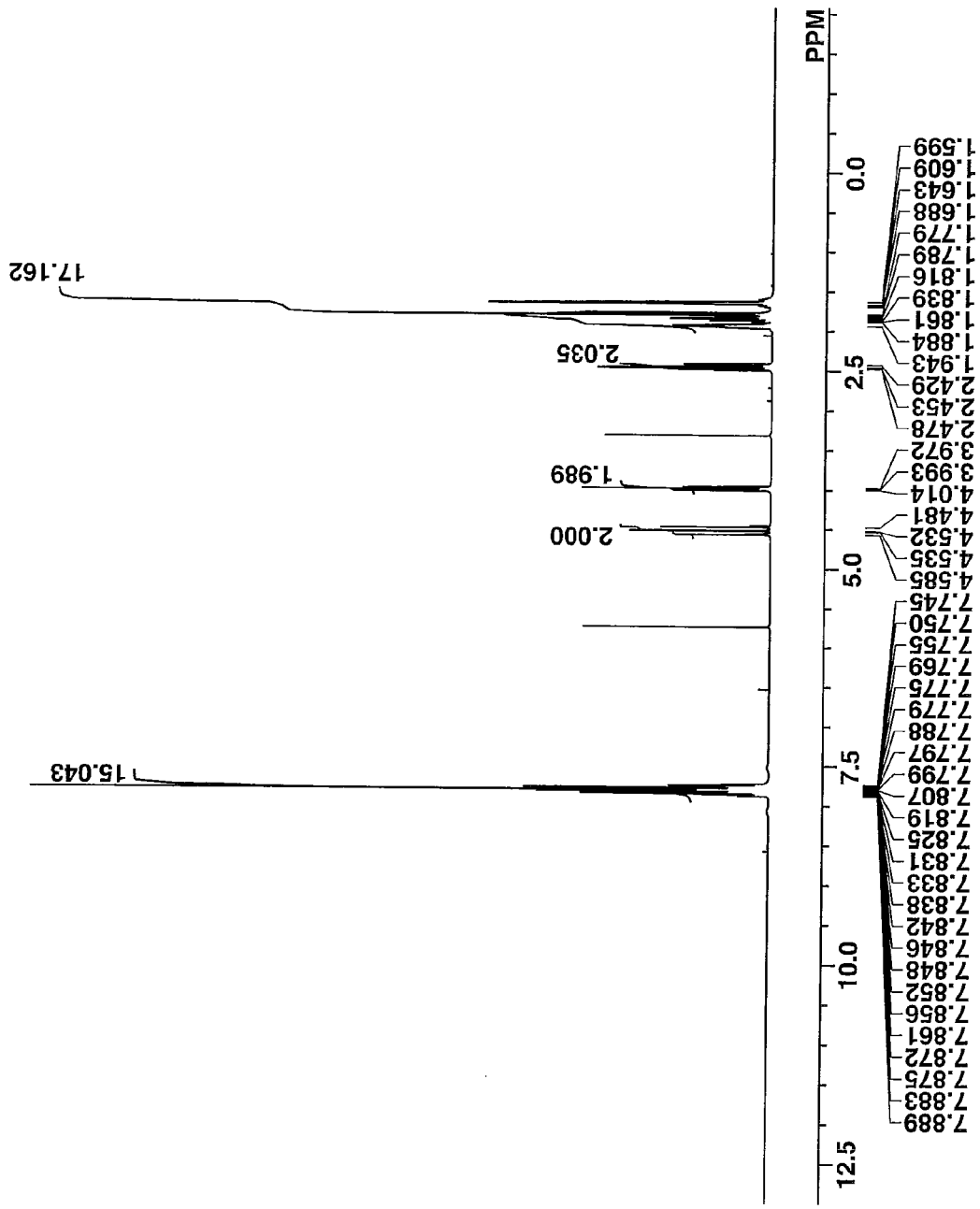
FIG. 8 is a diagram showing the $^1$H-NMR/DMSO-$d_6$ spectrum of PAG-D in Synthesis Example 1-35.
Figure 9:
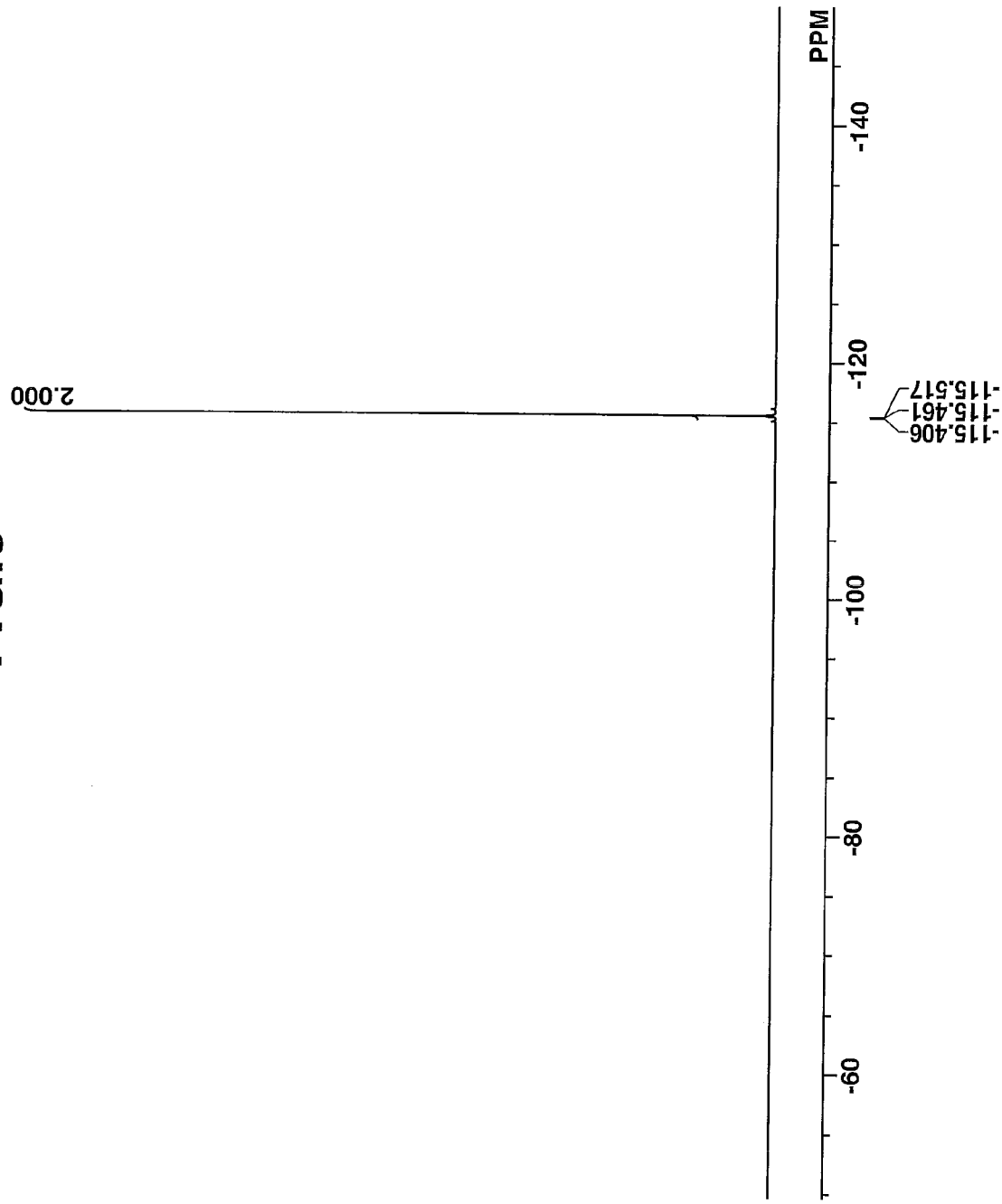
FIG. 9 is a diagram showing the $^{19}$F-NMR/DMSO-$d_6$ spectrum of PAG-D in Synthesis Example 1-35.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 8 and 9. In $^1$H-NMR analysis, minute amounts of residual solvents (methylene chloride, water) was observed.

IR spectra (KBr, cm$^{-1}$): 2904, 2851, 1743, 1715, 1476, 1446, 1323, 1232, 1182, 1159, 1129, 1102, 1073, 994, 946, 747, 682, 636

TOFMS (MALDI): Positive M$^+$263 (corresponding to $(C_6H_5)_3S^+$)

Negative M$^-$409 (corresponding to $(C_{14}H_{21}O_2$—$CO_2)CH_2CF_2SO_3^-$)

Analogous compounds were synthesized by following the successive procedures of Synthesis Examples 1-34 and 1-35 aside from using one of PAG2 to PAG8 instead of PAG1, i.e., triphenylsulfonium 2-hydroxy-1,1-difluoroethanesulfonate. The compounds correspond to PAG-D wherein the cation is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)-iodonium, dimethylphenylsulfonium, and phenacyltetrahydrothiophenium.

Synthesis Example 1-36

Synthesis of 4-tert-butylphenyldiphenylsulfonium 1-(difluorosulfomethyl)-2,2,2-trifluoroethyl 2-(adamantane-1-carbonyloxy)acetate [PAG-E]

By forming t-butyl 2-(adamantane-1-carbonyloxy)acetate from 1-adamantanecarboxylic acid and t-butyl chloroacetate and effecting deprotection reaction with acid and subsequent reaction with oxalyl chloride, there was synthesized 2-(adamantane-1-carbonyloxy)acetic chloride.

In 40 g of dichloromethane were dissolved 10.9 g (0.02 mole) of 4-tert-butylphenyldiphenylsulfonium 2-hydroxy-1,1,3,3,3-pentafluoropropane-1-sulfonate in Synthesis Example 1-24, 2.2 g (0.022 mole) of triethylamine, and 0.24 g (0.002 mole) of N,N-dimethylaminopyridine. While the solution was ice cooled, 5.6 g (0.022 mole) of 2-(adamantane-1-carbonyl-oxy)acetic chloride synthesized above was added at a temperature below 5° C. Stirring was continued for 1 hour at room temperature. Thereafter, a dilute hydrochloric acid aqueous solution prepared from 3 g of 12N hydrochloric acid and 10 g of water was added, and 80 g of methyl isobutyl ketone and 20 g of water added. The organic layer was separated and washed twice with 50 g of water, after which the solvent was distilled off in vacuum. The residue was washed with diisopropyl ether, obtaining the target compound. Colorless oil, 11.9 g (yield 78%). The target compound had the following structure.

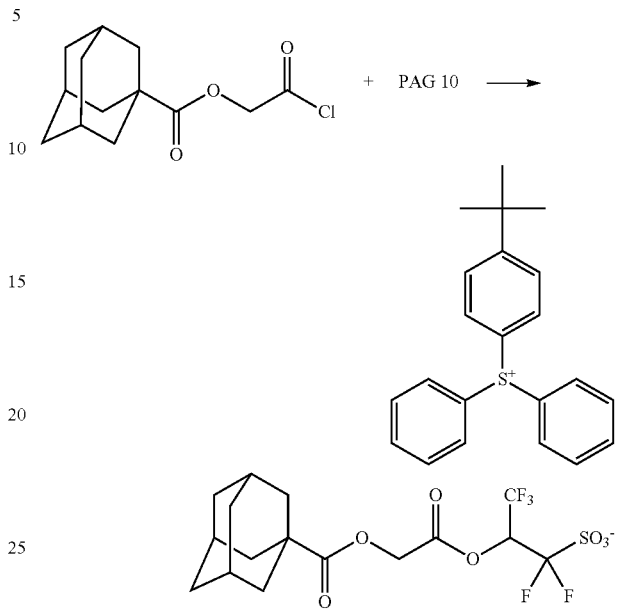

Figure 10:
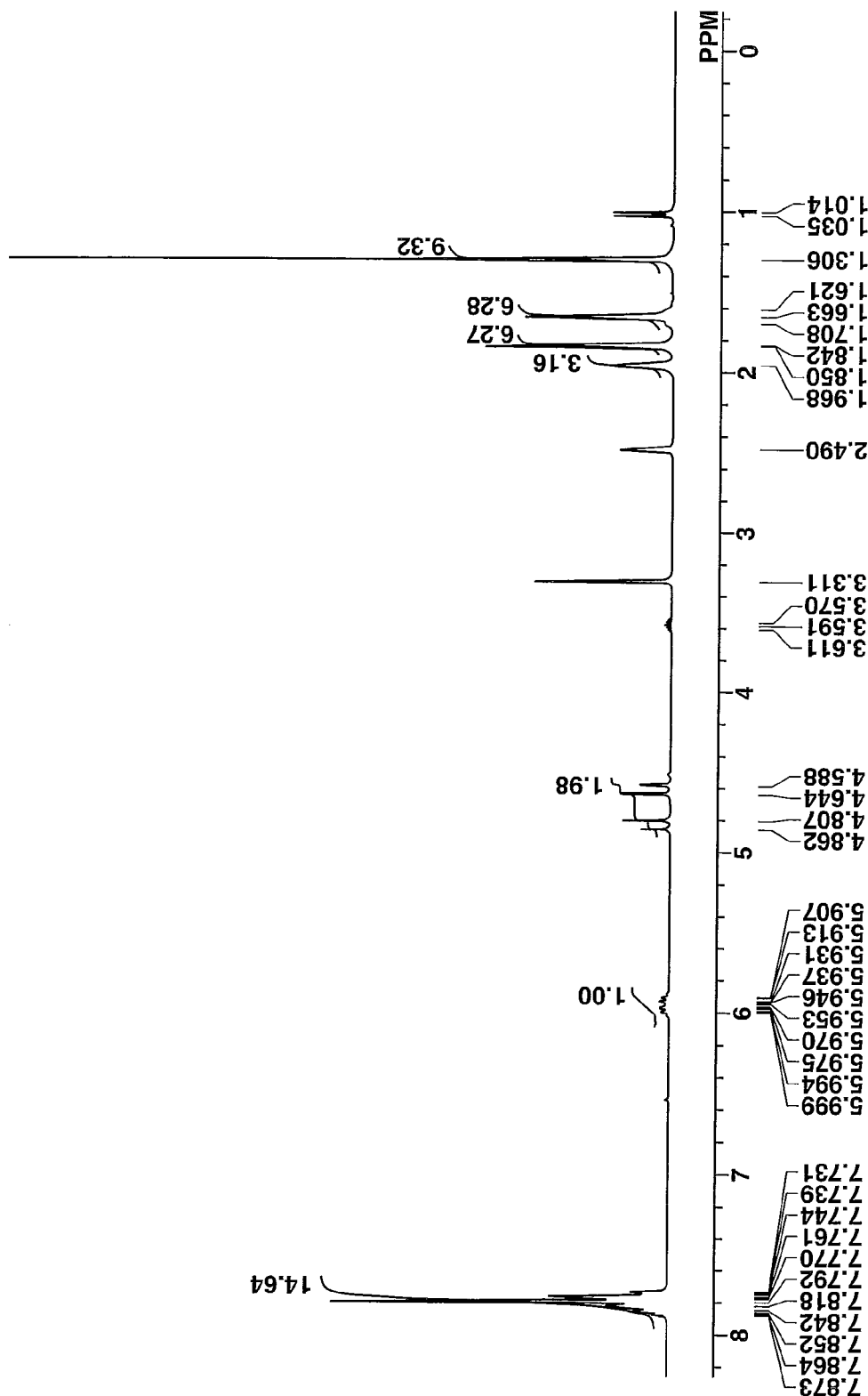
FIG. 10 is a diagram showing the $^1$H-NMR/DMSO-$d_6$ spectrum of PAG-E in Synthesis Example 1-36.
Figure 11:
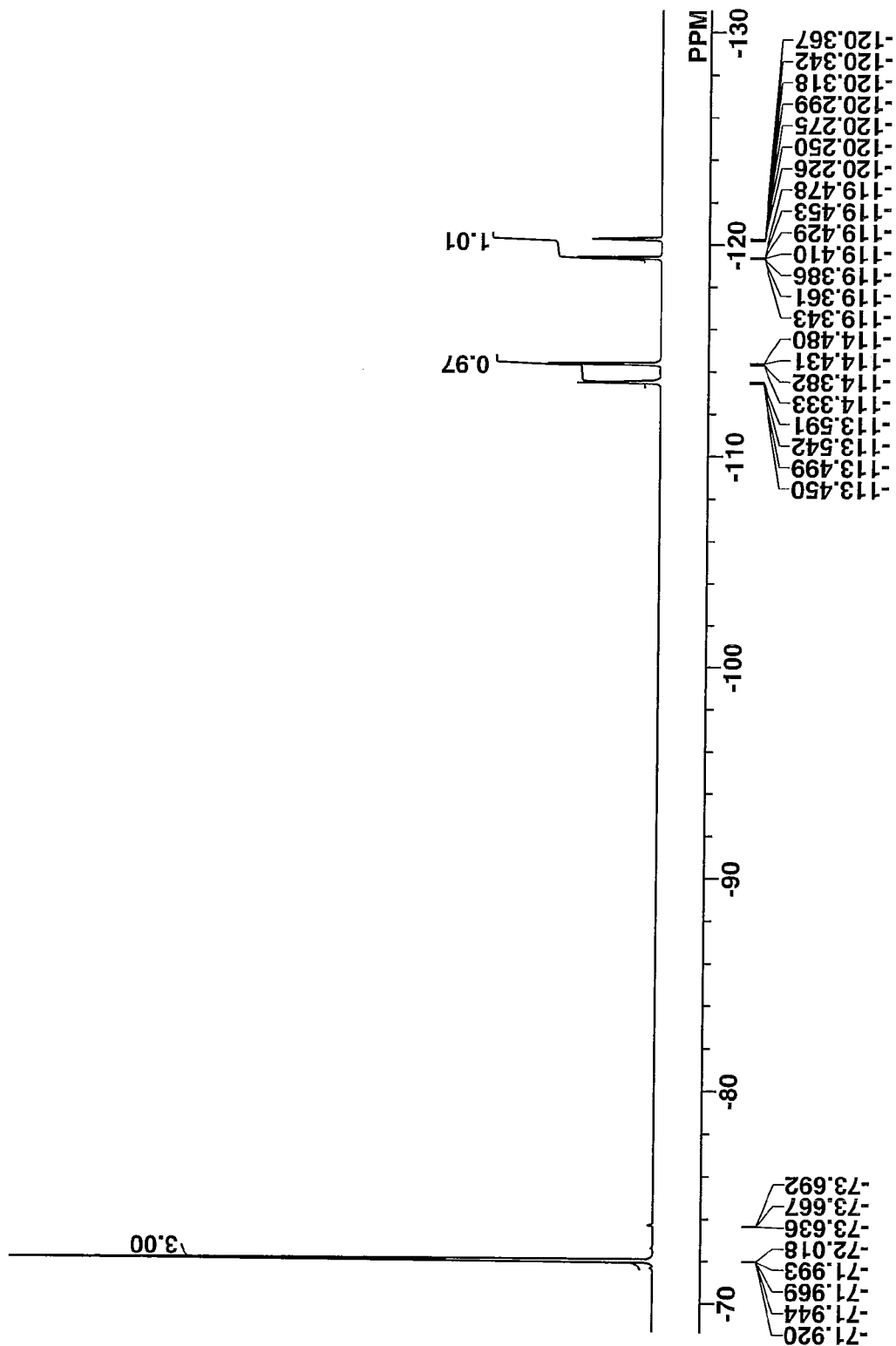
FIG. 11 is a diagram showing the $^{19}$F-NMR/DMSO-$d_6$ spectrum of PAG-E in Synthesis Example 1-36.

The compound was analyzed by spectroscopy. The nuclear magnetic resonance spectra, $^1$H-NMR and $^{19}$F-NMR/DMSO-$d_6$ are shown in FIGS. 10 and 11. In $^1$H-NMR, traces of residual solvents (diisopropyl ether, water) were observed. The data of time-of-flight mass spectrometry (TOFMS) are also shown below.

IR spectra (KBr, cm$^{-1}$): 2965, 2906, 2853, 1799, 1788, 1735, 1477, 1446, 1368, 1246, 1216, 1174, 1104, 1092, 1070, 993, 834, 749, 684, 640

TOFMS (MALDI): Positive M$^+$319 (corresponding to $(C_4H_9)C_6H_4(C_6H_5)_2S^+$)

Negative M$^-$449 (corresponding to $(C_{11}H_{15}O_3$—$CH_2CO_2)CH(CF_3)CF_2SO_3^-$)

Polymers for use in the resist compositions of the invention were synthesized in accordance with the following formulation.

Synthesis Example 2-1

Synthesis of Polymer 1

In a nitrogen atmosphere, 7.1 g of 3-hydroxy-1-adamantyl methacrylate, 11.0 g of 3-ethyl-3-exo-tetracyclo-[4.4.0.1$^{2,5}$.1$^{7,10}$]dodecyl methacrylate, 6.7 g of 4,8-dioxa-tricyclo [4.2.1.0$^{3,7}$]nonan-5-on-2-yl methacrylate, and 0.9 g of dimethyl 2,2'-azobisisobutyrate were dissolved in 72.8 g of methyl ethyl ketone. While 20.7 g of methyl ethyl ketone was stirred at 80° C. in a nitrogen atmosphere, the solution was added dropwise thereto over 4 hours. After the completion of dropwise addition, the polymerization solution was stirred for a further 2 hours while maintaining the temperature of 80° C., and thereafter, cooled down to room temperature. The polymerization solution was added dropwise to 400 g of hexane whereupon solids precipitated out. The precipitate was collected by filtration, washed twice with a mixture of 45 g of methyl ethyl ketone and 195 g of hexane, and vacuum dried at 50° C. for 20 hours, obtaining a polymer in white powder solid form. Polymer 1 weighed 23.6 g (yield 95%). Mw was determined by GPC versus polystyrene standards.

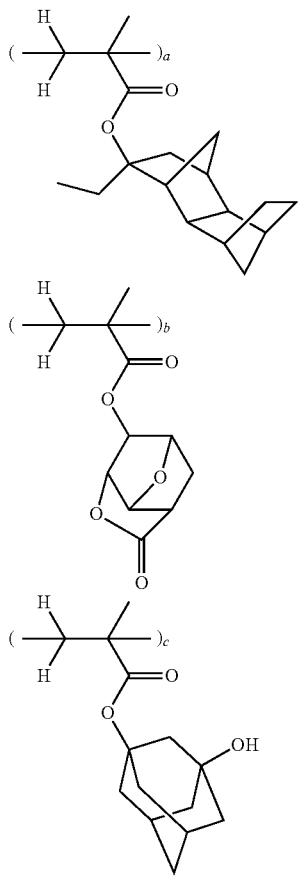

Polymer 1

(a = 0.40, b = 0.30, c = 0.30, Mw = 8,000)

Synthesis Examples 2-2 to 2-24

Synthesis of Polymers 2 to 24

A series of resins as shown in Table 1 were prepared by the same procedure as in Synthesis Example 2-1 except that the type and ratio of monomers were changed. The units in Table 1 have the structure shown in Tables 2 to 5. In Table 1, the ratio of units incorporated is a molar ratio.

Synthesis Examples 2-25 to 2-28

Synthesis of Polymers 25 to 28

Each of Polymers 21 to 24 obtained by the above formulation was dissolved in a solvent mixture of methanol and tetrahydrofuran, to which oxalic acid was added. Deprotection reaction took place at 40° C. The solution was neutralized with pyridine and purified by a standard reprecipitation technique, obtaining a polymer comprising hydroxystyrene units.

Synthesis Examples 2-29 to 2-31

Synthesis of Polymers 29 to 31

Polymer 26 was reacted with ethyl vinyl ether under acidic conditions or with 1-chloro-1-methoxy-2-methylpropane under basic conditions, obtaining Polymer 29. Similarly, each of Polymer 26 and Polymer 25 was reacted with 8-(1-chloro-2-methyl-propoxy)-tricyclo[5.2.1.0$^{2,6}$]decane under basic condition, obtaining each of Polymer 31 and Polymer 30.

With respect to the deprotection and protection of polyhydroxystyrene derivatives in Synthesis Examples 2-25 to 2-31, reference should be made to JP-A 2004-115630 and JP-A 2005-008766.

Polymers 1 to 31 are designated P-01 to P-31, respectively.

TABLE 1

|  | Resin | Unit 1 (ratio) | Unit 2 (ratio) | Unit 3 (ratio) | Unit 4 (ratio) | Unit 5 (ratio) |
|---|---|---|---|---|---|---|
| Synthesis 2-1 | P-01 | A-1M (0.40) | B-1M (0.30) | B-4M (0.30) | — | — |
| Example 2-2 | P-02 | A-2M (0.60) | B-4M (0.40) | — | — | — |
| 2-3 | P-03 | A-2M (0.40) | B-1M (0.25) | B-4M (0.35) | — | — |
| 2-4 | P-04 | A-2M (0.35) | B-1M (0.35) | B-3M (0.30) | — | — |
| 2-5 | P-05 | A-1M (0.35) | B-1M (0.25) | B-5M (0.40) | — | — |
| 2-6 | P-06 | A-3M (0.30) | B-1M (0.25) | B-4M (0.45) | — | — |
| 2-7 | P-07 | A-1M (0.60) | B-2M (0.20) | B-4M (0.20) | — | — |
| 2-8 | P-08 | A-1M (0.25) | B-1M (0.25) | B-4M (0.40) | A-2M (0.10) | — |
| 2-9 | P-09 | A-1M (0.25) | B-1M (0.25) | B-4M (0.40) | C-2M (0.10) | — |
| 2-10 | P-10 | A-4M (0.25) | B-1M (0.25) | B-4M (0.40) | C-2M (0.10) | — |
| 2-11 | P-11 | A-1M (0.30) | B-1M (0.25) | B-4M (0.35) | C-3M (0.10) | — |
| 2-12 | P-12 | A-4M (0.30) | B-1M (0.25) | B-4M (0.35) | C-3M (0.10) | — |
| 2-13 | P-13 | A-5M (0.30) | B-1M (0.25) | B-4M (0.35) | C-3M (0.10) | — |
| 2-14 | P-14 | A-1M (0.25) | B-1M (0.25) | B-4M (0.40) | C-1M (0.10) | — |
| 2-15 | P-15 | A-5M (0.25) | B-1M (0.25) | B-4M (0.40) | C-1M (0.10) | — |
| 2-16 | P-16 | A-3M (0.35) | B-1M (0.25) | B-4M (0.30) | C-1M (0.10) | — |
| 2-17 | P-17 | A-1M (0.25) | B-1M (0.15) | B-4M (0.40) | A-5M (0.20) | — |
| 2-18 | P-18 | A-1M (0.25) | B-1M (0.25) | B-7M (0.40) | B-8M (0.10) | — |
| 2-19 | P-19 | A-1M (0.20) | B-1M (0.25) | B-4M (0.35) | A-5M (0.10) | C-1M (0.10) |
| 2-20 | P-20 | A-1M (0.15) | B-1M (0.15) | B-7M (0.25) | B-8M (0.20) | A-5M (0.25) |
| 2-21 | P-21 | D-2 (0.90) | D-5 (0.10) | — | — | — |
| 2-22 | P-22 | D-2 (0.90) | D-6 (0.10) | — | — | — |
| 2-23 | P-23 | D-2 (0.70) | D-5 (0.10) | D-3 (0.20) | — | — |
| 2-24 | P-24 | D-2 (0.80) | D-5 (0.10) | D-4 (0.10) | — | — |
| 2-25 | P-25 | D-1 (0.90) | D-5 (0.10) | — | — | — |
| 2-26 | P-26 | D-1 (0.90) | D-6 (0.10) | — | — | — |
| 2-27 | P-27 | D-1 (0.70) | D-5 (0.10) | D-3 (0.20) | — | — |
| 2-28 | P-28 | D-1 (0.80) | D-5 (0.10) | D-4 (0.10) | — | — |

TABLE 1-continued
| Resin | Unit 1 (ratio) | Unit 2 (ratio) | Unit 3 (ratio) | Unit 4 (ratio) | Unit 5 (ratio) |
|---|---|---|---|---|---|
| 2-29 | P-29 | D-1 (0.70) | D-6 (0.10) | D-7 (0.20) | — | — |
| 2-30 | P-30 | D-1 (0.70) | D-5 (0.10) | D-8 (0.20) | — | — |
| 2-31 | P-31 | D-1 (0.70) | D-6 (0.10) | D-8 (0.20) | — | — |
TABLE 2
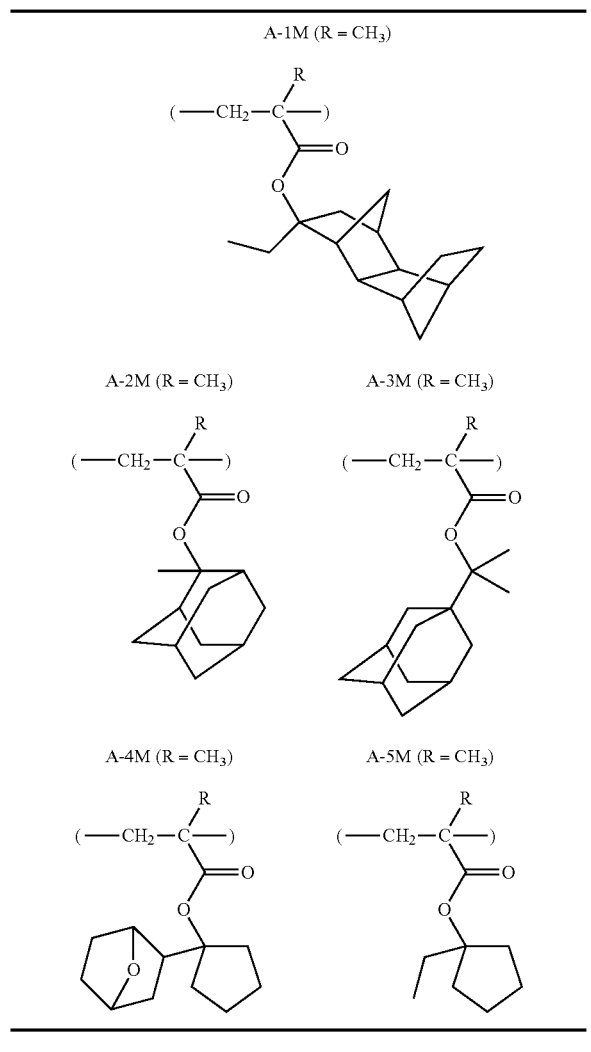
TABLE 3
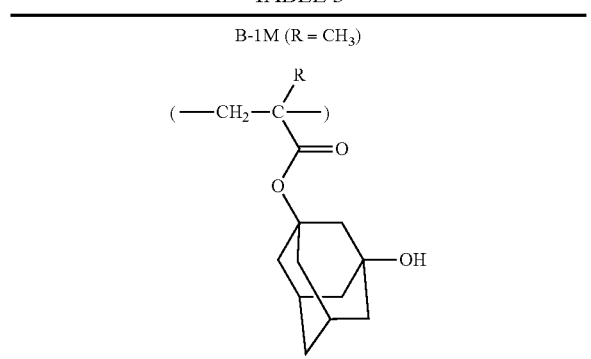
TABLE 3-continued
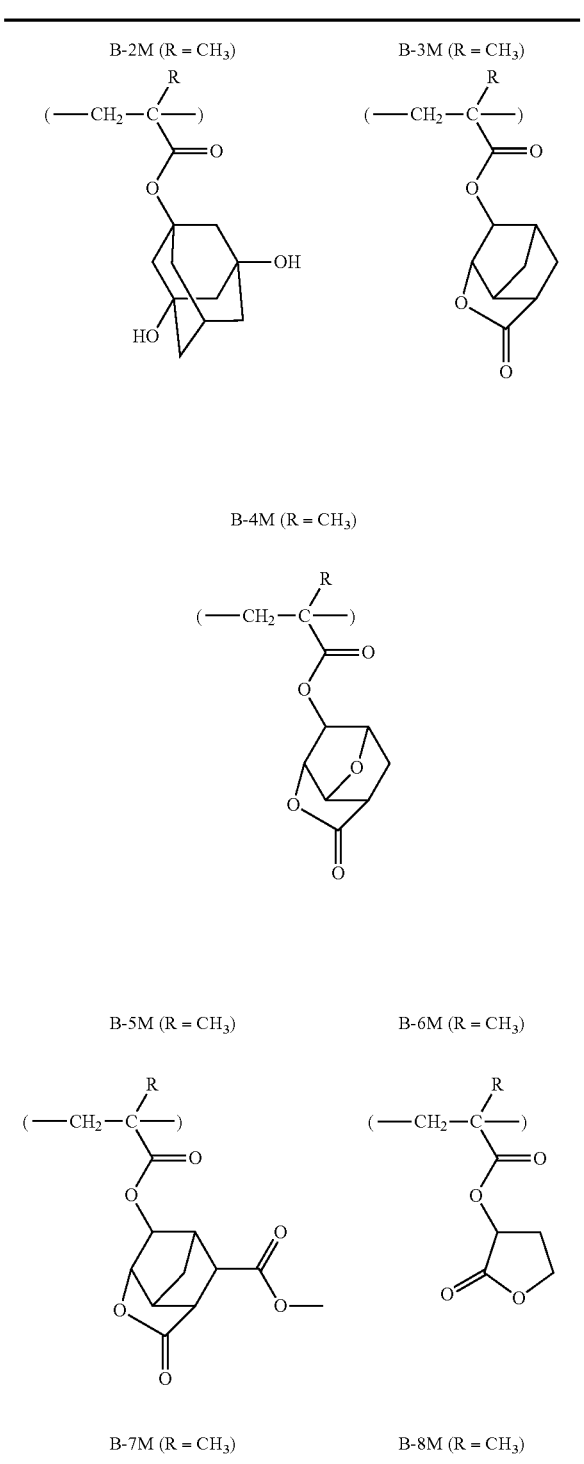

TABLE 3-continued

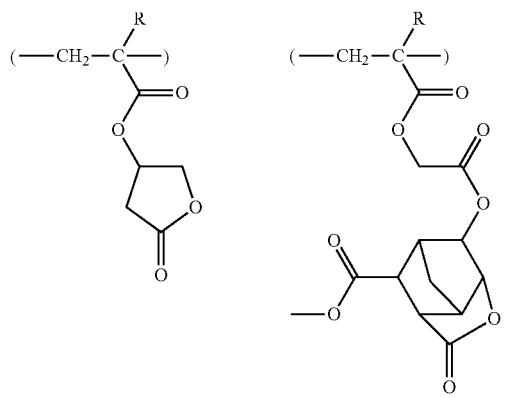
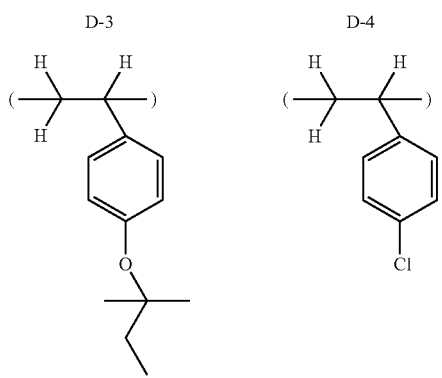

TABLE 4

C-1M (R = CH₃)    C-2M (R = CH₃)

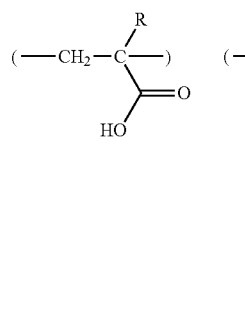
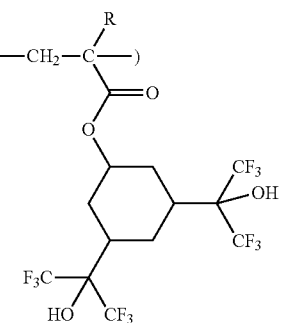

C-3M (R = CH₃)

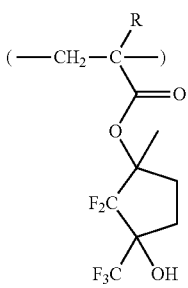

TABLE 5

D-1    D-2

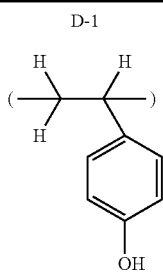
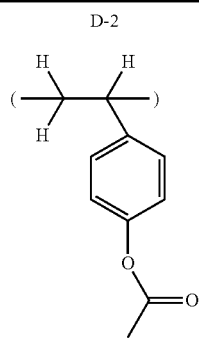

TABLE 5-continued

D-3    D-4

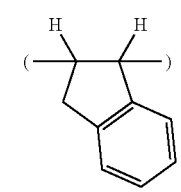
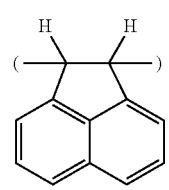

D-5    D-6

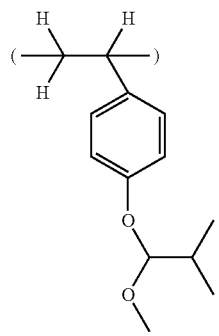

D-7    D-8

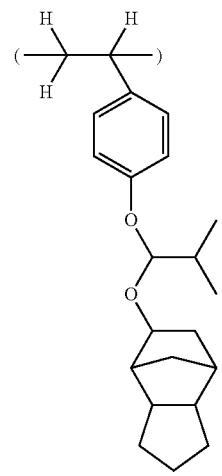

Examples 1-1 to 1-20 & Comparative Examples 1-1 to 1-4

Preparation of Resist Composition

Resist compositions were prepared by dissolving the polymers prepared above as a base resin, the photoacid generators synthesized above, and a quencher (or base) in a solvent according to the formulation shown in Table 6. They were filtered through a Teflon® filter having a pore size of 0.2 μm, giving inventive resist solutions (R-01 to 20) and comparative resist solutions (R-21 to 24). Note that the solvent contained 0.01 wt % of a surfactant (Surfactant 1).

In Table 6, the solvents, quenchers, photoacid generators (in Comparative Examples), and acid crosslinker are shown below.

PGMEA: propylene glycol monomethyl ether acetate
CyHO: cyclohexanone
EL: ethyl lactate Base-1: 2-morpholinoethyl laurate
Base-2: tris[2-(methoxymethoxy)ethyl]amine
PAG-α: triphenylsulfonium perfluoro-1-butanesulfonate
PAG-β: triphenylsulfonium 2-(adamantane-1-carbonyloxy)-1,1,3,3,3-pentafluoropropane-1-sulfonate (described in JP-A 2007-145797)
TMGU: 1,3,4,6-tetramethoxymethylglycoluril
Surfactant 1: 3-methyl-3-(2,2,2-trifluoroethoxymethyl)oxetane/tetrahydrofuran/2,2-dimethyl-1,3-propane diol copolymer (Omnova Solutions, Inc.)

wafer was exposed by means of an ArF excimer laser scanner NSR-S307E (Nikon Corp., NA 0.85, 4/5 annular illumination, 6% halftone phase shift mask), post-exposure baked (PEB) for 60 seconds, and developed with a 2.38 wt % tetramethylammonium hydroxide aqueous solution for 60 seconds. A proper PEB temperature is shown in Table 7.

The optimum exposure (Eop) was defined as the exposure dose (mJ/cm$^2$) which provided a 1:1 resolution at the top and bottom of a 80-nm grouped line-and-space pattern. The maximum resolution of the resist was defined as the minimum line

TABLE 6

|  |  | Resist composition | Resin (pbw) | PAG (pbw) | Base (pbw) | Solvent 1 (pbw) | Solvent 2 (pbw) |
|---|---|---|---|---|---|---|---|
| Example | 1-1 | R-01 | P-01 (80) | PAG-A (11.0) | Base-2 (1.41) | PGMEA (1,700) | CyHO (700) |
|  | 1-2 | R-02 | P-01 (80) | PAG-B (11.3) | Base-2 (1.41) | PGMEA (1,700) | CyHO (700) |
|  | 1-3 | R-03 | P-01 (80) | PAG-C (10.2) | Base-2 (1.41) | PGMEA (1,700) | CyHO (700) |
|  | 1-4 | R-04 | P-01 (80) | PAG-D (10.4) | Base-2 (1.41) | PGMEA (1,700) | CyHO (700) |
|  | 1-5 | R-05 | P-01 (80) | PAG-E (11.9) | Base-2 (1.41) | PGMEA (1,700) | CyHO (700) |
|  | 1-6 | R-06 | P-09 (80) | PAG-A (11.0) | Base-2 (1.41) | PGMEA (1,700) | CyHO (700) |
|  | 1-7 | R-07 | P-10 (80) | PAG-B (11.3) | Base-2 (1.41) | PGMEA (1,700) | CyHO (700) |
|  | 1-8 | R-08 | P-11 (80) | PAG-C (10.2) | Base-2 (1.41) | PGMEA (1,700) | CyHO (700) |
|  | 1-9 | R-09 | P-12 (80) | PAG-D (10.4) | Base-2 (1.41) | PGMEA (1,700) | CyHO (700) |
|  | 1-10 | R-10 | P-13 (80) | PAG-A (11.0) | Base-2 (1.41) | PGMEA (1,700) | CyHO (700) |
|  | 1-11 | R-11 | P-14 (80) | PAG-A (11.0) | Base-1 (1.58) | PGMEA (1,700) | CyHO (700) |
|  | 1-12 | R-12 | P-15 (80) | PAG-A (11.0) | Base-1 (1.58) | PGMEA (1,700) | CyHO (700) |
|  | 1-13 | R-13 | P-16 (80) | PAG-A (11.0) | Base-1 (1.58) | PGMEA (1,700) | CyHO (700) |
|  | 1-14 | R-14 | P-18 (80) | PAG-A (11.0) | Base-1 (1.58) | PGMEA (1,700) | CyHO (700) |
|  | 1-15 | R-15 | P-19 (80) | PAG-A (11.0) | Base-1 (1.58) | PGMEA (1,700) | CyHO (700) |
|  | 1-16 | R-16 | P-20 (80) | PAG-A (11.0) | Base-1 (1.58) | PGMEA (1,700) | CyHO (700) |
|  | 1-17 | R-17 | P-27 (80) | PAG-A (8.3) | Base-2 (1.10) | PGMEA (540) | EL (1,280) |
|  | 1-18 | R-18 | P-28 (80) | PAG-A (8.3) | Base 2 (1.10) TMGU (10.0) | PGMEA (540) | EL (1,280) |
|  | 1-19 | R-19 | P-29 (80) | PAG-A (8.3) | Base-2 (1.10) | PGMEA (540) | EL (1,280) |
|  | 1-20 | R-20 | P-30 (80) | PAG-A (8.3) | Base-2 (1.10) | PGMEA (540) | EL (1,280) |
| Comparative | 1-1 | R-21 | P-01 (80) | PAG-α (8.7) | Base-1 (1.58) | PGMEA (1,700) | CyHO (700) |
| Example | 1-2 | R-22 | P-17 (80) | PAG-β (10.1) | Base-1 (1.58) | PGMEA (1,700) | CyHO (700) |
|  | 1-3 | R-23 | P-20 (80) | PAG-β (10.1) | Base-1 (1.58) | PGMEA (1,700) | CyHO (700) |
|  | 1-4 | R-24 | P-27 (80) | PAG-α (6.5) | Base-2 (1.41) | PGMEA (540) | EL (1,280) |

Examples 2-1 to 2-16 & Comparative Examples 2-1 to 2-3

Evaluation of Resolution, Exposure Latitude and Line Width Roughness on ArF Lithography On a silicon substrate, an antireflective coating solution (ARC-29A, Nissan Chemical Co., Ltd.) was coated and baked at 200° C. for 60 seconds to form an ARC of 78 nm thick. Each of inventive resist compositions (R-01 to 16) and comparative resist compositions (R-21 to 23) was spin coated on the ARC-coated silicon substrate and baked on a hot plate for 60 seconds, forming a resist film of 100 nm thick. The width (nm) of a line-and-space pattern that was resolved and separated at the optimum exposure. For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude. The line width roughness (LWR) of a 80-nm line-and-space pattern was measured using measurement SEM (S-9380 by Hitachi Hitechnologies, Ltd.). The results are shown in Table 7.

TABLE 7

|  |  | Resist composition | Optimum exposure (mJ/cm$^2$) | Maximum Resolution (nm) | Exposure latitude (%) | LWR (nm) | PEB (° C.) |
|---|---|---|---|---|---|---|---|
| Example | 2-1 | R-01 | 31 | 70 | 13.9 | 5.2 | 115 |
|  | 2-2 | R-02 | 32 | 75 | 13.5 | 5.3 | 115 |
|  | 2-3 | R-03 | 30 | 70 | 14.0 | 5.4 | 115 |
|  | 2-4 | R-04 | 34 | 75 | 13.7 | 5.1 | 115 |
|  | 2-5 | R-05 | 42 | 70 | 14.9 | 5.4 | 115 |
|  | 2-6 | R-06 | 33 | 75 | 14.4 | 4.6 | 110 |
|  | 2-7 | R-07 | 32 | 70 | 13.8 | 4.6 | 110 |
|  | 2-8 | R-08 | 31 | 70 | 14.0 | 4.9 | 110 |
|  | 2-9 | R-09 | 33 | 75 | 13.9 | 4.8 | 110 |
|  | 2-10 | R-10 | 35 | 75 | 13.8 | 4.2 | 120 |
|  | 2-11 | R-11 | 31 | 70 | 14.2 | 4.9 | 110 |
|  | 2-12 | R-12 | 32 | 70 | 13.6 | 4.3 | 110 |

TABLE 7-continued

|  | Resist composition | Optimum exposure (mJ/cm$^2$) | Maximum Resolution (nm) | Exposure latitude (%) | LWR (nm) | PEB (° C.) |
|---|---|---|---|---|---|---|
| 2-13 | R-13 | 34 | 75 | 14.7 | 4.8 | 120 |
| 2-14 | R-14 | 36 | 70 | 14.1 | 5.0 | 90 |
| 2-15 | R-15 | 33 | 75 | 14.7 | 4.4 | 110 |
| 2-16 | R-16 | 30 | 70 | 13.8 | 4.2 | 90 |
| Comparative 2-1 | R-21 | 33 | 80 | 11.0 | 7.5 | 115 |
| Example 2-2 | R-22 | 30 | 80 | 11.7 | 8.2 | 110 |
| 2-3 | R-23 | 37 | 80 | 10.8 | 7.5 | 90 |

The data of Examples in Table 7 demonstrate that the inventive resist compositions exhibit high resolution performance, good exposure latitude and low LWR values when processed by ArF lithography and are thus suited for precise micropatterning.

Examples 3-1 to 3-4 & Comparative Example 3-1

Evaluation of Resolution on EB Lithography

Using a coater/developer system Clean Track ACT-M (Tokyo Electron Ltd.), each of the resist compositions (R-17 to 20) or comparative resist composition (R-24) was spin-coated onto a 152-mm square mask blank having a chromium oxynitride film at the outermost surface and pre-baked on a hot plate at 100° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB mask writer system EBM-5000Plus (NuFlare Technology Inc., accelerating voltage 50 keV), then baked (PEB) at 100° C. for 600 seconds, and developed with a 2.38 wt % tetramethylammonium hydroxide aqueous solution, thereby yielding positive patterns.

The patterned wafer was observed under a top-down scanning electron microscope (TDSEM). The optimum exposure (Eop) was defined as the exposure dose (μC/cm$^2$) which provided a 1:1 resolution at the top and bottom of a 100-nm 1:1 line-and-space pattern. The maximum resolution of the resist was defined as the minimum line width of a line-and-space pattern that could be resolved and separated at the optimum exposure. On observation in cross section of the resist pattern under SEM, it was visually judged whether or not the pattern profile was rectangular. The post-exposure delay (PED) in vacuum was evaluated by exposing the coated wafer on the EB lithography system, holding it in the vacuum system for 24 hours, thereafter effecting PEB and development. The line width of a 100-nm line-and-space pattern at Eop was measured and compared with that of the resist pattern which was baked immediately after exposure, with a difference (in nm) being reported. The test results are shown in Table 8.

TABLE 8

|  |  | Resist composition | Eop (μC/cm$^2$) | Resolution (nm) | PED in Vacuum (nm) | Pattern profile |
|---|---|---|---|---|---|---|
| Example | 3-1 | R-17 | 22 | 45 | 3.2 | Rectangular |
|  | 3-2 | R-18 | 23 | 50 | 3.2 | Rectangular |
|  | 3-3 | R-19 | 21 | 50 | 3.8 | Rectangular |
|  | 3-4 | R-20 | 24 | 45 | 4.2 | Rectangular |
| Comparative Example | 3-1 | R-24 | 20 | 60 | 6.0 | Somewhat rounded top |

It is evident from Table 8 that the resist composition of the invention is also improved in resolution and vacuum PED when processed by EB lithography. The resist composition is expected to perform equally when processed by the EUV or KrF lithography using polyhydroxystyrene derivatives.

Japanese Patent Application No. 2009-157856 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified resist composition comprising a photoacid generator which generates a sulfonic acid having the general formula (1) in response to high-energy radiation or heat,

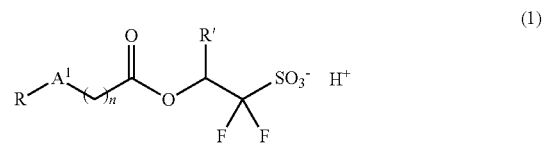

(1)

wherein

R is a substituted or unsubstituted, monovalent hydrocarbon group having an alicyclic hydrocarbon structure selected from the group consisting of cyclopentyl, cyclohexyl, cycloheptyl, 4-methylcyclohexyl, cyclohexylmethyl, norbornyl, adamantyl, 2-oxocyclopentyl, 2-oxocyclohexyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, 2-(adamantyl-1-carbonyloxy)-4-oxa-tricyclo[4.2.1.0$^{3,7}$]nonan-5-on-9-yl, and 4-oxoadamantyl, R' is hydrogen or trifluoromethyl, $A^1$ is a carbonyloxy (—COO—), ether, thioether, amide, or carbonate bond, and n is an integer of 1 to 3.

2. The resist composition of claim 1 further comprising a base resin, a quencher and an organic solvent.

3. The resist composition of claim 1 further comprising a base resin which is insoluble or substantially insoluble in a developer, but turns soluble in the developer under the action of acid, a quencher, and an organic solvent.

4. The resist composition of claim 2 wherein said base resin comprises recurring units of at least one type selected from the general formulae (11) to (15):

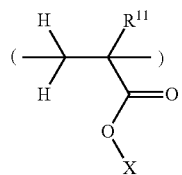
(11)

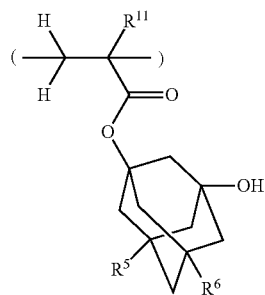
(12)

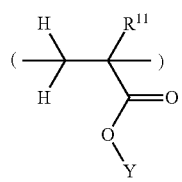
(13)

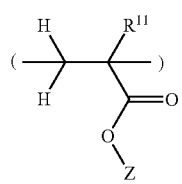
(14)

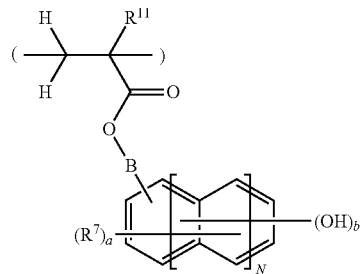
(15)

wherein $R^{11}$ is hydrogen, fluorine, methyl or trifluoromethyl, $R^5$ and $R^6$ are each independently hydrogen or hydroxyl, X is an acid labile group, Y is a substituent group of lactone structure, Z is hydrogen, $C_1$-$C_{15}$ fluoroalkyl or $C_1$-$C_{15}$ fluoroalcohol-containing substituent group, N is an integer of 0 to 2, $R^7$ is hydrogen or $C_1$-$C_{10}$ alkyl group, B is a single bond or a divalent $C_1$-$C_{10}$ organic group which may be substituted with oxygen, a is an integer of 0 to 3, and b is an integer of 1 to 3.

5. A process for forming a pattern comprising the steps of:

applying the resist composition of claim 2 onto a substrate to form a coating, heat treating the coating and exposing it to high-energy radiation or electron beam through a photomask, and heat treating and developing the exposed coating with a developer.

6. A process for forming a pattern comprising the steps of:

applying the resist composition of claim 2 onto a substrate to form a coating, heat treating the coating and exposing it to high-energy radiation or electron beam through a photomask, and heat treating and developing the exposed coating with a developer, wherein the exposing step relies on immersion lithography comprising directing radiation through a projection lens, with a high refractive index liquid having a refractive index of at least 1.0 intervening between the resist coating and the projection lens.

7. A process for forming a pattern comprising the steps of:

applying the resist composition of claim 2 onto a substrate to form a coating, heat treating the coating and exposing it to high-energy radiation or electron beam through a photomask, and heat treating and developing the exposed coating with a developer, wherein a protective film is coated on the resist coating, and the exposing step relies on immersion lithography comprising directing radiation through a projection lens, with a high refractive index liquid having a refractive index of at least 1.0 intervening between the protective film and the projection lens.

8. The resist composition of claim 1, wherein R is adamantyl or adamantyl substituted with polar groups.

9. A sulfonium salt having the general formula (2):

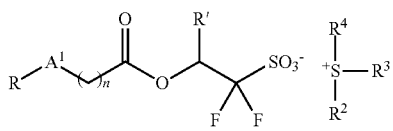

wherein
R is a substituted or unsubstituted, monovalent hydrocarbon group having an alicyclic hydrocarbon structure selected from the group consisting of cyclopentyl, cyclohexyl, cycloheptyl, 4-methylcyclohexyl, cyclohexylmethyl, norbornyl, adamantyl, 2-oxocyclopentyl, 2-oxocyclohexyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, 2-(adamantyl-1-carbonyloxy)-4-oxa-tricyclo[4.2.1.0$^{3,7}$]nonan-5-on-9-yl, and 4-oxoadamantyl, R' is hydrogen or trifluoromethyl, A$^1$ is a carbonyloxy (—COO—), ether, thioether, amide, or carbonate bond, n is an integer of 1 to 3, R$^2$, R$^3$, and R$^4$ are each independently a substituted or unsubstituted, straight or branched C$_1$-C$_{10}$ alkyl, alkenyl or oxoalkyl group or a substituted or unsubstituted C$_6$-C$_{18}$ aryl, aralkyl or aryloxoalkyl group, or at least two of R$^2$, R$^3$ and R$^4$ may bond together to form a ring with the sulfur atom.

10. The sulfonium salt of claim 9, wherein R is adamantyl or adamantyl substituted with polar groups.

11. A sulfonium salt having the general formula (3):

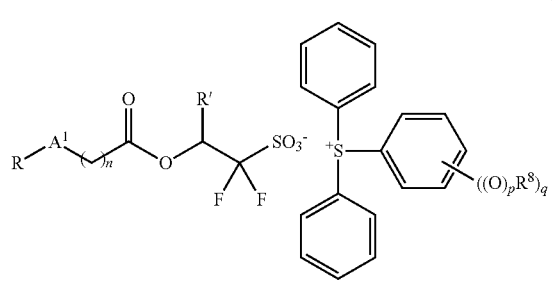

wherein
R is a substituted or unsubstituted, monovalent hydrocarbon group having an alicyclic hydrocarbon structure selected from the group consisting of cyclopentyl, cyclohexyl, cycloheptyl, 4-methylcyclohexyl, cyclohexylmethyl, norbornyl, adamantyl, 2-oxocyclopentyl, 2-oxocyclohexyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, 2-(adamantyl-1-carbonyloxy)-4-oxa-tricyclo[4.2.1.0$^{3,7}$]nonan-5-on-9-yl, and 4-oxoadamantyl, R' is hydrogen or trifluoromethyl, A$^1$ is a carbonyloxy (—COO—), ether, thioether, amide, or carbonate bond, n is an integer of 1 to 3, R$^8$ is a substituted or unsubstituted, straight, branched or cyclic C$_1$-C$_{20}$ alkyl or alkenyl group or a substituted or unsubstituted C$_6$-C$_{14}$ aryl group, p is 0 or 1, and q is an integer of 1 to 5.

12. The sulfonium salt of claim 11, wherein R is adamantyl or adamantyl substituted with polar groups.

13. An iodonium salt having the general formula (4):

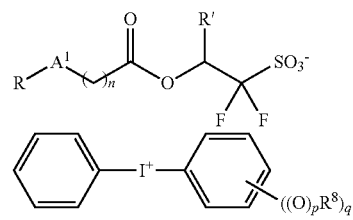

wherein
R is a substituted or unsubstituted, monovalent hydrocarbon group having an alicyclic hydrocarbon structure selected from the group consisting of cyclopentyl, cyclohexyl, cycloheptyl, 4-methylcyclohexyl, cyclohexylmethyl, norbornyl, adamantyl, 2-oxocyclopentyl, 2-oxocyclohexyl, 2-cyclopentyl-2-oxoethyl, 2-cyclohexyl-2-oxoethyl, 2-(4-methylcyclohexyl)-2-oxoethyl, 4-oxa-tricyclo[4.2.1.0$^{3,7}$]nonan-5-on-9-yl, 2-(adamantyl-1-carbonyloxy)-4-oxa-tricyclo[4.2.1.0$^{3,7}$]nonan-5-on-9-yl, and 4-oxoadamantyl, R' is hydrogen or trifluoromethyl, A$^1$ is a carbonyloxy (—COO—), ether, thioether, amide, or carbonate bond, n is an integer of 1 to 3, R$^8$ is a substituted or unsubstituted, straight, branched or cyclic C$_1$-C$_{20}$ alkyl or alkenyl group or a substituted or unsubstituted C$_6$-C$_{14}$ aryl group, p is 0 or 1, and q is an integer of 1 to 5.

14. An iodonium salt having the general formula (4):

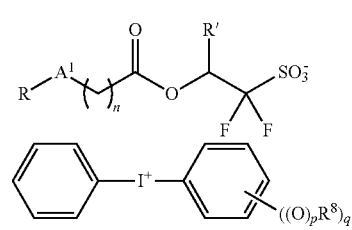

wherein
R is adamantyl or adamantyl substituted with polar groups,

R' is hydrogen or trifluoromethyl,

A$^1$ is a carbonyloxy (—COO—), ether, thioether, amide, or carbonate bond, n is an integer of 1 to 3, R$^8$ is a substituted or unsubstituted, straight, branched or cyclic C$_1$-C$_{20}$ alkyl or alkenyl group or a substituted or unsubstituted C$_6$-C$_{14}$ aryl group., p is 0 or 1, and q is an integer of 1 to 5.

15. A chemically amplified resist composition comprising a photoacid generator which generates a sulfonic acid selected from the group consisting of the following acids:

-continued
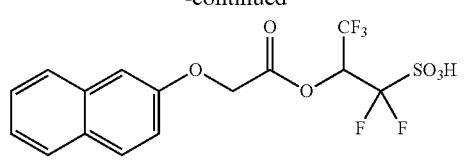
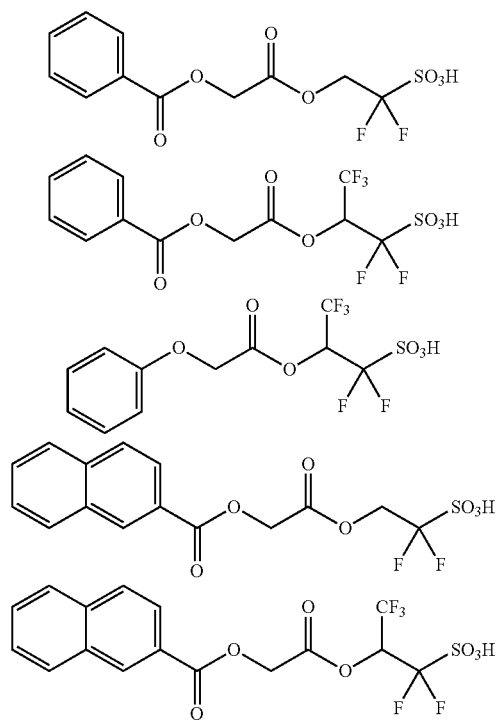
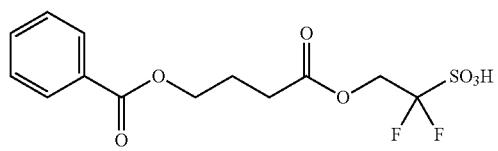
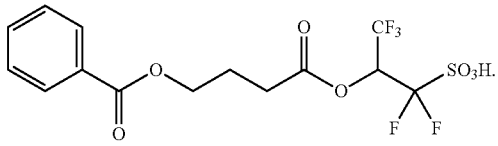
* * * * *